United States Patent
Wu et al.

(10) Patent No.: US 8,586,619 B2
(45) Date of Patent: Nov. 19, 2013

(54) AGENTS OF CALCIUM ION CHANNEL MODULATORS

(75) Inventors: Jay Jie-Qiang Wu, Fremont, CA (US); Jian-Xin Guo, Lawrence, KS (US); Luat T. Nguyen, San Jose, CA (US)

(73) Assignee: VM Therapeutics LLC, Fremont, CA (US)

( * ) Notice: Subject to any disclaimer, the term of this patent is extended or adjusted under 35 U.S.C. 154(b) by 538 days.

(21) Appl. No.: 12/530,964

(22) PCT Filed: Mar. 12, 2008
(Under 37 CFR 1.47)

(86) PCT No.: PCT/US2008/056569
§ 371 (c)(1),
(2), (4) Date: Jul. 1, 2010

(87) PCT Pub. No.: WO2008/112715
PCT Pub. Date: Sep. 18, 2008

(65) Prior Publication Data
US 2011/0065703 A1    Mar. 17, 2011

Related U.S. Application Data

(60) Provisional application No. 60/894,368, filed on Mar. 12, 2007.

(51) Int. Cl.
*A61K 31/40* (2006.01)
*A61K 31/34* (2006.01)
*C07D 405/04* (2006.01)
*C07D 307/93* (2006.01)

(52) U.S. Cl.
USPC ............ 514/412; 514/469; 548/525; 549/465

(58) Field of Classification Search
USPC .................... 514/412, 469; 548/525; 549/465
See application file for complete search history.

(56) References Cited

U.S. PATENT DOCUMENTS

| 6,160,009 A | 12/2000 | Massey et al. |
| 6,268,507 B1 | 7/2001 | Massey et al. |
| 2006/0003985 A1 | 1/2006 | Renger et al. |

FOREIGN PATENT DOCUMENTS

| WO | WO 00/59882 A | 10/2000 |
| WO | WO 2008/092681 A | 8/2008 |

OTHER PUBLICATIONS

Ben Small D, Samuel C, Rouy-Thenaisy K, Régnault J, Azouvi P. Bromocriptine in traumatic brain injury. Brain Inj. Jan. 2006;20(1):111-5.*
Ito N, Tamano S, Shirai T. A medium-term rat liver bioassay for rapid in vivo detection of carcinogenic potential of chemicals. Cancer Sci. Jan. 2003;94(1):3-8.*
Pedrosa R, Sayalero S, Vicente M, Casado B. Chiral template mediated diastereoselective intramolecular Diels-Alder reaction using furan as a diene. Toward the synthesis of enantiopure trisubstituted tetrahydroepoxyisoindolones. J Org Chem. Sep. 2, 2005;70(18):7273-8.*
Takano S, Oshima Y, Ito F, Ogasawara K. Diels-Alder Reaction of Furfurylamine Derivatives with Maleic Anhydride and Its Stereochemistry. Yakagaku Zasshi. Dec. 1980; 100(12): 1194-1202.*
International Search Report based on International Application PCT/US08/56569 (Sep. 2, 2008).
European Supplementary Search Report based on EP Application 08731934 (National Stage of International Application PCT/US08/56569, Jul. 9, 2009).

* cited by examiner

*Primary Examiner* — Paul Zarek
(74) *Attorney, Agent, or Firm* — Cooley LLP

(57) ABSTRACT

The present invention includes a group of chemical compounds useful as modulators of calcium ion ($Ca^{2+}$) channels, especially for T-type, N-Type and L-type channels. The present invention also includes pharmaceutical compositions comprising these calcium ion channel modulating agents and methods of using these calcium ion channel modulating agents for the treatment diseases and conditions associated with the calcium ion channels.

13 Claims, 2 Drawing Sheets

AGENTS OF CALCIUM ION CHANNEL MODULATORS

CROSS-REFERENCE TO RELATED APPLICATIONS

This application is a U.S. National Stage application of International Application number PCT/US2008/056569, filed on Mar. 12, 2008 and entitled "Novel Agents for Calcium Ion Channel Modulators", which claims priority to U.S. provisional application Ser. No. 60/894,368 filed, Mar. 12, 2007, which is incorporated by reference herein in its entirety for all purposes.

FIELD OF THE INVENTION

The present invention generally relates to a group of chemical compounds useful as modulators of calcium ion ($Ca^{2+}$) channels, in particularly as T-, N- and L-type calcium channels modulators and pharmaceutical composition useful for the modulation of calcium ion channels activity for prevent and treatment of diseases related with calcium ion channels.

BACKGROUND OF THE INVENTION

Calcium ion channels are membrane-spanning, multi-subunit proteins that allow $Ca^{2+}$ entry from the external milieu and concurrent depolarization of the cell's membrane potential, and play a central role in neurotransmitter release. Traditionally calcium ion channels have been classified based on their functional characteristics such as low voltage or high voltage activated and their kinetics (L, T, N, P, Q). The ability to clone and express the calcium ion channel subunits has lead to an increased understanding of the channel composition that produces these functional responses. Calcium channels can be classified into a number of types and subtypes, for example L-(or Cav1), P/Q-(or Cav2.1), N-(or Cav2.2), R-(Cav2.3) and T-(or Cav3) types. T-type calcium channels can, for example, be molecularly, pharmacologically and electrophysiologically sub-classified into α1G (or Cav3.1), α1H (or Cav3.2), and α1I (or Cav3.3) T channels from various warm blooded animals including rat. The "T-type" (or "low voltage-activated") calcium channels are so named because their openings are of briefer duration (T=transition) than the longer (L=long-lasting) openings of the L-type calcium channels. The L, N, P and Q-type channels activate at more positive potentials (high voltage activated) and display diverse kinetics and voltage-dependent properties. See e.g. Catterall, Annu. Rev. Cell Dev. Biol. 16, 521-55, (2000) and Perez-Reyes Physiol. Rev. 83, 117-161, (2003).

The pharmacology of the three subfamilies of calcium ion channels is quite distinct from each other. The type I Cav1 (L-type) channels are distributed within cardiac muscle, smooth muscle including blood vessels, intestine, lung, uterus, skeletal muscale, endocrine cells, and are the molecular targets of the organic calcium channel blockers used widely in the therapy of cardiovascular diseases.

The type II Cav2 (P, Q, N. R) channels are in neurons, heart, etc. They are relatively insensitive to dihydropyridine calcium channel blockers, but these channels are specifically blocked with high affinity by peptide toxins from spiders and marine snails. The N type $Ca^{2+}$ channel (Cav2.2) is highly expressed at the presynaptic nerve terminals of the dorsal root ganglion as it forms a synapse with the dorsal horn neurons in lamina I and II. These neurons in turn have large numbers of N type $Ca^{2+}$ channels at their presynaptic terminals as they synapse onto second and third order neurons. This pathway is very important in relaying pain information to the brain. The N type $Ca^{2+}$ channel has been validated in man by intrathecal infusion of the toxin Ziconotide for the treatment of intractable pain, cancer pain, opioid resistant pain, and neuropathic and severe pain. The toxin has over 80% success rate for the treatment of pain in humans with a greater potency than morphine. However, Ziconotide causes mast cell degranulation and produces dose-dependent central side effects. These include dizziness, nystagmus, agitation, and dysmetria. There is also orthostatic hypotension in some patients at high doses. It is believed that this may be due to Ziconotide induced mast cell degranulation and/or its effects on the sympathetic ganglion that like the dorsal root ganglion also expresses the N type $Ca^{2+}$ channel. Use-dependent compounds that block preferentially in the higher frequency range >10 Hz should be helpful in minimizing these potential side-effect issues. The firing rate in man of the sympathetic efferents is in the 0.3 Hz range. CNS neurons can fire at high frequencies but generally only do so in short bursts of action potentials. Even with the selectivity imparted by use-dependence intrinsic selectivity against the L type calcium channel is still necessary as it is involved in cardiac and vascular smooth muscle contraction.

The third type Cav3 (T-type) channels exist in brain, heart, kidney, liver, etc. They are insensitive to both the dihydropyridines that block Cav1 channels and the spider and cone snail toxins that block the Cav2 channels. T-type $Ca^{2+}$ channels are new anticipated to be novel therapeutic targets for the treatment of various cardiovascular disorders such as heart failure, arrhythmia, hypertension, neuronal disorders such as epilepsy and pain, as well as cancer. Inhibition of T-type $Ca^{2+}$ channels may result in long-term organ protection through improvement of local microcirculation and reduction of adverse hormonal effects. However, there are no widely useful pharmacological agents that block T-type calcium currents. The organic calcium channel blocker mibefradil is somewhat selective for T-type versus L-type calcium current and showed strong side effects due to drug interaction at the cytochrome P-450 3A4 enzyme which was unrelated to T-type $Ca^{2+}$ channel blockade. The peptide kurtoxin inhibits the activation gating of Cav3.1 and Cav3.2 channels. Development of more specific and high-affinity blockers of the Cav3 family of calcium channels would be useful for therapy and a more detailed analysis of the physiological roles of these channels. The T-type $Ca^{2+}$ channel has properties different from those of the L-type such as more negative voltage range of activation and inactivation, rapid gating kinetics, and resistance to standard $Ca^{2+}$ blockers such as $Ca^{2+}$ channel blockers, which block L-type $Ca^{2+}$ channels.

T-type calcium channels have been implicated in pathologies related to various diseases and disorders, including epilepsy, essential tremor, pain, neuropathic pain, schizophrenia, Parkinson's disease, depression, anxiety, sleep disorders, sleep disturbances, psychosis, schizophreniac, cardiac arrhythmia, hypertension, certain types of cancer, diabetes, infertility, sexual dysfunction and cancer (J Neuroscience, 14, 5485 (1994); Drug Future 30(6), 573-580 (2005); EMBO J, 24, 315-324 (2005)).

The known therapeutic regimens for such treating such diseases and disorders suffer from numerous problems and a number of side effects. These side effects include various CNS disturbances such as blurred vision, dizziness, nausea, and sedation as well more potentially life threatening cardiac arrhythmias and cardiac failure. Accordingly, a more physiological way, to develop additional $Ca^{2+}$ channel blockers/antagonists, preferably those with higher potency, high selectivity and fewer side effects, to treat these diseases and disorders would be highly desirable.

SUMMARY OF THE INVENTION

The present invention provides several classes of compounds, including their enantiomers, diastereomers, salts, solvates, esters, and/or prodrugs thereof, and their derivation with additional functional chemical groups and chemical modifications that is highly similar to the listed compounds, as the modulators of the calcium ion channels, especially as the blockers or antagonists of T-type and N-type calcium ion channels, and the therapeutic uses of those agent or mixtures containing one or more those agents in disease associated with calcium ion channels.

In one aspect, the present invention provides a compound having a structural Formula (I), or a salt, solvate, ester, and/or prodrug thereof:

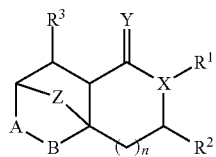

(I)

wherein:
A-B is —CHR$^4$CHR$^5$— or —CR$^4$=CR$^5$—;
X is —CR$^6$— or —N—;
Y is O, NR$^2$, or S;
Z is —O—, —NR$^9$—, —S—, or —CR$^{11}$R$^{12}$—;
n is 0 or 1;
R$^1$ is hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;
R$^2$ is hydrogen, acyl, substituted acyl, alkoxycarbonyl, substituted alkoxycarbonyl, aryloxycarbonyl, substituted aryloxycarbonyl, —CONR$^{15}$R$^{16}$, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;
R$^3$ is hydrogen, acyl, substituted acyl, alkoxycarbonyl, substituted alkoxycarbonyl, aryloxycarbonyl, substituted aryloxycarbonyl, —CONR$^{12}$R$^{18}$, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;
R$^4$, R$^5$, R$^6$, R$^7$, R$^8$, R$^9$, R$^{10}$, R$^{11}$, and R$^{12}$ are independently hydrogen, alkyl, substituted alkyl, aryl, substituted aryl, arylalkyl or substituted arylalkyl;
R$^{15}$ and R$^{16}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, R$^{15}$ and R$^{16}$, taken together with the nitrogen atom to which they are attached, form a 4-, 5-, 6- or 7-membered cycloheteroalkyl ring, provided that both R$^{15}$ and R$^{16}$ are not hydrogen; and
R$^{17}$ and R$^{18}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, R$^{15}$ and R$^{16}$, taken together with the nitrogen atom to which they are attached, form a 4-, 5-, 6- or 7-membered cycloheteroalkyl ring, provided that both R$^{15}$ and R$^{16}$ are not hydrogen;
with the proviso that at least one of R$^1$, R$^2$ and R$^3$ is not hydrogen; and
a pharmaceutically acceptable vehicle.

In another aspect, the present invention provides a pharmaceutical composition comprising a compound having a structural Formula (I) as defined above, or a salt, solvate, ester, and/or prodrug thereof, and a pharmaceutically acceptable vehicle.

In another aspect, the present invention provides a method for treating a condition, disorder, or disease, or stimulating contraceptive effect, in a patient in need thereof comprising administering to the patient a therapeutically effective amount of the compound of formula (I) as defined above, or a salt, solvent, ester, and/or prodrug thereof, wherein the condition, disorder, or disease is implicated in the activation or hyperactivity of low voltage-gated calcium channels.

In another aspect, the present invention provides a method of modulating calcium ion channels comprising contacting the compound of formula (I) as defined above, or a salt, solvent, ester, and/or prodrug thereof, with the calcium ion channels.

In another aspect, the present invention provides a compound having a structural formula (II), (III) or (IV), or a salt, solvate, ester, and/or prodrug thereof,

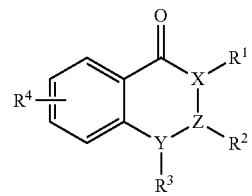

(II)

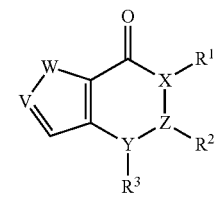

(III)

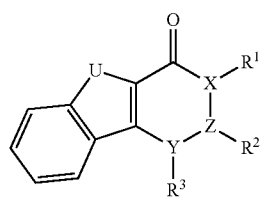

(IV)

wherein:
X—Z is —C=C— or —N—C—;
Y—Z is —N—C—, —N=C—, —CH—CH— or —S—CH—;
provided that X—Z is not —C=C— when Y—Z is —N=C—;
R$^1$ is —S(O)$_k$R$^5$, —NH—S(O)$_k$R$^5$, alkyl, substituted alkyl, aryl, substituted aryl, arylalkyl, substituted arylalkyl, cycloalkylalkyl, substituted cycloalkylalkyl, cycloheteroalkylalkyl, substituted cycloheteroalkylalkyl, heteroaryl, substituted heteroaryl, heteroarylalkyl, substituted heteroarylalkyl, heteroalkyl, substituted heteroalkyl, —CONR$^6$R$^7$ or alternatively R¹ and R² along with the atoms to which they are attached form a cycloalkyl, substituted cycloalkyl, cycloheteroalkyl, substituted cycloheteroalkyl, aryl, substituted aryl, heteroaryl, substituted heteroaryl ring, fused indanoyl or substituted fused indanoyl ring;

k is 0, 1 or 2;

R² is hydrogen, —S(O)$_l$R⁸, =O, —NR²¹COR¹⁸, —NR¹⁹R²⁰, alkoxycarbonyl, substituted alkoxycarbonyl, alkyl, substituted alkyl, aryl, substituted aryl, arylalkyl, substituted arylalkyl, heteroaryl, substituted heteroaryl, heteroarylalkyl, substituted heteroarylalkyl or alternatively R² and R³ along with the atoms to which they are attached form a cycloalkyl, substituted cycloalkyl, cycloheteroalkyl, substituted cycloheteroalkyl, aryl, substituted aryl, heteroaryl or substituted heteroaryl ring;

l is 0, 1 or 2;

R³ is hydrogen, alkyl, substituted alkyl, arylalkyl, substituted arylalkyl, heteroaryl, substituted heteroaryl, heteroarylalkyl, substituted heteroarylalkyl, heteroalkyl, substituted heteroalkyl or —CONR⁸R⁹ when Y—Z is —N—C—, or —CH—CH— and is not defined when Y—Z is —N=C—;

provided that R² does not form a ring with both R¹ and R³;

R⁴ is alkyl, acyl, substituted acyl, acyloxycarbonyl, substituted acyloxycarbonyl, aryloxycarbonyl, substituted aryloxycarbonyl, alkoxy, substituted alkoxy, alkyl, substituted alkyl, arylalkyl, substituted arylalkyl, heteroaryl, substituted heteroaryl, heteroarylalkyl, substituted heteroarylalkyl, heteroalkyl, substituted arylalkyl, halo, hydroxyl, nitro, cyano, —CONR¹⁰R¹¹, —NR¹²R¹³, carboxyl or —S(O)$_m$R¹⁴;

m is 0, 1 or 2;

R⁵, R⁸ and R¹⁴ are independently alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;

R⁶ and R⁷ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively R⁶ and R⁷ along with the atoms to which they are attached form a cycloheteroalkyl or substituted cycloheteroalkyl, ring;

R⁸ and R⁹ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or attentively R⁸ and R⁹ along with the atoms to which they are attached form a cycloheteroalkyl or substituted cycloheteroalkyl, ring;

R¹⁰ and R¹¹ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively R¹⁰ and R¹¹ along with the atoms to which they are attached form a cycloheteroalkyl or substituted cycloheteroalkyl, ring;

R¹² and R¹³ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively R¹² and R¹³ along with the atoms to which they are attached form a cycloheteroalkyl or substituted cycloheteroalkyl, ring;

W is —O—, —NR¹⁵ or —S—;
U is —O—, —NR¹⁶ or —S—;
V is —CH— or —N—;

R¹⁵ and R¹⁶ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;

R¹⁸ and R²¹ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl; and R¹⁹ and R²⁰ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;

provided that Formula (II), (III), or (IV) does not include 3-{2-[4-(4-Fluoro-benzoyl)-piperidin-1-yl]-ethyl}-1H-quinazoline-2,4-dione.

In another aspect, the present invention provides a pharmaceutical composition comprising a compound of formula (II), (III), or (IV) as defined above, or a salt, solvate, ester, and/or prodrug thereof; and a pharmaceutically acceptable vehicle.

In another aspect, the present invention provides a method for treating a condition, disorder, or disease, or stimulating contraceptive effect, in a patient in need thereof comprising administering to the patient a therapeutically effective amount of the compound of formula (II), (III), or (IV) as defined above, or a salt, solvent, ester, and/or prodrug thereof, wherein the condition, disorder, or disease is implicated in the activation or hyperactivity of low voltage-gated calcium channels.

In another aspect, the present invention provides a method of modulating calcium ion channels comprising contacting the compound of formula (II), (III), or (IV) as defined above, or a salt, solvent, ester, and/or prodrug thereof, with the calcium ion channels.

In another aspect, the present invention provides a method of treating a condition, disorder, or disease, or stimulating contraceptive effect, in a patient in need thereof, comprising administering to the patient a therapeutically effective amount of a compound having structural formula (XII), or a salt, solvate, ester, and/or prodrug thereof, wherein the condition, disorder, or disease is implicated in the activation or hyperactivity of low voltage-gated calcium channels,

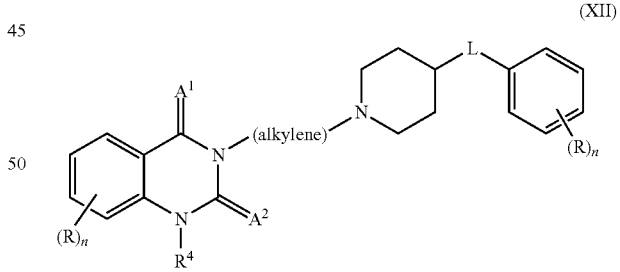

(XII)

wherein

A¹ and A² are each independently O, S, N—R, or N—OR;

R⁴ is hydrogen, alkyl, substituted alkyl, heteroalkyl, substituted heteroalkyl, hydroxyl, alkoxy, amino, or alkamino;

L is each independently —C(O)—, —C(=S)—, —C(=NR¹)—, —C(=N—OR¹)—, —S(O)—, —S(O)₂—, or —C(R²R³)—;

R is each independently halo, alkyl, substituted alkyl, heteroalkyl, substituted heteroalkyl, hydroxyl, alkoxy, amino, alkamino, cyano, or nitro;

n is an integer of 0, 1, 2, 3, or 4; and m is an integer of 0, 1, or 2.

In another aspect, the present invention provides a method of modulating calcium ion channels comprising contacting the compound having a structural formula (XII) as defined above, or a salt, solvent, ester, and/or prodrug thereof, with the calcium ion channels.

In another aspect, the present invention provides a method of treating a condition, disorder, or disease, or stimulating contraceptive effect, in a patient in need thereof, comprising administering to the patient a therapeutically effective amount of a compound selected from the group consisting of cyclopentyl[3-(2-methoxy-4-{[(2-methylphenyl)sulfonyl]carbamoyl}benzyl)-1-methyl-1H-indol-5-yl]carbamate (Zafirlukast); (5'α)-2-bromo-12'-hydroxy-5'-(2-methylpropyl)-3',6',18-trioxo-2'-(propan-2-yl)ergotaman (Bromocriptine); and 4,4'-(propane-2,2-diyldisulfanediyl)bis(2,6-di-tert-butylphenol) (Probucol), or a salt, solvate, ester, and/or prodrug thereof, wherein the condition, disorder, or disease is implicated in the activation or hyperactivity of low voltage-gated calcium channels.

In another aspect, the present invention provides a method of modulating calcium ion channels comprising contacting a compound selected from the group consisting of cyclopentyl[3-(2-methoxy-4-{[(2-methylphenyl)sulfonyl]carbamoyl}benzyl)-1-methyl-1H-indol-5-yl]carbamate (Zafirlukast); (5'α)-2-bromo-12'-hydroxy-5'-(2-methylpropyl)-3',6',18-trioxo-2'-(propan-2-yl)ergotaman (Bromocriptine); and 4,4'-(propane-2,2-diyldisulfanediyl)bis(2,6-di-tert-butylphenol) (Probucol), or a salt, solvent, ester, and/or prodrug thereof, with the calcium ion channels.

DETAILED DISCLOSURE OF THE INVENTION

Definitions

Figure 1:
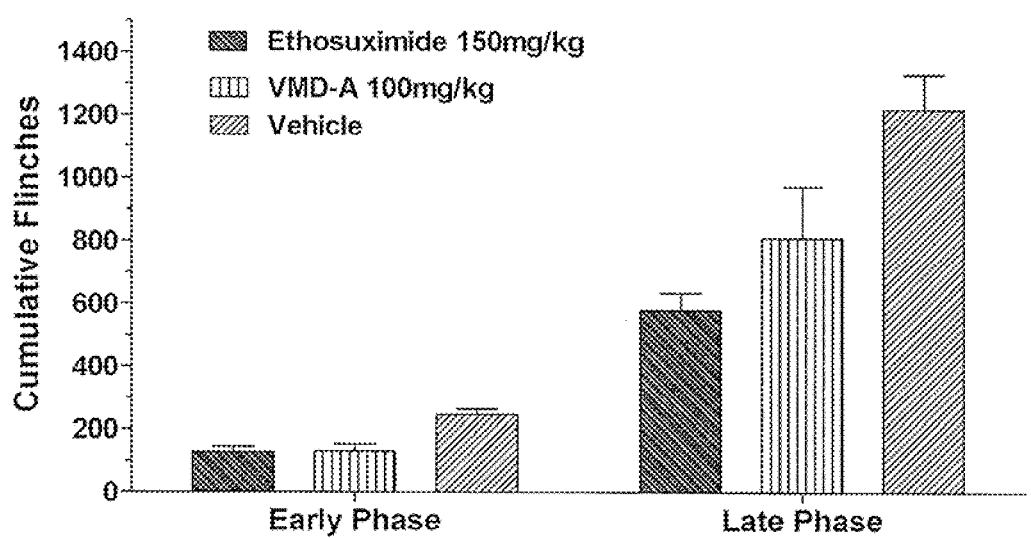
FIG. 1 is a graph showing reduction of Formalin induced pain in rat animal models of hyperalgesia by the compound (52): VMD-A.

"Alkyl" by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl(allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl).

"Alkanyl" by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl(t-butyl), cyclobutan-1-yl, etc.; and the like.

"Alkenyl" by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl(allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy" by itself or as part of another substituent, refers to a radical of the formula —O—R, where R is alkyl or substituted alkyl as defined herein.

"Alkoxycarbonyl" by itself or as part of another substituent, refers to a radical of the formula —C(O)O—R, where R is alkyl or substituted alkyl as defined herein.

"Alkamino" by itself or as part of another substituent refers to a radical —NHR or —NR$_2$, wherein R is alkyl or substituted alkyl.

"Acyl" by itself or as part of another substituent refers to a radical —C(O)R, where R is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$)alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$)alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$)alkyl and the aryl moiety is ($C_6$-$C_{10}$) aryl.

"Aryloxycarbonyl," by itself or as part of another substituent, refers to a radical of the formula —C(O)—O—$R^{32}$, where $R^{32}$ is aryl, substituted aryl, arylalkyl, substituted arylalkyl, heteroaryl, substituted heteroaryl, heteroarylalkyl or substituted heteroarylalkyl.

"Cycloalkyl or carbocyclyl," by itself or as part of another substituent, refers to a saturated or unsaturated cyclic alkyl radical, as defined herein. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In some embodiments, the cycloalkyl group comprises from 3 to 10 ring atoms ($C_3$-$C_{10}$ cycloalkyl). In other embodiments, the cycloalkyl group comprises from 3 to 7 ring atoms ($C_3$-$C_7$ cycloalkyl).

"Cycloalkylalkyl," by itself or as part of another substituent, refers to an acyclic alkyl group in which one of the hydrogen atoms bonded to a carbon atom, typically a terminal or $sp^3$ carbon atom, is replaced with an cycloalkyl group as, as defined herein.

"Cycloheteroalkyl or heterocyclyl," by itself or as part of another substituent, refers to a saturated or unsaturated cyclic alkyl radical in which one or more carbon atoms (and optionally any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, and the like. In some embodiments, the cycloheteroalkyl group comprises from 3 to 10 ring atoms (3-10 membered cycloheteroalkyl) In other embodiments, the cycloalkyl group comprise from 5 to 7 ring atoms (5-7 membered cycloheteroalkyl).

A cycloheteroalkyl group may be substituted at a heteroatom, for example, a nitrogen atom, with a ($C_1$-$C_6$)alkyl group. As specific examples, N-methyl-imidazolidinyl, N-methylmorpholinyl, N-methyl-piperazinyl, N-methyl-piperidinyl, N-methyl-pyrazolidinyl and N-methyl-pyrrolidinyl are included within the definition of "cycloheteroalkyl." A cycloheteroalkyl group may be attached to the remainder of the molecule via a ring carbon atom or a ring heteroatom.

"Cycloheteroalkylalkyl," by itself or as part of another substituent, refers to an acyclic alkyl group in which one of the hydrogen atoms bonded to a carbon atom, typically a terminal or $sp^3$ carbon atom, is replaced with an cycloheteroalkyl group as, as defined herein.

"Fused Indanoyl," by itself or as part of another substituent, refers to the fused ring system below:

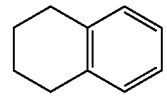

"Heteroalkyl," "Heteroalkanyl," "Heteroalkynyl" and "Heteroalkynyl," "by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, O, S, N, Si, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —N$R^{35}R^{36}$—, =N—N=, —N=N—, —N=N—N$R^{37}R^{38}$, —P$R^{39}$—, —P(O)$_2$—, —PO$R^{40}$—, —O—P(O)$_2$—, —SO—, —SO$_2$—, —Sn$R^{41}R^{42}$— and the like, where $R^{35}$, $R^{36}$, $R^{37}$, $R^{38}$, $R^{39}$, $R^{40}$, $R^{41}$ and $R^{42}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is $(C_1-C_6)$alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is $(C_1-C_3)$alkyl and the heteroaryl moiety is a 5-10 membered heteroaryl.

"Implicated" means culpably involved or causually connected to.

"Modulating" refers to adjusting, varying, or changing. As used herein, modulation of calcium ion channel includes antagonizing, agonizing, or partially antagonizing. That is, the compounds of the present invention may act as antagonists, agonists, or partial antagonists of the calcium ion channel activity.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Patient" includes mammals, such as, for example, humans.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and ally) ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Prodrug or softdrug" refers to a precursor of a pharmaceutically active compound wherein the precursor itself may or may not be pharmaceutically active but, upon administration, will be converted, either metabolically or otherwise, into the pharmaceutically active compound or drug of interest. For example, prodrug or softdrug is an ester or an ether form of a pharmaceutically active compound. Several prodrugs have been prepared and disclosed for a variety of pharmaceuticals. See, for example, Bundgaard, H. and Moss, J., J. Pharm. Sci. 78: 122-126 (1989). Thus, one of ordinary skill in the art knows how to prepare these precursors, prodrugs or softdrugs with commonly employed techniques of organic synthesis.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2Or^b$, —$OS(O)_2R^b$, —OS$(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)$ NR$^c$R$^c$, where R$^a$ is selected from the group consisting of alkyl, cycloalkyl, heteroalkyl, cycloheteroalkyl, aryl, arylalkyl, heteroaryl and heteroarylalkyl; each R$^b$ is independently hydrogen or R$^a$; and each R$^c$ is independently R$^b$ or alternatively, the two R$^c$s are taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —NR$^c$R$^c$ is meant to include —NH$_2$, —NH-alkyl, N-pyrrolidinyl and N-morpholinyl.

Similarly, substituent groups useful for substituting unsaturated carbon atoms in the specified group or radical include, but are not limited to, —R$^a$, halo, —O$^-$, —OR$^b$, —SR$^b$, —S$^-$, —NR$^c$R$^c$, trihalomethyl, —CF$_3$, —CN, —OCN, —SCN, —NO, —NO$_2$, —N$_3$, —S(O)$_2$R$^b$, —S(O)$_2$O$^-$, —S(O)$_2$OR$^b$, —OS(O)$_2$R$^b$, —OS(O)$_2$O$^-$, —OS(O)$_2$OR$^b$, —P(O)(O$^-$)$_2$, —P(O)(OR$^b$)(O$^-$), —P(O)(OR$^b$)(OR$^b$), —C(O)R$^b$, —C(S)R$^b$, —C(NR$^b$)R$^b$, —C(O)O$^-$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)O$^-$, —OC(O)OR$^b$, —OC(S)OR$^b$, —NR$^b$C(O)R$^b$, —NR$^b$C(S)R$^b$, —NR$^b$C(O)O$^-$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined.

Substituent groups useful for substituting nitrogen atoms in heteroalkyl and cycloheteroalkyl groups include, but are not limited to, —R$^a$, —O$^-$, —OR$^b$, —SR$^b$, —S$^-$, —NR$^c$R$^c$, trihalomethyl, —CF$_3$, —CN, —NO, —NO$_2$, —S(O)$_2$R$^b$, —S(O)$_2$O$^-$, —S(O)$_2$OR$^b$, —OS(O)$_2$R$^b$, —OS(O)$_2$O$^-$, —OS(O)$_2$OR$^b$, —P(O)(O$^-$)$_2$, —P(O)(OR$^b$)(O$^-$), —P(O)(OR$^b$)(OR$^b$), —C(O)R$^b$, —C(S)R$^b$, —C(NR$^b$)R$^b$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)OR$^b$, —OC(S)OR$^b$, —NR$^b$C(O)R$^b$, —NR$^b$C(S)R$^b$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Treating" or "treatment" of any disease or disorder refers, in some embodiments, to ameliorating or preventing the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

"Vehicle" refers to a diluent, adjuvant, excipient or carrier with which a compound is administered.

The term "a compound of the present invention", "the compound of the present invention", "compounds of the present invention", or "the present compounds" includes one or more compounds covered by the generic formula (I), (II), (III), (IV), (V), (VI), (VII), (VIII), (IX), (X), (XI), (XII), cyclopentyl[3-(2-methoxy-4-{[(2-methylphenyl)sulfonyl]carbamoyl}benzyl)-1-methyl-1H-indol-5-yl]carbamate (Zafirlukast), (5'α)-2-bromo-12'-hydroxy-5'-(2-methylpropyl)-3',6',18-trioxo-2'-(propan-2-yl)ergotaman (Bromocriptine), and 4,4'-(propane-2,2-diyldisulfanediyl)bis(2,6-di-tert-butylphenol) (Probucol); and/or any subgenric formula thereof including the racemic mixtures, enantiomers, diastereomers, tautomers, and other isomers thereof.

These compounds and pharmaceutically acceptable compositions are useful for treating or lessening the severity of a variety of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

T-channel blockers are also useful for the treatment of sleep disorders, mood disorders, depression, migraine headache, neuronal excitability disorders, hypertension, stroke, cardiovascular diseases, hyperaldosteronemia, preterm labor, urinary incontinence, brain aging, or neurodegenerative related diseases such as Alzheimer's disease. See e.g., WO 01/02561; WO 00/02455; JP11035483; and Chemin, J. Physiol., 540, 3-14, (2002). Additionally, T-type calcium channels play a role in pancreatic beta-cell insulin secretion. Therefore, T-type blockers may be useful for treatment of hypo- and hyperinsulinemia and the treatment and/or prevention of type 1 and type 2 diabetes as well as microvascular or macrovascular diseases associated with diabetes. See, e.g., Bhattacharjee, Endocrinology, 138, 3735-40, (1997), and WO 00/15845. T-type calcium channel blockers may also be useful in the treatment of cancer. See e.g., WO 00/59882 and WO 2001019845.

Compound of the Present Invention and Their Use

In one aspect, the present invention provides a compound having a structural Formula (I), or a salt, solvate, ester, and/or prodrug thereof:

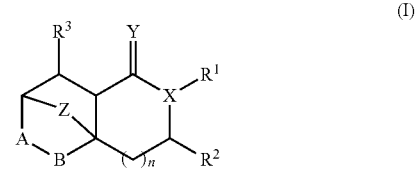

(I)

wherein:
A-B is —CHR$^4$CHR$^5$— or —CR$^4$=CR$^5$—;
X is —CR$^6$— or —N—;
Y is O, NR$^7$, or S;
Z is —O—, —NR$^9$—, —S—, or —CR$^{11}$R$^{12}$—;
n is 0 or 1;
R$^1$ is hydrogen, alkyl, substituted alkyl, aryl, substituted aryl, arylalkyl, substituted arylalkyl, heteroaryl, substituted heteroaryl, heteroarylalkyl, substituted heteroaryl alkyl, heteroalkyl or substituted heteroalkyl;
R$^2$ is hydrogen, acyl, substituted acyl, alkoxycarbonyl, substituted alkoxycarbonyl, aryloxycarbonyl, substituted aryloxycarbonyl, —CONR$^{15}$R$^{16}$, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;

R$^3$ is hydrogen, acyl, substituted acyl, alkoxycarbonyl, substituted alkoxycarbonyl, aryloxycarbonyl, substituted aryloxycarbonyl, —CONR$^{17}$R$^{18}$, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;

R$^4$, R$^5$, R$^6$, R$^7$, R$^8$, R$^9$, R$^{10}$, R$^{11}$, and R$^{12}$ are each independently hydrogen, alkyl, substituted alkyl, aryl, substituted aryl, arylalkyl or substituted arylalkyl;

R$^{15}$ and R$^{16}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, R$^{15}$ and R$^{16}$, taken together with the nitrogen atom to which they are attached, form a 4-, 5-, 6- or 7-membered cycloheteroalkyl ring, provided that, both R$^{15}$ and R$^{16}$ are not hydrogen; and R$^{17}$ and R$^{18}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, R$^{15}$ and R$^{16}$, taken together with the nitrogen atom to which they are attached, form a 4-, 5-, 6- or 7-membered cycloheteroalkyl ring, and provided that (a) R$^{15}$ and R$^{16}$ are not both hydrogen; (b) at least one of R$^1$, R$^2$ and R$^3$ is not hydrogen; and (b) the above Formula (I) does not include the compounds of Table 1.

Some representative compounds of formula (I), as examples, are given in the follow Table 1. In order that the invention described herein may be more fully understood, the following examples are set forth. It should be understood that these examples are for illustrative purposes only and are not to be construed as limiting this invention in any manner. The following compounds can be readily synthesized described in the literature by one skilled in the art of organic synthesis or readily acquired from commercially available sources.

TABLE 1

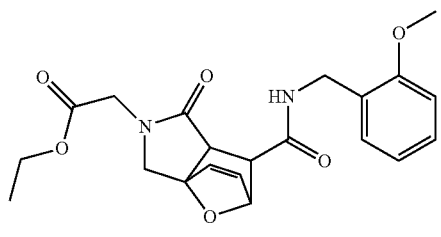

(1)

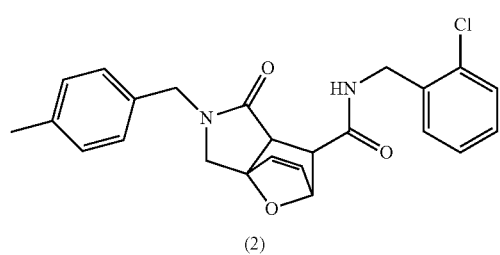 [SMILES: Cc1ccc(CN2CC34C=CC(O3)C(C(=O)NCc3ccccc3Cl)C4C2=O)cc1]

(2)

TABLE 1-continued

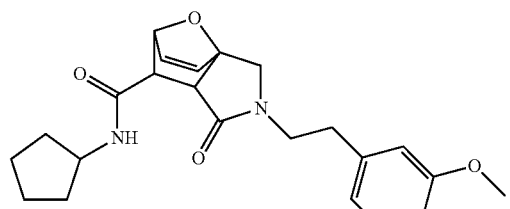

(3)

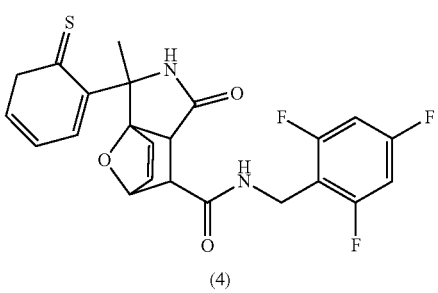 [SMILES: CC1(C2=CC=CCC2=S)NC(=O)C2C(C(=O)NCc3c(F)cc(F)cc3F)C3C=CC21O3]

(4)

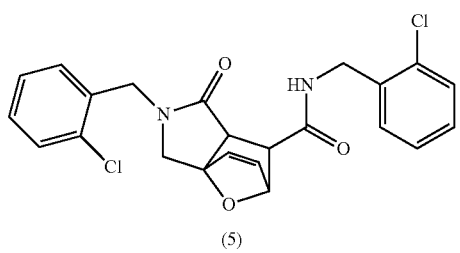 [SMILES: O=C(NCc1ccccc1Cl)C1C2C=CC3(CN(Cc4ccccc4Cl)C(=O)C13)O2]

(5)

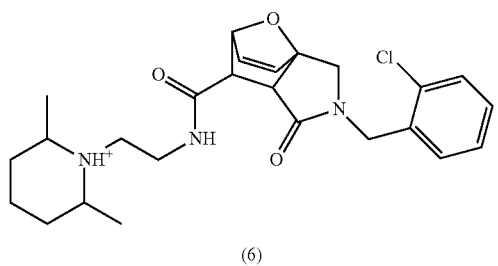 [SMILES: CC1CCCC(C)[NH+]1CCNC(=O)C1C2C=CC3(CN(Cc4ccccc4Cl)C(=O)C13)O2]

(6)

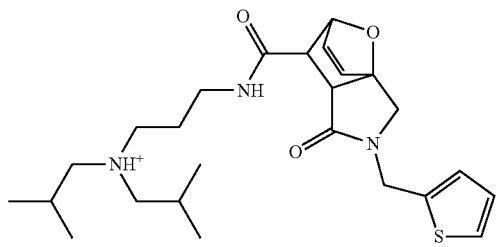

(7)

TABLE 1-continued
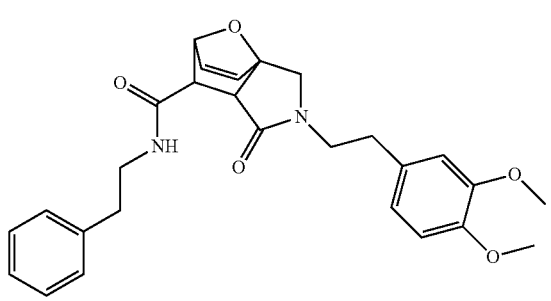
(8)
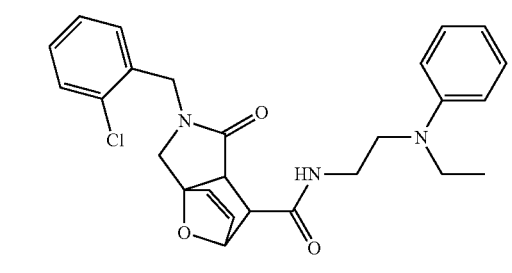
(9)
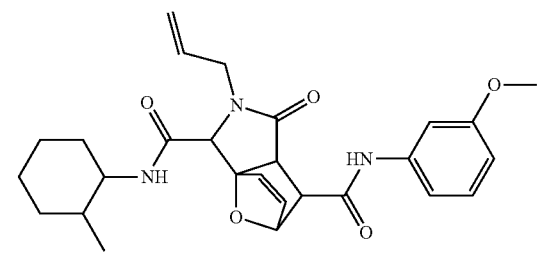
(10)
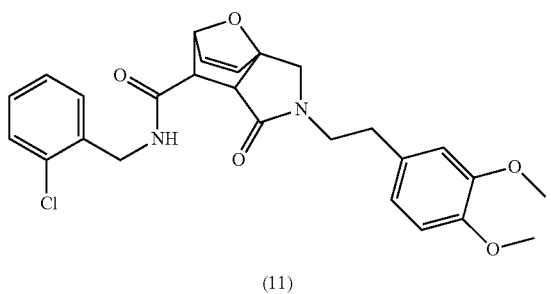 [SMILES: COc1ccc(CCN2CC34C=CC(O3)C(C(=O)NCc3ccccc3Cl)C4C2=O)cc1OC]
(11)
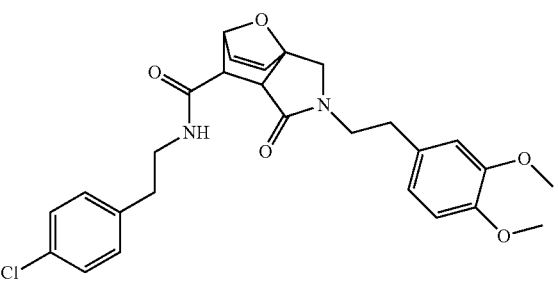
(12)
TABLE 1-continued
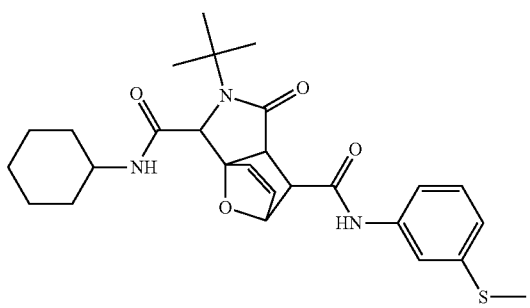
(13)
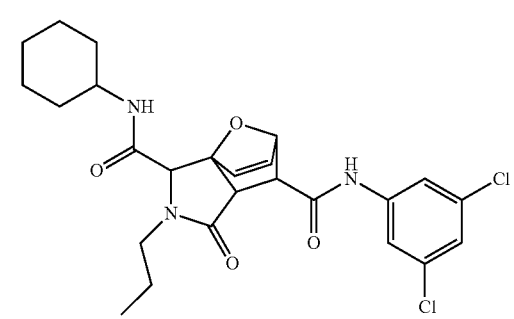
(14)
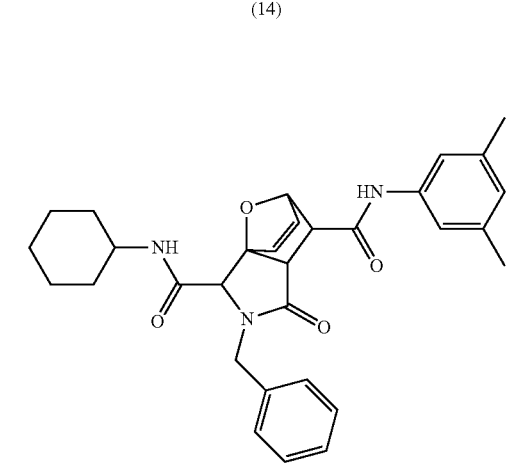
(15)
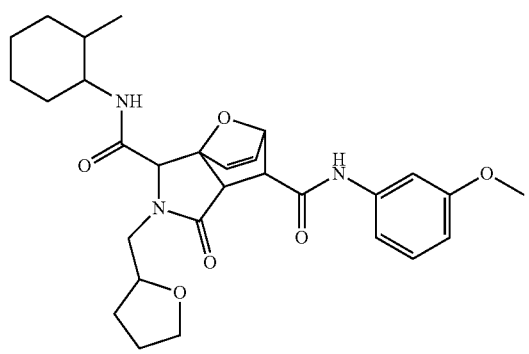
(16)

TABLE 1-continued
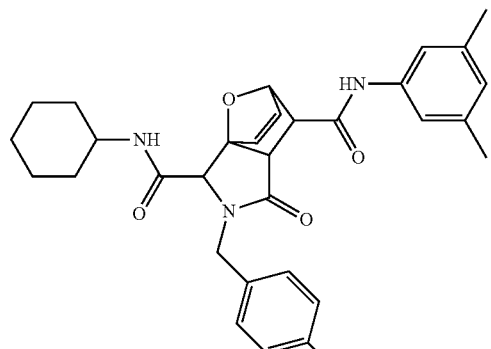
(17)
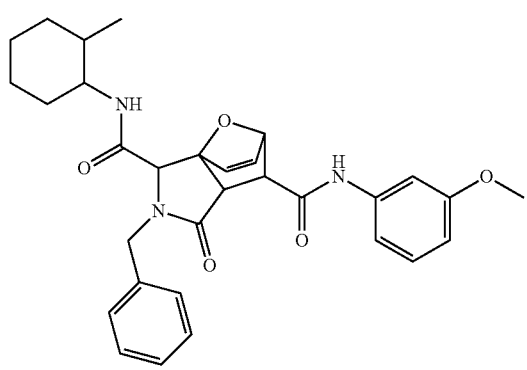
(18)
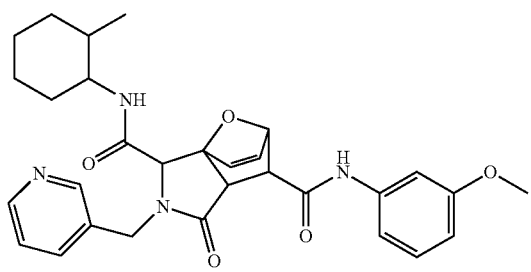
(19)
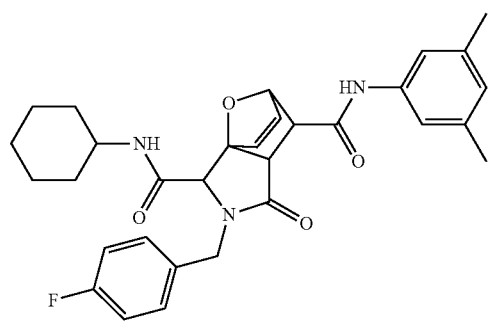
(20)
TABLE 1-continued
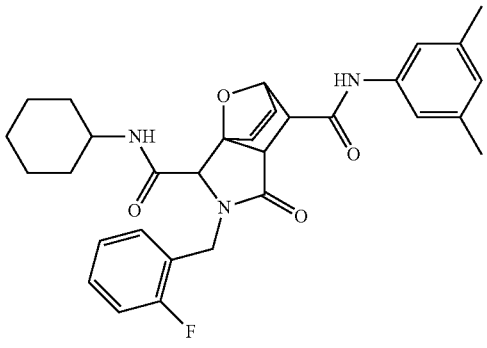
(21)
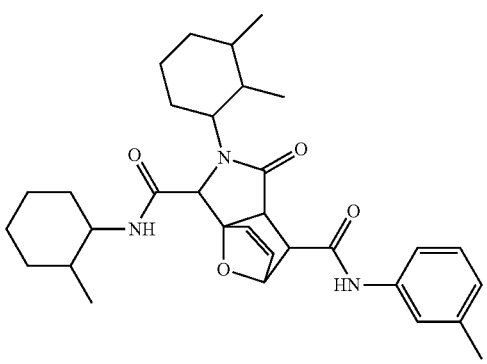
(22)
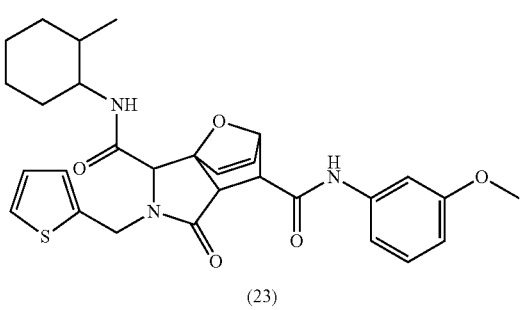 [SMILES: COc1cccc(NC(=O)C2C3C=CC4(O3)C2C(=O)N(Cc2cccs2)C4C(=O)NC2CCCCC2C)c1]
(23)
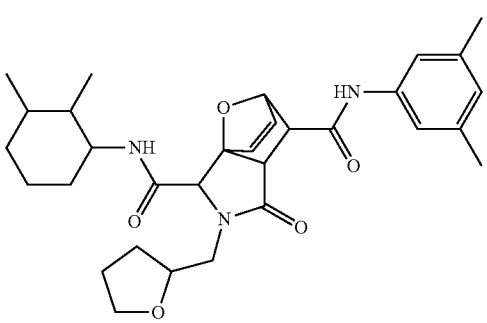
(24)

TABLE 1-continued
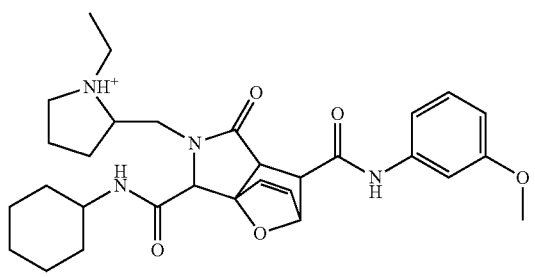
(25)
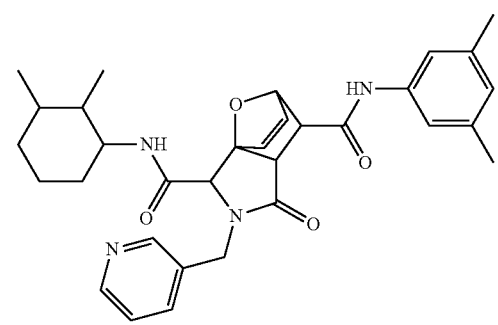
(26)
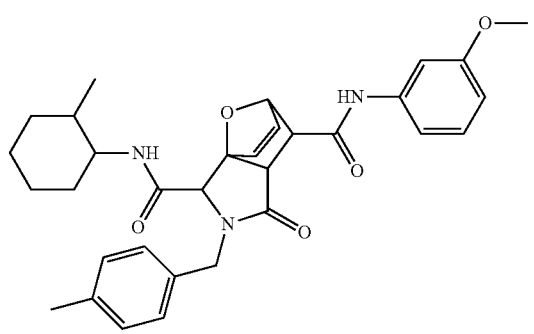
(27)
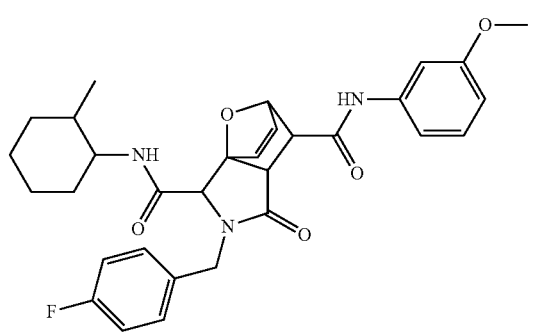
(28)
TABLE 1-continued
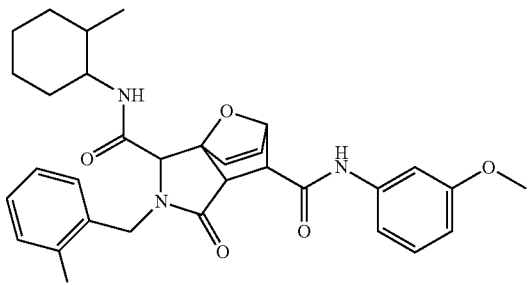
(29)
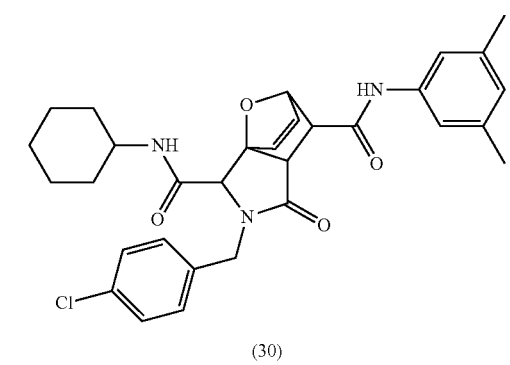 [SMILES: Cc1cc(C)cc(NC(=O)C2C3C=CC4(O3)C2C(=O)N(Cc2ccc(Cl)cc2)C4C(=O)NC2CCCCC2)c1]
(30)
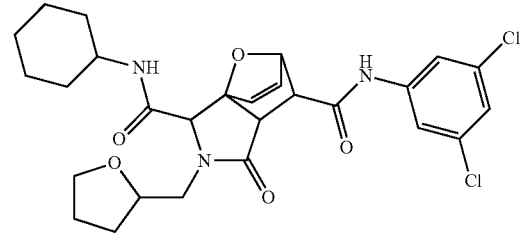
(31)
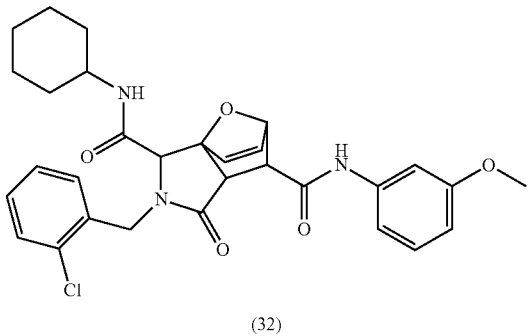 [SMILES: COc1cccc(NC(=O)C2C3C=CC4(O3)C2C(=O)N(Cc2ccccc2Cl)C4C(=O)NC2CCCCC2)c1]
(32)
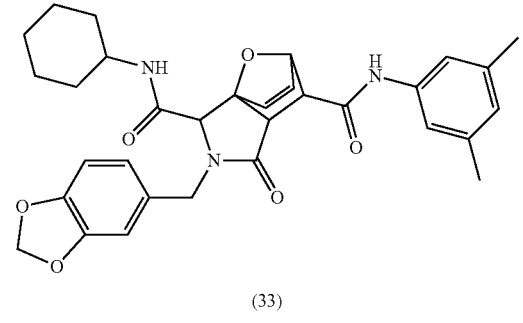 [SMILES: Cc1cc(C)cc(NC(=O)C2C3C=CC4(O3)C2C(=O)N(Cc2ccc3c(c2)OCO3)C4C(=O)NC2CCCCC2)c1]
(33)

TABLE 1-continued
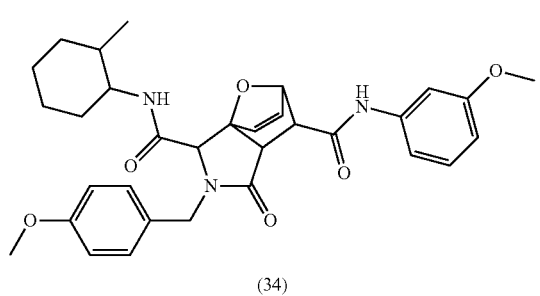
(34)
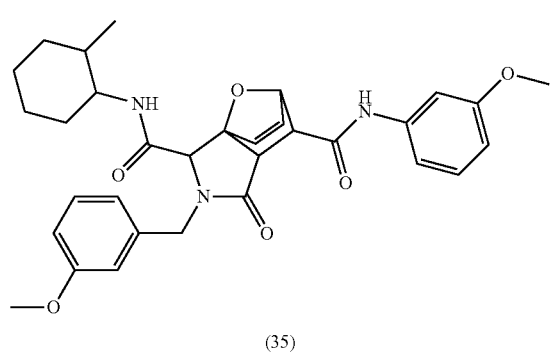
(35)
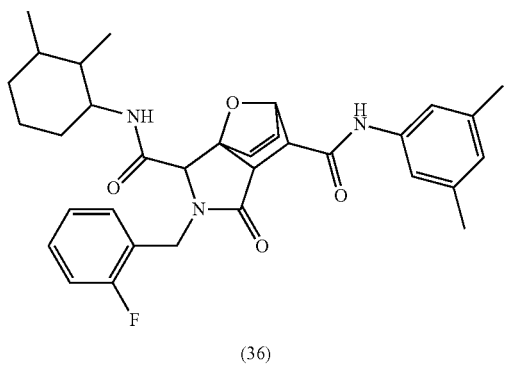 [SMILES: Cc1cc(C)cc(NC(=O)C2C3C=CC4(O3)C2C(=O)N(Cc2ccccc2F)C4C(=O)NC2CCCC(C)C2C)c1]
(36)
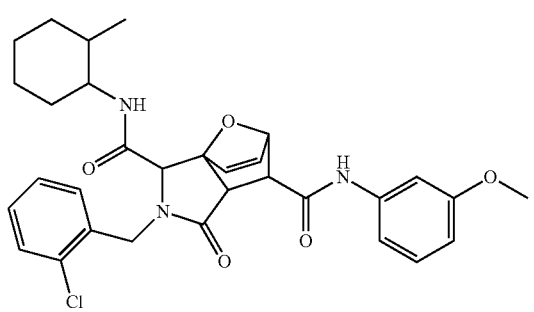
(37)
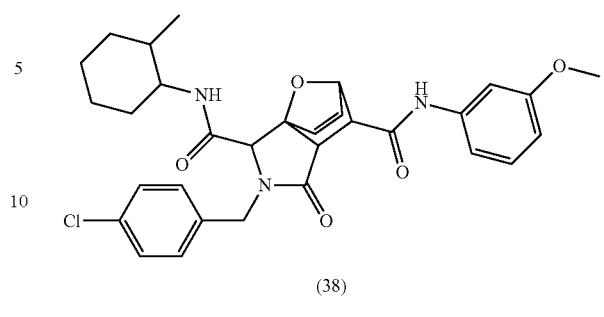
(38)
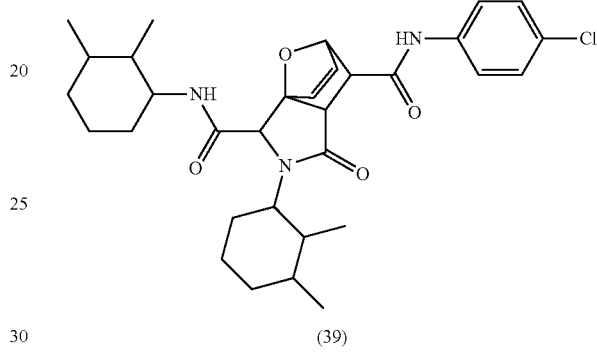
(39)
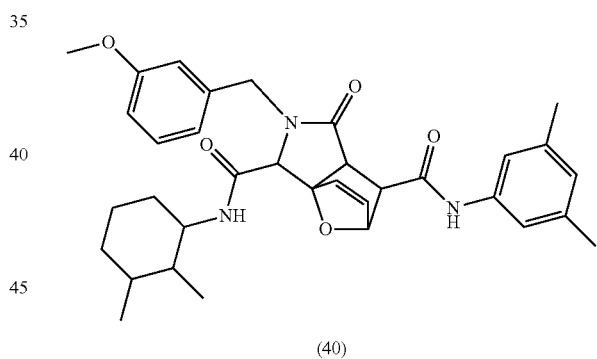
(40)
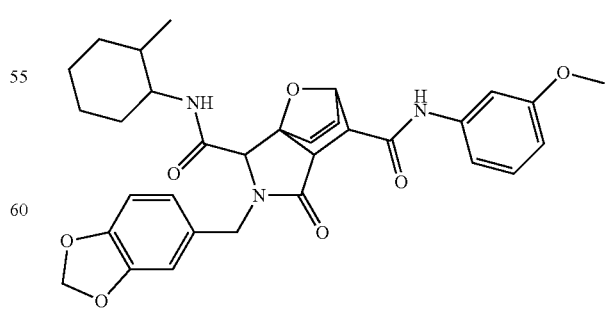
(41)

TABLE 1-continued
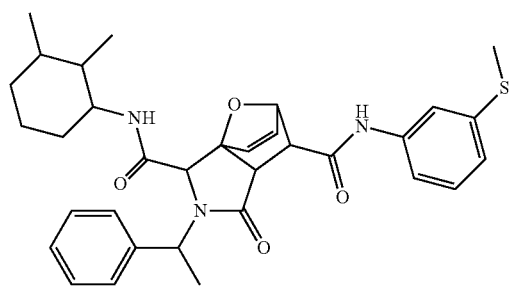
(42)
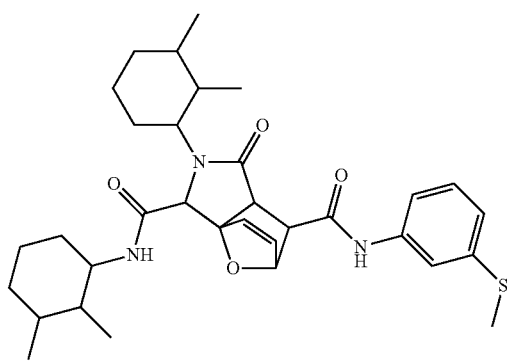
(43)
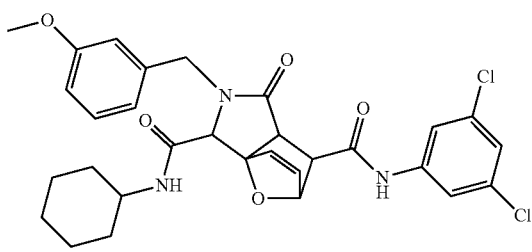
(44)
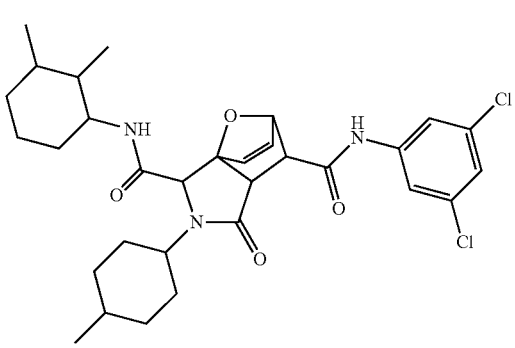
(45)
TABLE 1-continued
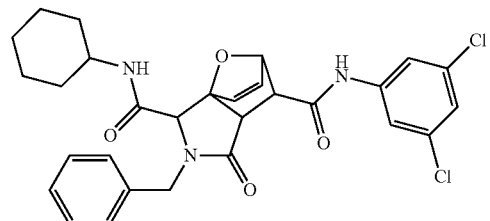
(46)
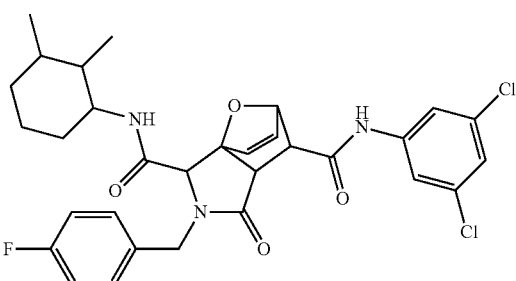
(47)
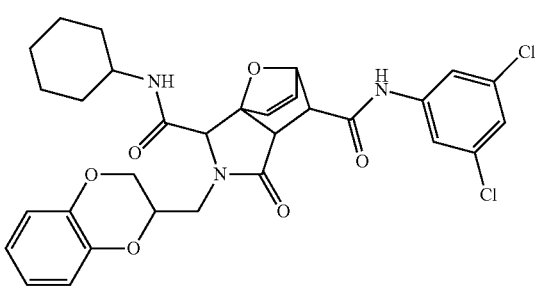
(48)
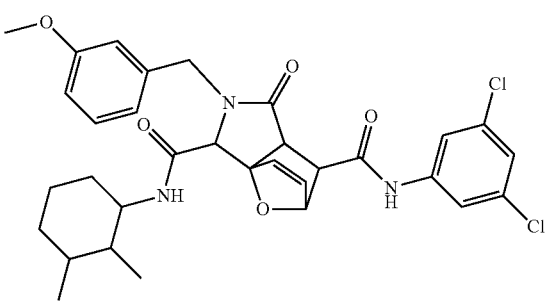 [SMILES: COc1cccc(CN2C(=O)C3C(C(=O)Nc4cc(Cl)cc(Cl)c4)C4C=CC3(O4)C2C(=O)NC2CCCCC2)c1]
(49)
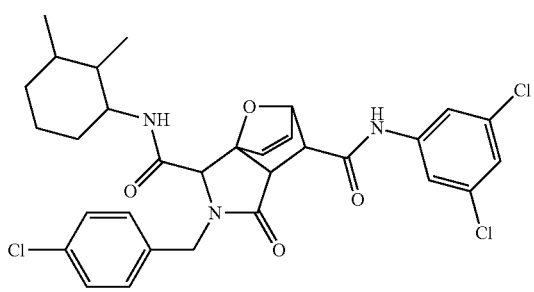
(50)

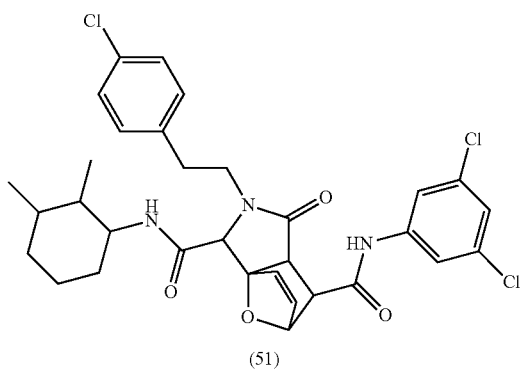 [SMILES: CC1CCCC(NC(=O)C2N(CCc3ccc(Cl)cc3)C(=O)C3C(C(=O)Nc4cc(Cl)cc(Cl)c4)C4C=CC32O4)C1C]

(51)

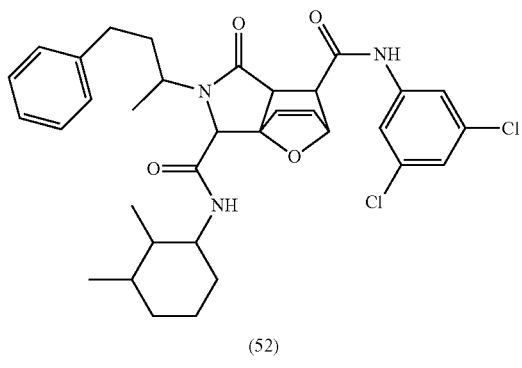 [SMILES: CC1CCCC(NC(=O)C2N(C(C)CCc3ccccc3)C(=O)C3C(C(=O)Nc4cc(Cl)cc(Cl)c4)C4C=CC32O4)C1C]

(52)

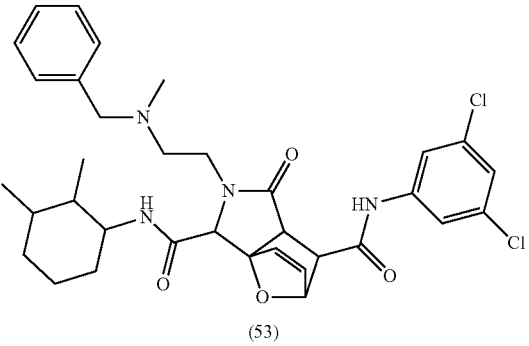 [SMILES: CC1CCCC(NC(=O)C2N(CCN(C)Cc3ccccc3)C(=O)C3C(C(=O)Nc4cc(Cl)cc(Cl)c4)C4C=CC32O4)C1C]

(53)

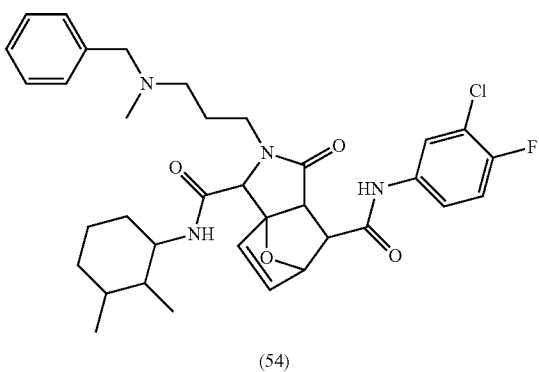 [SMILES: CC1CCCC(NC(=O)C2N(CCCN(C)Cc3ccccc3)C(=O)C3C(C(=O)Nc4ccc(F)c(Cl)c4)C4C=CC32O4)C1C]

(54)

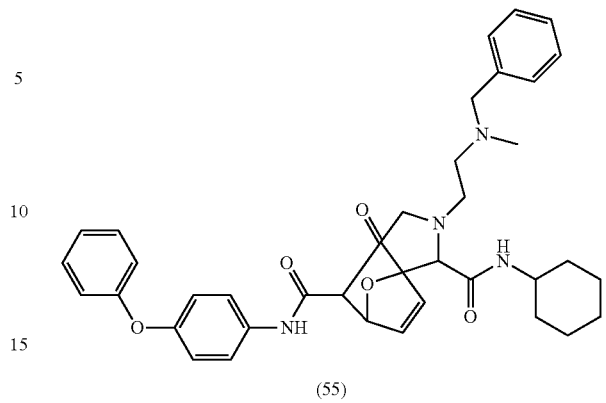

(55)

or the salt, solvate, ester, and/or prodrug thereof.

The above-listed compounds may also be represented by their chemical names as follows:

(1) [6-(2-Methoxy-benzylcarbamoyl)-4-oxo-10-oxa-3-aza-tricyclo[5.2.1.0$^{1,5}$]dec-8-en-3-yl]-acetic acid ethyl ester (2) 3-(4-Methyl-benzyl)-4-oxo-10-oxa-3-aza-tricyclo[5.2.1.0$^{1,5}$]dec-8-ene-6-carboxylic acid 2-chloro-benzylamide (3) 3-[2-(3,4-Dimethoxy-phenyl)-ethyl]-4-oxo-10-oxa-3-aza-tricyclo[5.2.1.0$^{1,5}$]dec-8-ene-6-carboxylic acid cyclopentylamide (4) 4-Oxo-3-thiophen-2-ylmethyl-10-oxa-3-aza-tricyclo[5.2.1.0$^{1,5}$]dec-8-ene-6-carboxylic acid 2,4,6-trifluoro-benzylamide (5) 3-(2-Chloro-benzyl)-4-oxo-10-oxa-3-aza-tricyclo[5.2.1.0$^{1,5}$]dec-8-ene-6-carboxylic acid 2-chloro-benzylamide (6) 1-(2-{[3-(2-Chloro-benzyl)-4-oxo-10-oxa-3-aza-tricyclo[5.2.1.0$^{1,5}$]dec-8-ene-6-carbonyl]-amino}-ethyl)-2,6-dimethyl-piperidinium (7) Diisobutyl-{3-[(4-oxo-3-thiophen-2-ylmethyl-10-oxa-3-aza-tricyclo[5.2.1.0$^{1,5}$]dec-8-ene-6-carbonyl)-amino]-propyl}-ammonium (8) 3-[2-(3,4-Dimethoxy-phenyl)-ethyl]-4-oxo-10-oxa-3-aza-tricyclo[5.2.1.0$^{1,5}$]dec-8-ene-6-carboxylic acid phenethyl-amide (9) 3-(2-Chloro-benzyl)-4-oxo-10-oxa-3-aza-tricyclo[5.2.1.0$^{1,5}$]dec-8-ene-6-carboxylic acid [2-(ethyl-phenyl-amino)-ethyl]-amide

(10) 3-Allyl-4-oxo-10-oxa-3-aza-tricyclo[5.2.1.0$^{1,5}$]dec-8-ene-2,6-dicarboxylic acid 6-[(3-methoxy-phenyl)-amide] 2-[(2-methyl-cyclohexyl)-amide]

(11) 3-[2-(3,4-Dimethoxy-phenyl)-ethyl]-4-oxo-10-oxa-3-aza-tricyclo[5.2.1.0$^{1,5}$]dec-8-ene-6-carboxylic acid 2-chloro-benzylamide

(12) 3-[2-(3,4-Dimethoxy-phenyl)-ethyl]-4-oxo-10-oxa-3-aza-tricyclo[5.2.1.0$^{1,5}$]dec-8-ene-6-carboxylic acid [2-(4-chloro-phenyl)-ethyl]-amide

(13) 3-tert-Butyl-4-oxo-10-oxa-3-aza-tricyclo[5.2.1.0$^{1,5}$] dec-8-ene-2,6-dicarboxylic acid 2-cyclohexylamide 6-[(3-methylsulfanyl-phenyl)-amide]

(14) 4-Oxo-3-propyl-10-oxa-3-aza-tricyclo[5.2.1.0$^{1,5}$]dec-8-ene-2,6-dicarboxylic acid 6-cyclohexylamide 2-[(3,5-dichloro-phenyl)-amide]

(15) 3-Benzyl-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]

(16) 4-Oxo-3-(tetrahydro-furan-2-ylmethyl)-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(17) 3-(4-Methyl-benzyl)-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]

(18) 3-Benzyl-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(19) 4-Oxo-3-pyridin-3-ylmethyl-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(20) 3-(4-Fluoro-benzyl)-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]

(21) 3-(2-Fluoro-benzyl)-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]

(22) 3-(2,3-Dimethyl-cyclohexyl)-4-oxo-10-oxa-3-aza-tricyclo[5.2.1.0$^{1,5}$]dec-8-ene-2,6-dicarboxylic acid 2-[(2-methyl-cyclohexyl)-amide]6-m-tolylamide

(23) 4-Oxo-3-thiophen-2-ylmethyl-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(24) 4-Oxo-3-(tetrahydro-furan-2-ylmethyl)-10-oxa-3-aza-tricyclo[5.2.1.0$^{1,5}$]dec-8-ene-2,6-dicarboxylic acid 6-[(2,3-dimethyl-cyclohexyl)-amide]2-[(3,5-dimethyl-phenyl)-amide]

(25) 2-[2-Cyclohexylcarbamoyl-6-(3-methoxy-phenylcarbamoyl)-4-oxo-10-oxa-3-aza-tricyclo[5.2.1.0$^{1,5}$]dec-8-en-3-ylmethyl]-1-ethyl-pyrrolidinium

(26) 4-Oxo-3-pyridin-3-ylmethyl-10-oxa-3-aza-tricyclo[5.2.1.0$^{1,5}$]dec-8-ene-2,6-dicarboxylic acid 6-[(2,3-dimethyl-cyclohexyl)-amide]2-[(3,5-dimethyl-phenyl)-amide]

(27) 3-(4-Methyl-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(28) 3-(4-Fluoro-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(29) 3-(2-Fluoro-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(30) 3-(4-Chloro-benzyl)-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]

(31) 4-Oxo-3-(tetrahydro-furan-2-ylmethyl)-10-oxa-3-aza-tricyclo[5.2.1.0$^{1,5}$]dec-8-ene-2,6-dicarboxylic acid 6-cyclohexylamide 2-[(3,5-dichloro-phenyl)-amide]

(32) 3-(2-Chloro-benzyl)-4-oxo-10-oxa-3-aza-tricyclo[5.2.1.0$^{1,5}$]dec-8-ene-2,6-dicarboxylic acid 2-cyclohexylamide 6-[(3-methoxy-phenyl)-amide]

(33) 3-Benzo[1,3]dioxol-5-ylmethyl-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]

(34) 3-(4-Methoxy-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(35) 3-(3-Methoxy-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(36) 3-(2-Fluoro-benzyl)-4-oxo-10-oxa-3-aza-tricyclo[5.2.1.0$^{1,5}$]dec-8-ene-2,6-dicarboxylic acid 6-[(2,3-dimethyl-cyclohexyl)-amide]2-[(3,5-dimethyl-phenyl)-amide]

(37) 3-(2-Chloro-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(38) 3-(4-Chloro-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(39) 3-(2,3-Dimethyl-cyclohexyl)-4-oxo-10-oxa-3-aza-tricyclo[5.2.1.0$^{1,5}$]dec-8-ene-2,6-dicarboxylic acid 6-[(4-chloro-phenyl)-amide]2-[(2,3-dimethyl-cyclohexyl)-amide]

(40) 3-(3-Methoxy-benzyl)-4-oxo-10-oxa-3-aza-tricyclo[5.2.1.0$^{1,5}$]dec-8-ene-2,6-dicarboxylic acid 6-[(2,3-dimethyl-cyclohexyl)-amide]2-[(3,5-dimethyl-phenyl)-amide]

(41) 3-Benzo[1,3]dioxol-5-ylmethyl-4-oxo-10-oxa-3-aza-tricyclo[5.2.1.0$^{1,5}$]dee-8-ene-2,6-dicarboxylic acid 6-[(3-methoxy-phenyl)-amide]2-[(2-methyl-cyclohexyl)-amide]

(42) 4-Oxo-3-(1-phenyl-ethyl)-10-oxa-3-aza-tricyclo[5.2.1.0$^{1,5}$]dec-8-ene-2,6-dicarboxylic acid 2-[(2,3-dimethyl-cyclohexyl)-amide]6-[(3-methylsulfanyl-phenyl)amide]

(43) 3-(2,3-Dimethyl-cyclohexyl)-4-oxo-10-oxa-3-aza-tricyclo[5.2.1.0$^{1,5}$]dec-8-ene-2,6-dicarboxylic acid 2-[(2,3-dimethyl-cyclohexyl)-amide]6-[(3-methylsulfanyl-phenyl)-amide]

(44) 3-(3-Methoxy-benzyl)-4-oxo-10-oxa-3-aza-tricyclo[5.2.1.0$^{1,5}$]dec-8-ene-2,6-dicarboxylic acid 6-cyclohexylamide 2-[(3,5-dichloro-phenyl)-amide]

(45) 3-(4-Methyl-cyclohexyl)-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(46) 3-(2-Chloro-benzyl)-4-oxo-10-oxa-3-aza-tricyclo[5.2.1.0$^{1,5}$]dec-8-ene-2,6-dicarboxylic acid 6-cyclohexylamide 2-[(3,5-dichloro-phenyl)-amide]

(47) 3-(4-Fluoro-benzyl)-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(48) 3-(2,3-Dihydro-benzo[1,4]dioxin-2-ylmethyl)-4-oxo-10-oxa-3-aza-tricyclo[5.2.1.0$^{1,5}$]dec-8-ene-2,6-dicarboxylic acid 6-cyclohexylamide 2-[(3,5-dichloro-phenyl)-amide]

(49) 3-(3-Methoxy-benzyl)-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(50) 3-(4-Chloro-benzyl)-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(51) 3-[2-(4-Chloro-phenyl)-ethyl]-4-oxo-10-oxa-3-aza-tricyclo[5.2.1.0$^{1,5}$]dec-8-ene-2,6-dicarboxylic acid 2-[(3,5-dichloro-phenyl)amide]6-[(2,3-dimethyl-cyclohexyl)-amide]

(52) 3-(1-Methyl-3-phenyl-propyl)-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(53) 3-[2-(Benzyl-methyl-amino)-ethyl]-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(54) 3-[3-(Benzyl-methyl-amino)-propyl]-4-oxo-10-oxa-3-aza-tricyclo[5.2.1.0^{1,5}]dec-8-ene-2,6-dicarboxylic acid 6-[(3-chloro-4-fluoro-phenyl)-amide]2-[(2,3-dimethyl-cyclohexyl)-amide]

(55) 3-[2-(Benzyl-methyl-amino)-ethyl]-4-oxo-10-oxa-3-aza-tricyclo[5.2.1.0^{1,5}]dec-8-ene-2,6-dicarboxylic acid 2-cyclohexylamide 6-[(4-phenoxy-phenyl)-amide].

In one embodiment of formula (I), when $R^3$ is —CONR$^{17}$R$^{18}$ and $R^2$ is hydrogen or —CONR$^{15}$R$^{16}$, $R^1$ is not alkyl, substituted alkyl, arylalkyl, substituted arylalkyl, heteroarylalkyl or cycloheteroalkylalkyl.

In one embodiment of formula (I), $R^3$ is —CONR$^{17}$R$^{18}$, $R^{17}$ is hydrogen, $R^{18}$ is substituted alkyl, arylalkyl, substituted arylalkyl, heteroaryl, heteroalkyl or substituted aryl or $R^2$ is hydrogen or —CONR$^{15}$R$^{16}$, $R^{15}$ is hydrogen, $R^{16}$ is cycloalkyl or substituted cycloalkyl, $R^1$ is not alkyl, substituted alkyl, arylalkyl, substituted arylalkyl, heteroarylalkyl or cycloheteroalkylalkyl.

In one embodiment of formula (I), at least two of $R^1$, $R^2$ and $R^3$ are not hydrogen.

In one embodiment of formula (I), X is —N— and Y is O.

In one embodiment of formula (I), X is —N—, Y is O and Z is —O—

In one embodiment of formula (I), X is —N—, Y is O, Z is —O— and n is 0.

In one embodiment of formula (I), X is —N—, Y is O, Z is —O— A-B is CR$^4$=CR$^5$ and n is 0.

In one embodiment of formula (I), X is —N—, Y is O, Z is —O— and n is 1.

In one embodiment of formula (I), X is —N—, Y is O, Z is —O— A-B is CR$^4$=CR$^5$ and n is 1.

In one embodiment of formula (I), $R^3$ and $R^1$ are not hydrogen.

In one embodiment of formula (I), X is —N—, Y is O, Z is —O—, and $R^3$ and $R^1$ are not hydrogen.

In one embodiment of formula (I), $R^3$ is —CONR$^{17}$R$^{18}$, acyl, substituted acyl, alkoxycarbonyl, substituted alkoxycarbonyl, aryloxycarbonyl or substituted aryloxycarbonyl and $R^2$ is hydrogen or —CONR$^{15}$R$^{16}$, acyl, substituted acyl, alkoxycarbonyl, substituted alkoxycarbonyl, aryloxycarbonyl or substituted aryloxycarbonyl.

In one embodiment of formula (I), $R^3$ is —CONR$^{17}$R$^{18}$ and $R^2$ is hydrogen or —CONR$^{15}$R$^{16}$.

In one embodiment of formula (I), X is —N—, Y is O, Z is —O—, $R^3$ is —CONR$^{17}$R$^{18}$, acyl, substituted acyl, alkoxycarbonyl, substituted alkoxycarbonyl and $R^2$ is hydrogen or —CONR$^{15}$R$^{16}$, acyl, substituted acyl, alkoxycarbonyl or substituted alkoxycarbonyl.

In one embodiment of formula (I), X is —N—, Y is O, Z is —O—, $R^3$ is —CONR$^{17}$R$^{18}$, acyl, substituted acyl, alkoxycarbonyl, substituted alkoxycarbonyl, $R^2$ is hydrogen or —CONR$^{15}$R$^{16}$, acyl, substituted acyl, alkoxycarbonyl or substituted alkoxycarbonyl and $R^1$ is not hydrogen.

In one embodiment of formula (I), $R^4$ and $R^5$ are hydrogen, alkyl or aryl.

In one embodiment of formula (I), $R^4$ and $R^5$ are hydrogen.

In one embodiment of formula (I), $R^6$, $R^7$, $R^8$, $R^9$, $R^{10}$, $R^{11}$, and $R^{12}$ are independently hydrogen, alkyl, aryl or arylalkyl.

In one embodiment of the present invention, the compound having a structural formula (I) is selected from the group consisting of

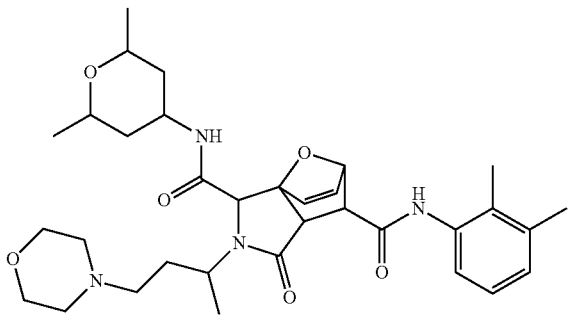

(56)

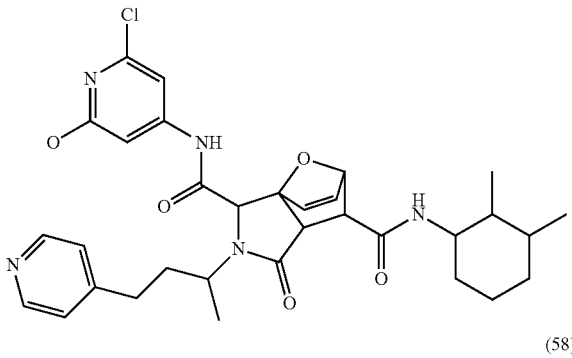

(57)

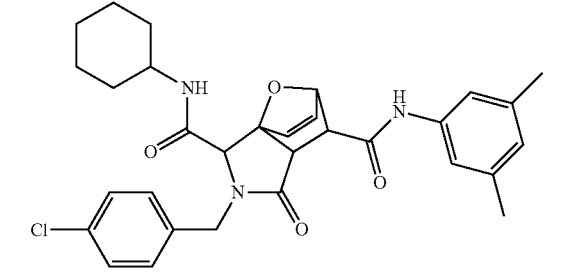

(58)

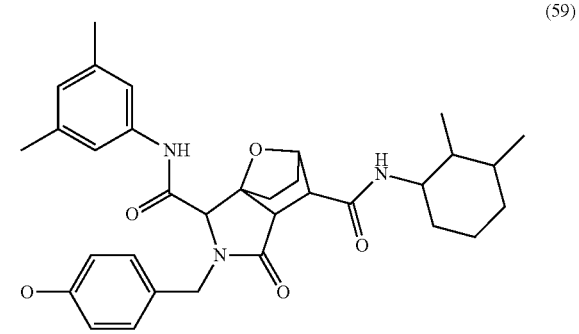

(59)

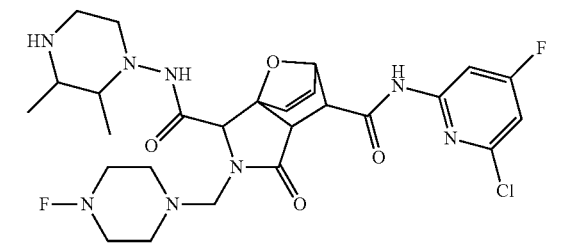

(60)

(61) 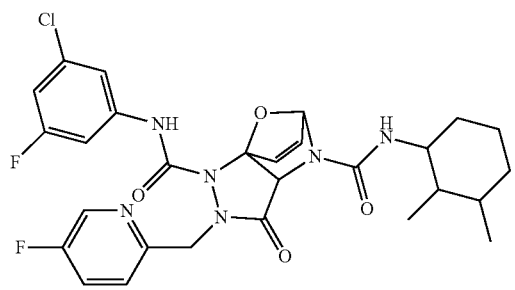

(62) 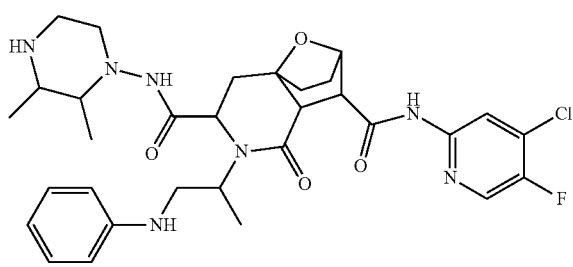

(63) 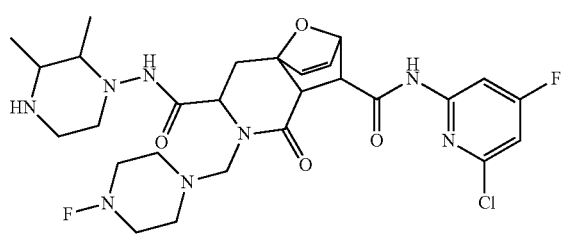

(64) 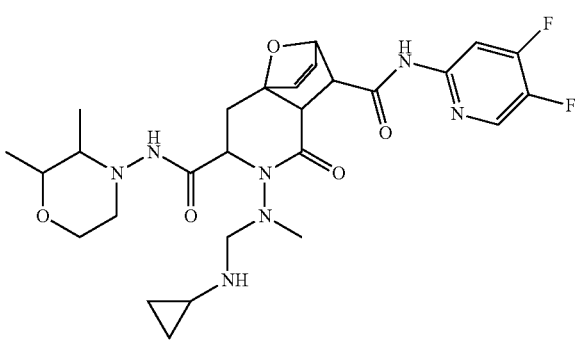

(65) 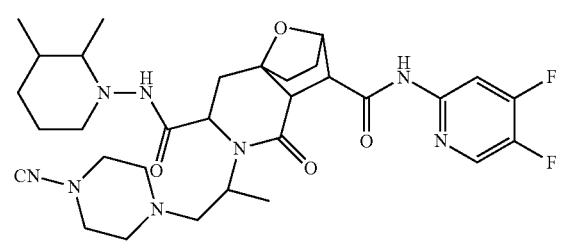

(66) 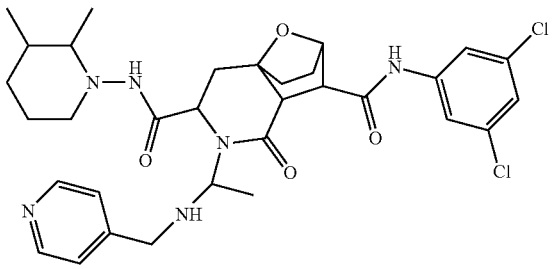

or the salt, solvate, ester, and/or prodrug thereof.

The above-listed compounds may also be represented by their chemical names as follows:

(56) 3-(1-Methyl-3-morpholin-4-yl-propyl)-4-oxo-10-oxa-3-aza-tricyclo[5.2.1.0$^{1,5}$]dec-8-ene-2,6-dicarboxylic acid 6-[(2,6-dichloro-tetrahydro-pyran-4-yl)-amide]2-[(2,3-dimethyl-phenyl)-amide]

(57) 3-(1-Methyl-3-pyridin-4-yl-propyl)-4-oxo-10-oxa-3-aza-tricyclo[5.2.1.0$^{1,5}$]decane-2,6-dicarboxylic acid 6-[(2,6-dichloro-pyridin-4-yl)-amide]2-[(2,3-dimethyl-cyclohexyl)-amide]

(58) 3-(4-Chloro-benzyl)-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]

(59) 3-(4-Chloro-benzyl)-4-oxo-10-oxa-3-aza-tricyclo[5.2.1.0$^{1,5}$]decane-2,6-dicarboxylic acid 6-[(3,5-dichloro-phenyl)-amide]2-[(2,3-dimethyl-cyclohexyl)-amide]

(60) 3-(4-Fluoro-piperazin-1-ylmethyl)-4-oxo-10-oxa-3-aza-tricyclo[5.2.1.0$^{1,5}$]dec-8-ene-2,6-dicarboxylic acid 6-[(6-chloro-4-fluoro-pyridin-2-yl)-amide]2-[(2,3-dimethyl-piperazin-1-yl)-amide]

(61) 3-(5-Fluoro-pyridin-2-ylmethyl)-4-oxo-10-oxa-2,3,6-triaza-tricyclo[5.2.1.0$^{1,5}$]dec-8-ene-2,6-dicarboxylic acid 6-[(3-chloro-5-fluoro-phenyl)-amide]2-[(2,3-dimethyl-cyclohexyl)-amide]

(62) 4-(1-Methyl-2-phenylamino-ethyl)-5-oxo-11-oxa-4-aza-tricyclo[6.2.1.0$^{1,6}$]undecane-3,7-dicarboxylic acid 7-[(4-chloro-5-fluoro-pyridin-2-yl)-amide]3-[(2,3-dimethyl-piperazin-1-yl)-amide]

(63) 4-(4-Fluoro-piperazin-1-ylmethyl)-5-oxo-11-oxa-4-aza-tricyclo[6.2.1.0$^{1,6}$]undec-9-ene-3,7-dicarboxylic acid 7-[(6-chloro-4-fluoro-pyridin-2-yl)-amide]3-[(2,3-dimethyl-piperazin-1-yl)-amide]

(64) 4-(Cyclopropylaminomethyl-methyl-amino)-5-oxo-11-oxa-4-aza-tricyclo[6.2.1.0$^{1,6}$]undec-9-ene-3,7-dicarboxylic acid 7-[(4,5-difluoro-pyridin-2-yl)-amide]3-[(2,3-dimethyl-morpholin-4-yl)-amide]

(65) 4-[2-(4-Chloro-piperazin-1-yl)-1-methyl-ethyl]-5-oxo-11-oxa-4-aza-tricyclo[6.2.1.0$^{1,6}$]undecane-3,7-dicarboxylic acid 7-[(4,5-difluoro-pyridin-2-yl)-amide]3-[(2,3-dimethyl-piperazin-1-yl)-amide]

(66) 5-Oxo-4-{1-[(pyridin-4-ylmethyl)-amino]-ethyl}-11-oxa-4-aza-tricyclo[6.2.1.0$^{1,6}$]undecane-3,7-dicarboxylic acid 7-[(3,5-dichloro-phenyl)-amide]3-[(2,3-dimethyl-piperidin-1-yl)-amide]

In another aspect, the present invention provides a pharmaceutical composition comprising a compound having a structural Formula (I), or a salt, solvate, ester, and/or prodrug thereof:

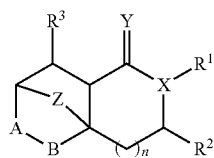

(I)

wherein:
A-B is —CHR⁴CHR⁵— or —CR⁴═CR⁵—;
X is —CR⁶— or —N—;
Y is O, NR⁷, or S;
Z is —O—, —NR⁹—, —S—, or —CR¹¹R¹²—;
n is 0 or 1;
$R^1$ is hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;
$R^2$ is hydrogen, acyl, substituted acyl, alkoxycarbonyl, substituted alkoxycarbonyl, aryloxycarbonyl, substituted aryloxycarbonyl, —CONR¹⁵R¹⁶, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;
$R^3$ is hydrogen, acyl, substituted acyl, alkoxycarbonyl, substituted alkoxycarbonyl, aryloxycarbonyl, substituted aryloxycarbonyl, —CONR¹⁷R¹⁸, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;
$R^4$, $R^5$, $R^6$, $R^7$, $R^8$, $R^9$, $R^{10}$, $R^{11}$, and $R^{12}$ are independently hydrogen, alkyl, substituted alkyl, aryl, substituted aryl, arylalkyl or substituted arylalkyl;
$R^{15}$ and $R^{16}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, $R^{15}$ and $R^{16}$, taken together with the nitrogen atom to which they are attached, form a 4-, 5-, 6- or 7-membered cycloheteroalkyl ring, provided that both $R^{15}$ and $R^{16}$ are not hydrogen; and
$R^{17}$ and $R^{18}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively, $R^{15}$ and $R^{16}$, taken together with the nitrogen atom to which they are attached, form a 4-, 5-, 6- or 7-membered cycloheteroalkyl ring, provided that both $R^{15}$ and $R^{16}$ are not hydrogen;
with the proviso that at least one of $R^1$, $R^2$ and $R^3$ is not hydrogen; and
a pharmaceutically acceptable vehicle.

In one embodiment of the pharmaceutical composition, X is —N—, Y is O, Z is —O—, A-B is —CR⁴═CR⁵— and n is 0.

In one embodiment of the pharmaceutical composition, X is —N—, Y is O, Z is —O—, A-B is —CR⁴═CR⁵—, n is 0 and $R^3$ and $R^1$ are not hydrogen.

In one embodiment of the pharmaceutical composition, X is —N—, Y is O, Z is —O— and n is 1.

In one embodiment of the pharmaceutical composition, X is —N—, Y is O, Z is —O— A-B is —CR⁴═CR⁵— and n is 1.

In one embodiment of the pharmaceutical composition, X is —N—, Y is O, Z is —O—, A-B is —CR⁴═CR⁵—, n is 0, $R^3$ is —CONR¹⁷R¹⁸, acyl, substituted acyl, alkoxycarbonyl, substituted alkoxycarbonyl and $R^2$ is hydrogen or —CONR¹⁵R¹⁶, acyl, substituted acyl, alkoxycarbonyl or substituted alkoxycarbonyl.

In one embodiment of the pharmaceutical composition, X is —N—, Y is O, Z is —O—, A-B is —CR⁴═CR⁵—, n is 0, $R^3$ is —CONR¹⁷R¹⁸, and $R^2$ is hydrogen or —CONR¹⁵R¹⁶.

In one embodiment of the pharmaceutical composition, X is —N—, Y is O, Z is —O—, A-B is —CR⁴═CR⁵—, n is 0, $R^3$ is —CONR¹⁷R¹⁸, $R^{17}$ is hydrogen, $R^2$ is hydrogen or —CONR¹⁵R¹⁶ and $R^{15}$ is hydrogen.

In one embodiment of the pharmaceutical composition, X is —N—, Y is O, Z is —O—, A-B is —CR⁴═CR⁵—, n is 0, $R^3$ is —CONR¹⁷R¹⁸, $R^{17}$ is hydrogen, $R^2$ is hydrogen or —CONR¹⁵R¹⁶, $R^{15}$ is hydrogen and $R^1$ is not hydrogen.

In one embodiment of the pharmaceutical composition, X is —N—, Y is O, Z is —O—, A-B is —CR⁴═CR⁵—, n is 0, $R^3$ is —CONR¹⁷R¹⁸, $R^{17}$ is hydrogen, $R^2$ is hydrogen or —CONR¹⁵R¹⁶, $R^{15}$ is hydrogen and $R^1$ is alkyl, substituted alkyl, arylalkyl, substituted arylalkyl, heteroarylalkyl or cycloheteroalkylalkyl.

In one embodiment of the pharmaceutical composition, X is —N—, Y is O, Z is —O—, A-B is —CR⁴═CR⁵—, n is 0, $R^3$ is —CONR¹⁷R¹⁸, $R^{17}$ is hydrogen, $R^{18}$ is substituted alkyl, arylalkyl, substituted arylalkyl, heteroaryl, heteroalkyl or substituted aryl or $R^2$ is hydrogen or —CONR¹⁵R¹⁶, $R^{15}$ is hydrogen, $R^{16}$ is cycloalkyl or substituted cycloalkyl, $R^1$ is alkyl, substituted alkyl, arylalkyl, substituted arylalkyl, substituted heteroarylalkyl, cycloheteroalkylalkyl or substituted cycloheteroalkylalkyl.

In one embodiment of the pharmaceutical composition, the compound having a structural Formula (I) is selected from the group consisting of

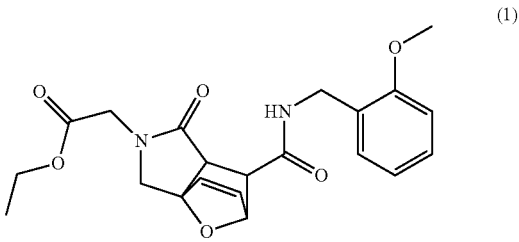

(1)

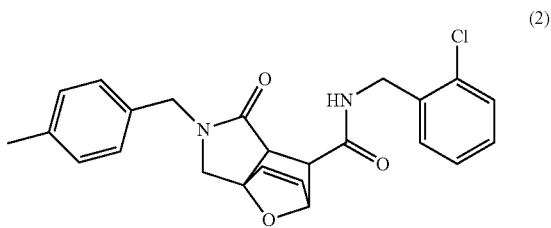

(2)

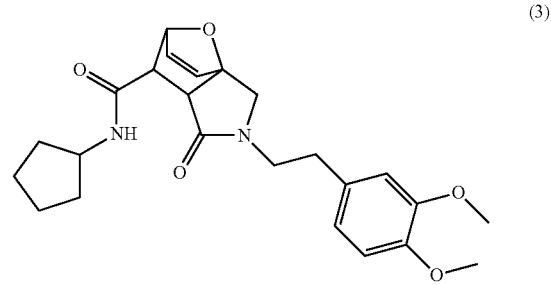

(3)

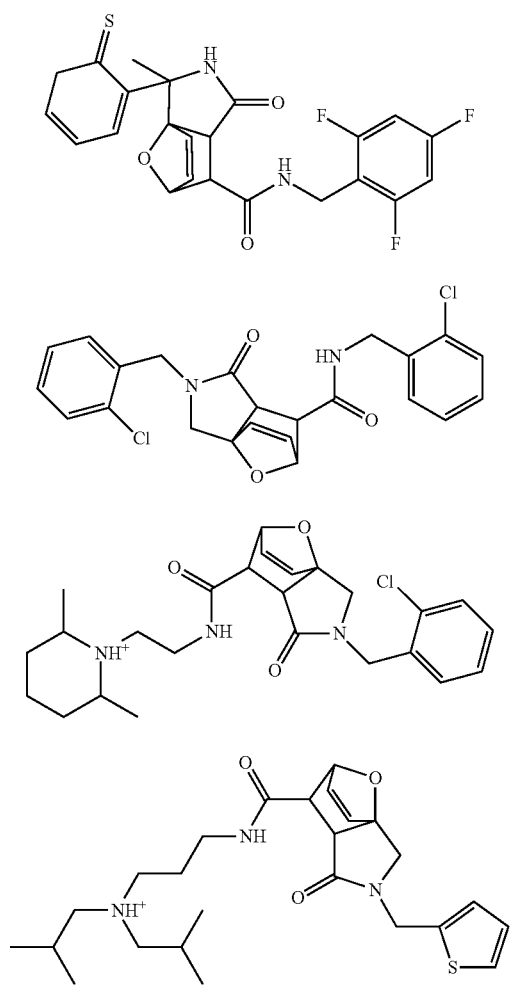
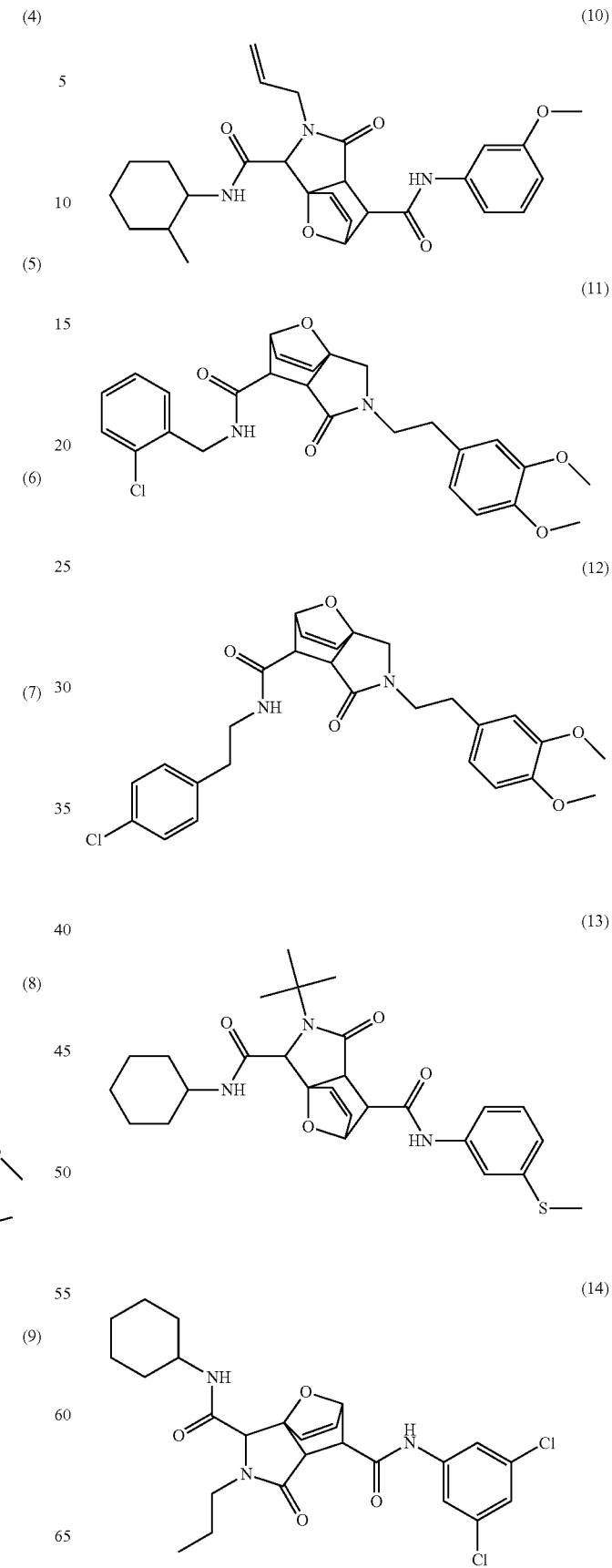

(15)
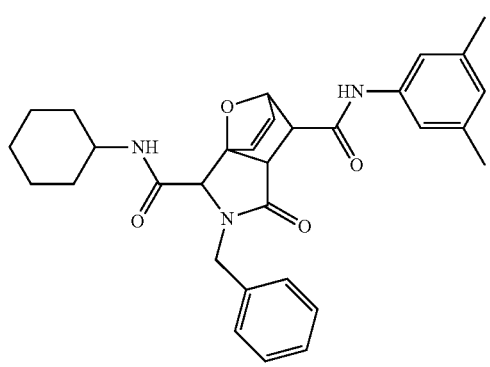
(16)
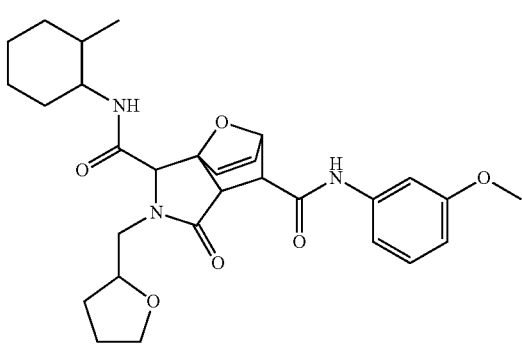
(17)
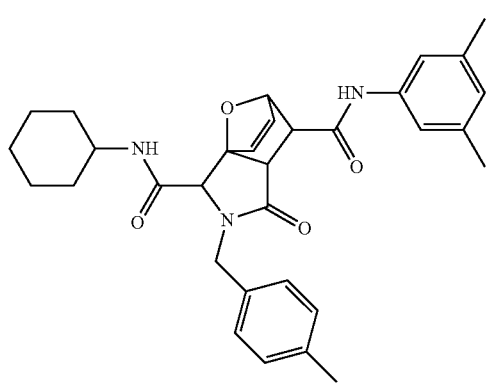
(18)
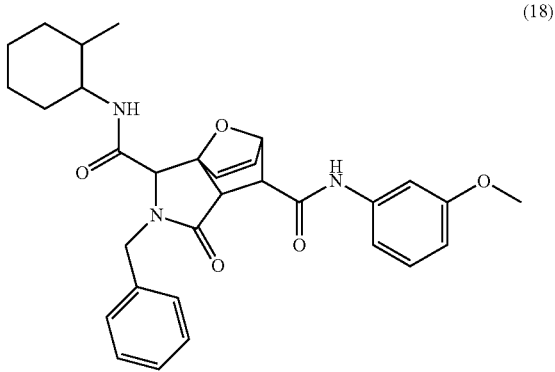
(19)
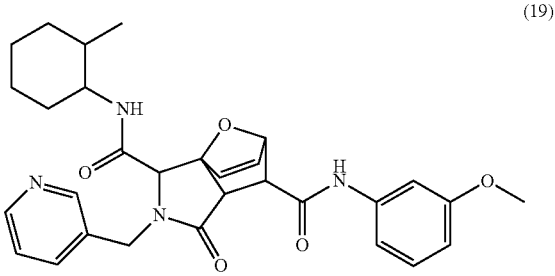
(20)
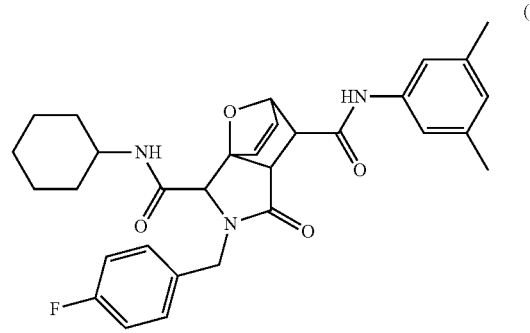
(21)
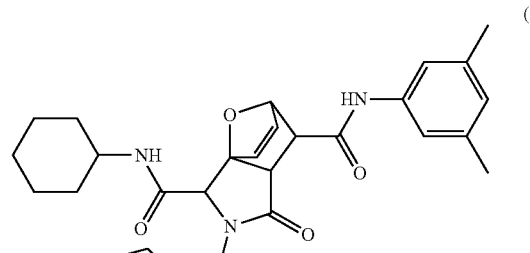
(22)
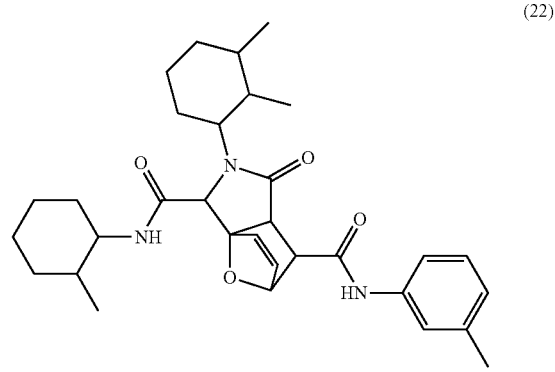
(23)
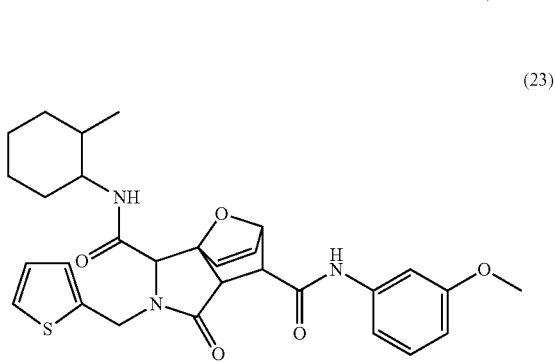

-continued
(24)
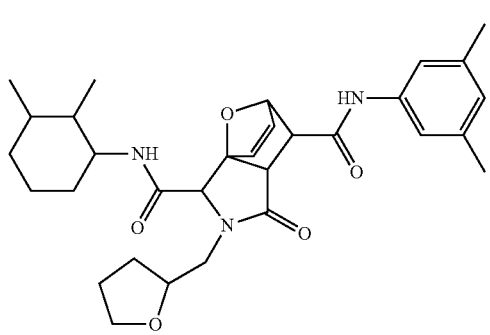
(25)
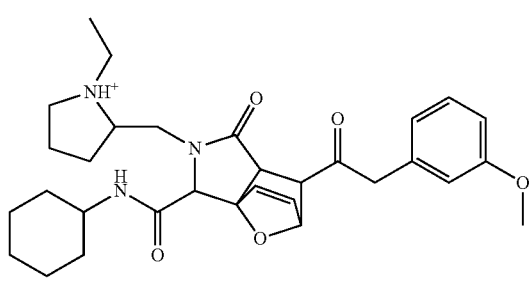
(26)
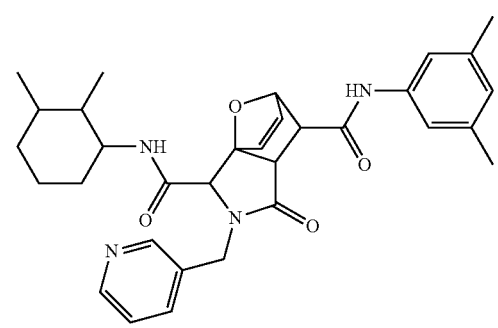
(27)
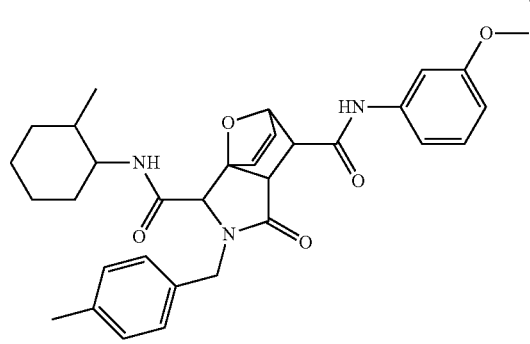
(28)
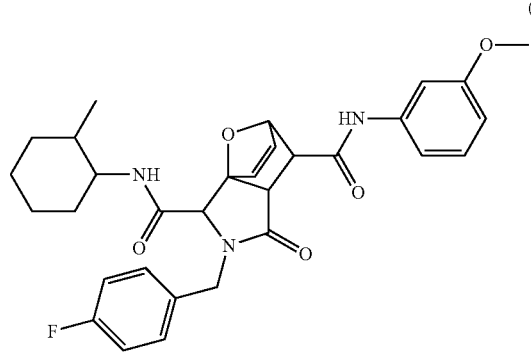
-continued
(29)
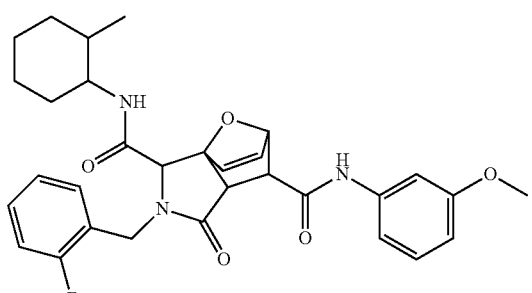
(30)
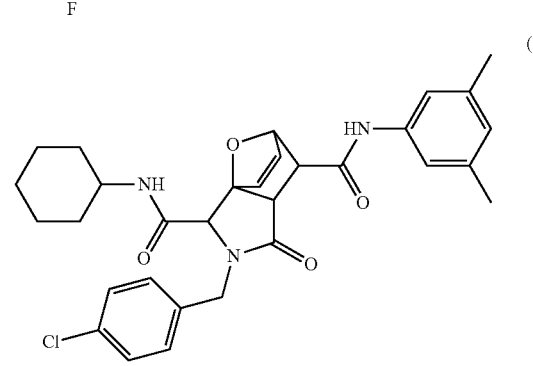
(31)
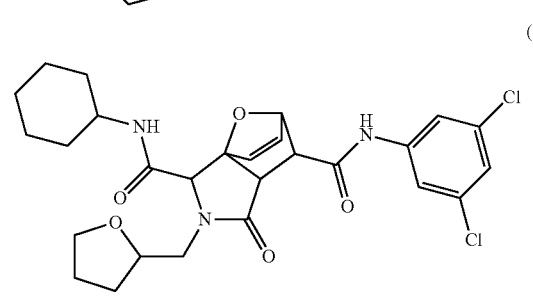
(32)
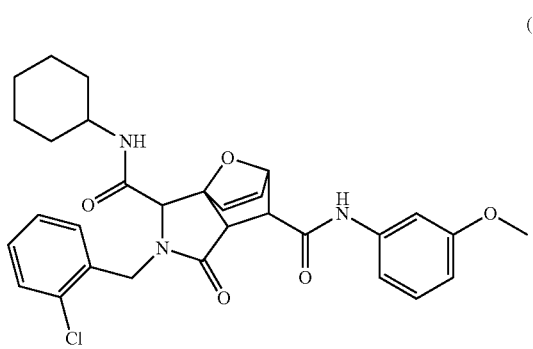
(33)
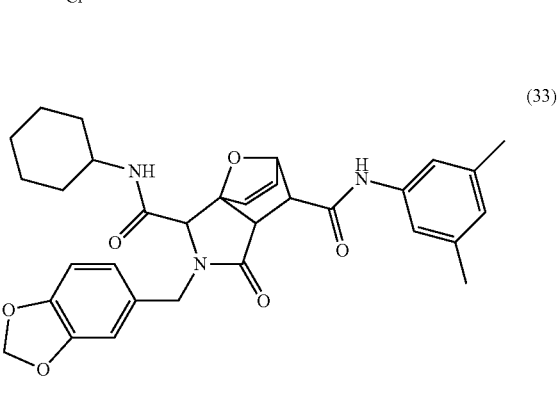

(34)
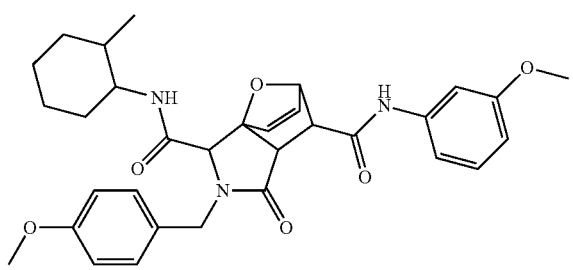
(35)
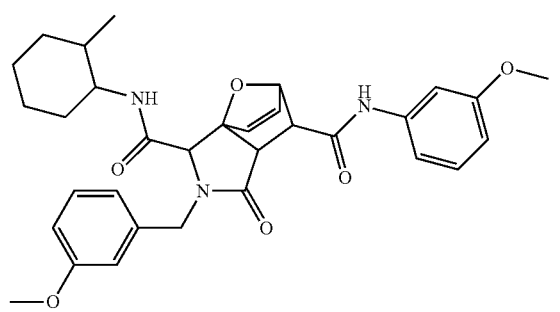
(36)
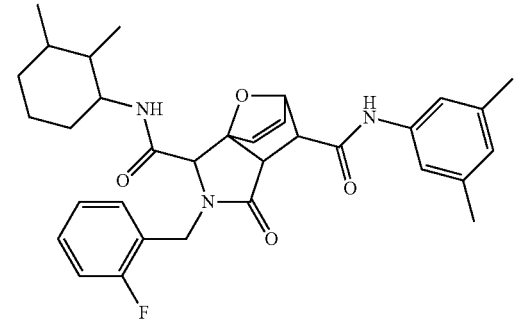
(37)
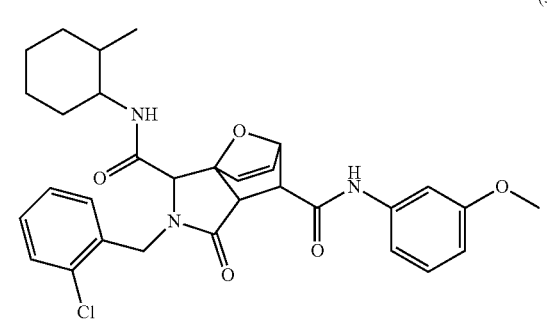
(38)
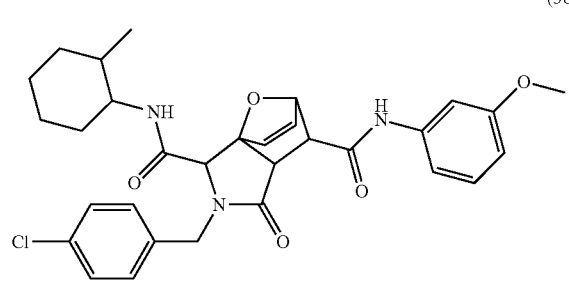
(39)
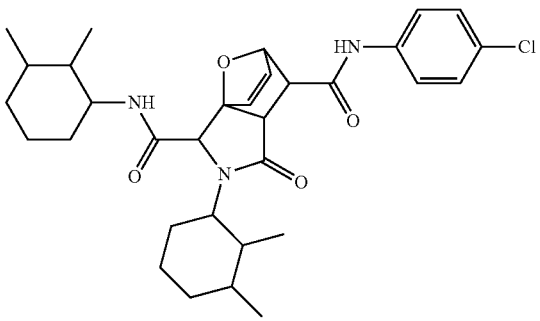
(40)
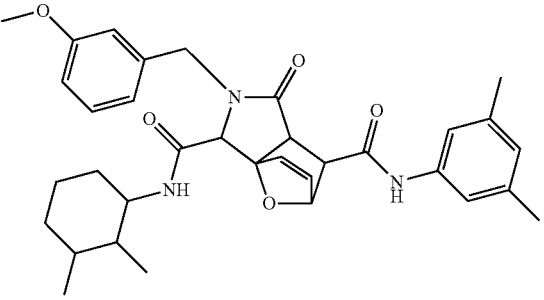
(41)
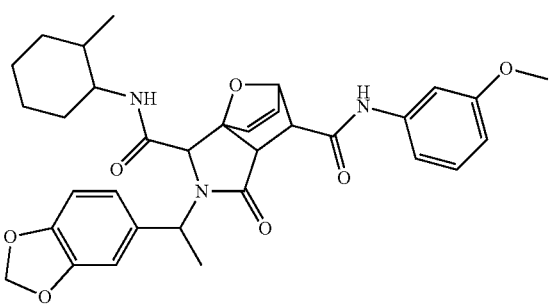
(42)
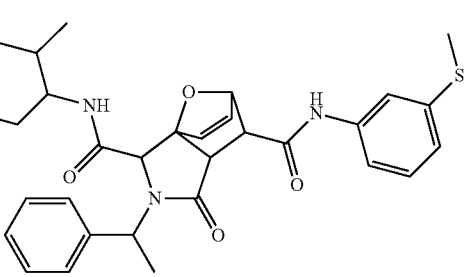
(43)
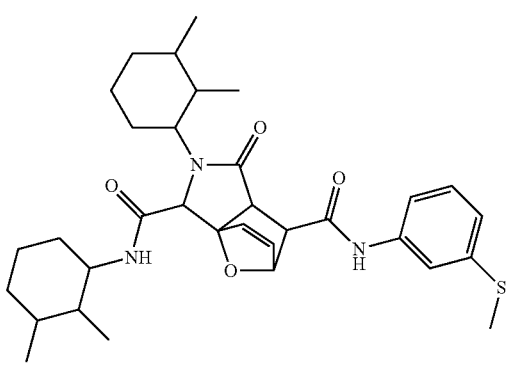

-continued
(44)
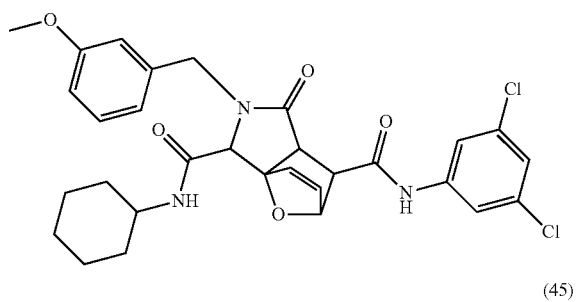
(45)
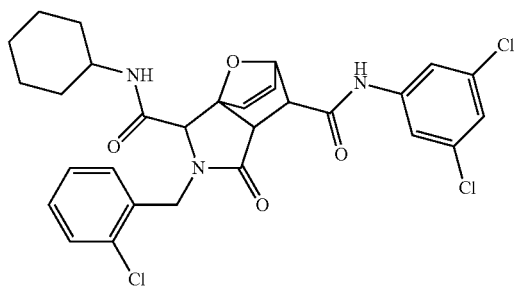
(46)
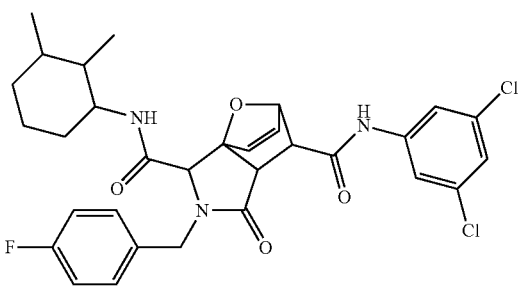
(47)
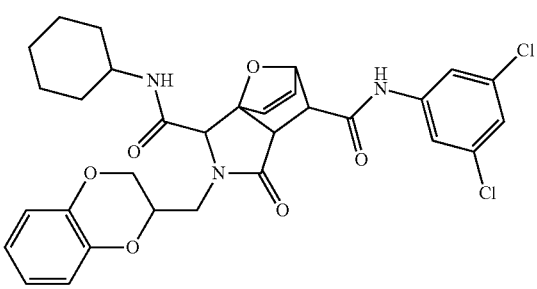
(48)
-continued
(49)
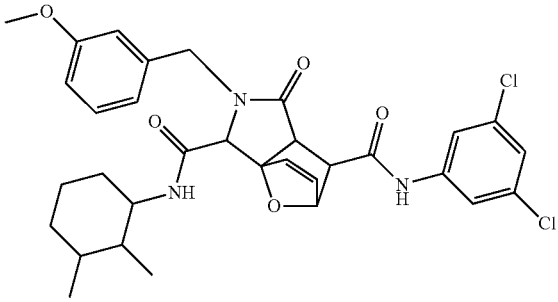
(50)
(51)
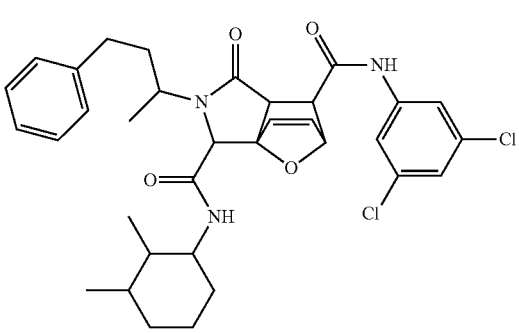
(52)
(53)
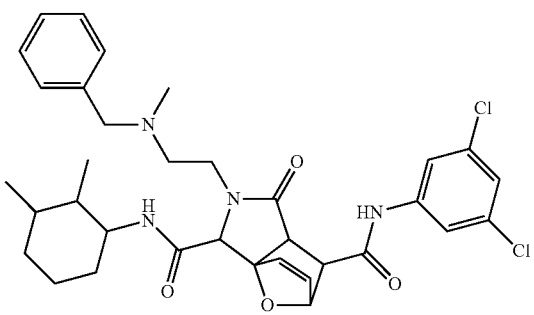

(54)
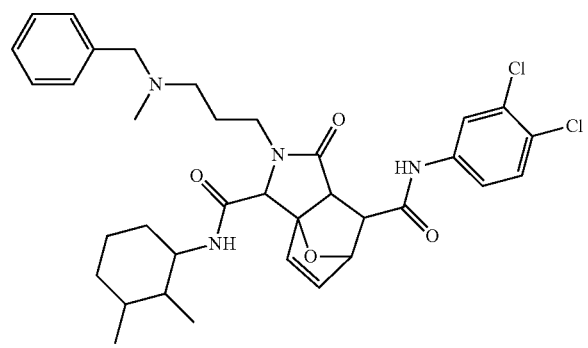
(55)
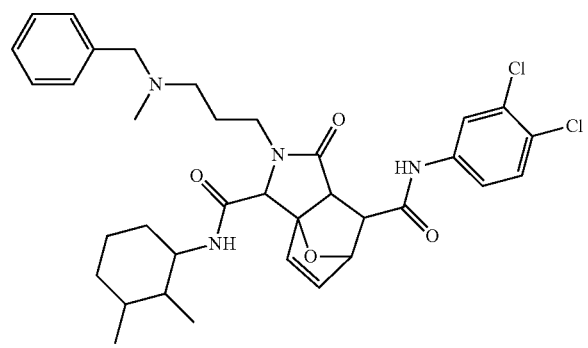
(50)
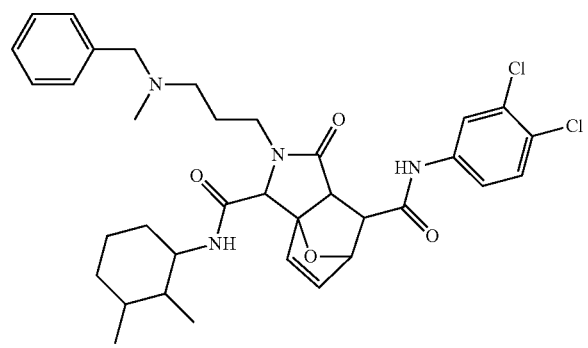
(51)
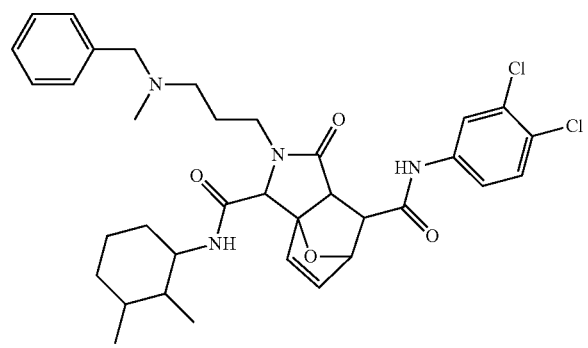
(52)
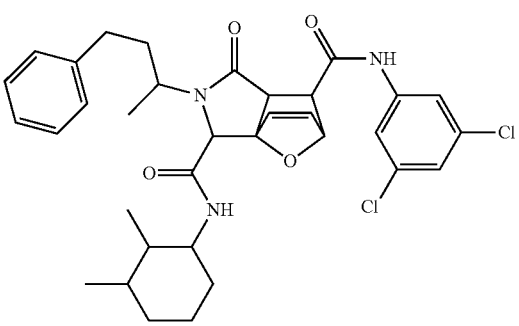
(53)
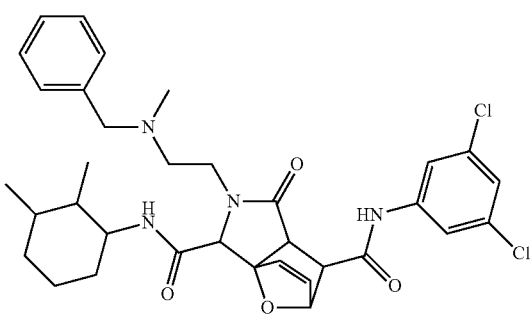
(54)
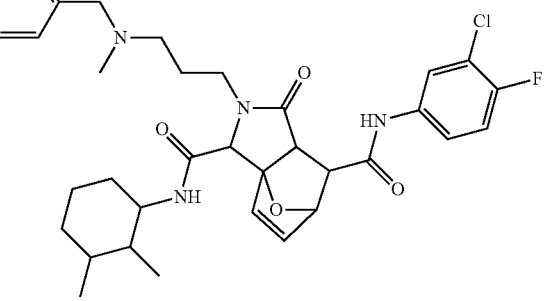
(55)
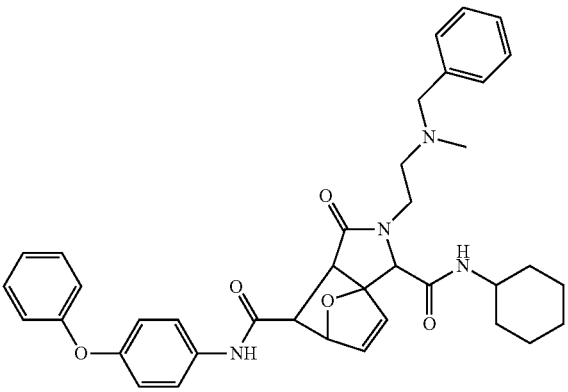

(56)
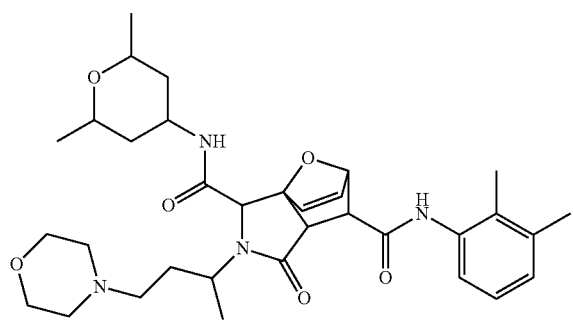
(57)
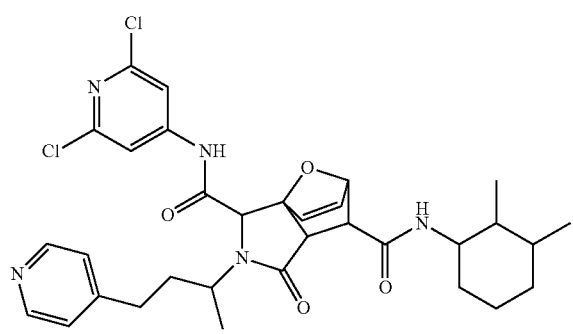
(58)
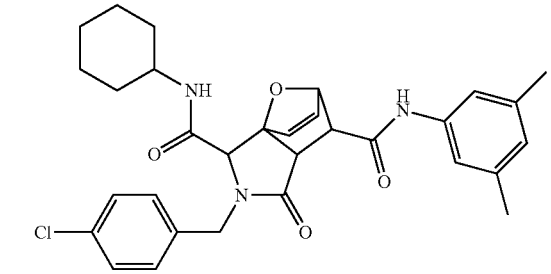
(59)
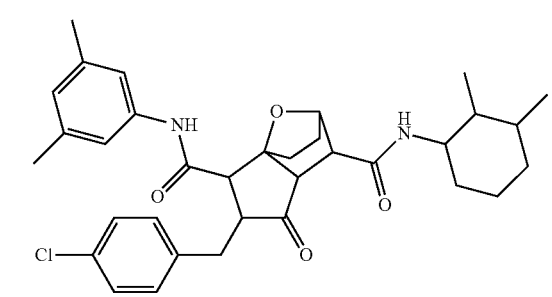
(60)
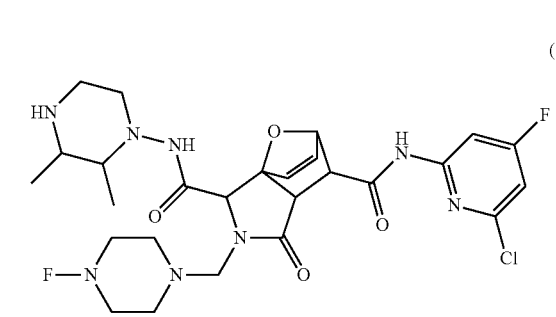
(61)
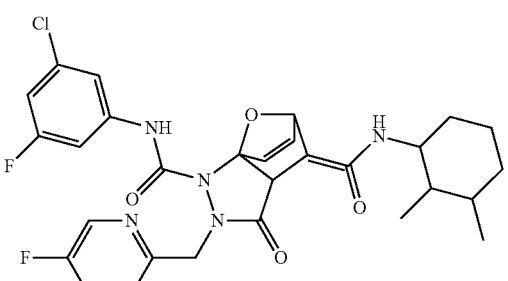
(62)
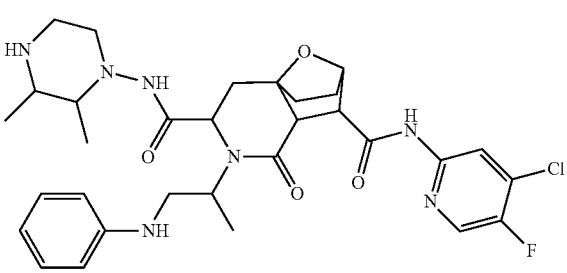
(63)
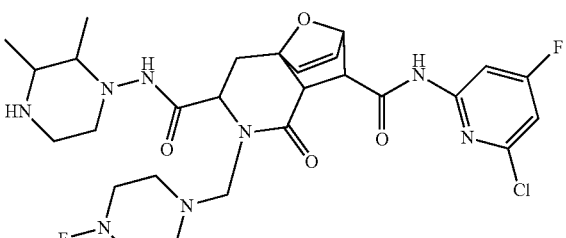
(64)
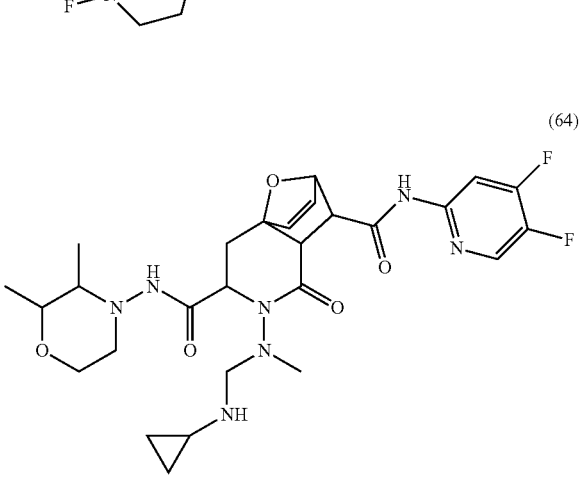
(65)
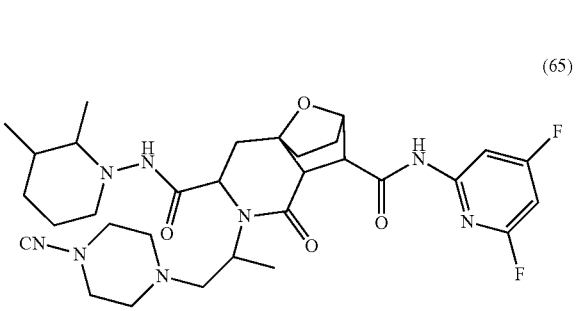

-continued (66)

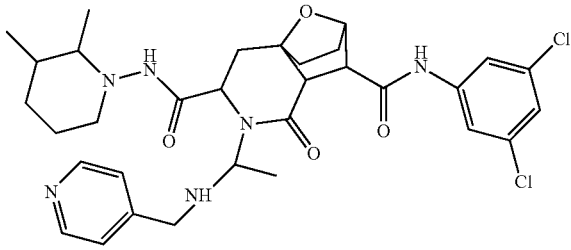

or the salt, solvate, ester, and/or prodrug thereof.

The above-listed compounds may also be represented by their chemical names as follows:

(1) [6-(2-Methoxy-benzylcarbamoyl)-4-oxo-10-oxa-3-aza-tricyclo[5.2.1.0$^{1,5}$]dec-8-en-3-yl]-acetic acid ethyl ester
(2) 3-(4-Methyl-benzyl)-4-oxo-10-oxa-3-aza-tricyclo[5.2.1.0$^{1,5}$]dec-8-ene-6-carboxylic acid 2-chloro-benzylamide
(3) 3-[2-(3,4-Dimethoxy-phenyl)-ethyl]-4-oxo-10-oxa-3-aza-tricyclo[5.2.1.0$^{1,5}$]dec-8-ene-6-carboxylic acid cyclopentylamide
(4) 4-Oxo-3-thiophen-2-ylmethyl-10-oxa-3-aza-tricyclo[5.2.1.0$^{1,5}$]dec-8-ene-6-carboxylic acid 2,4,6-trifluoro-benzylamide
(5) 3-(2-Chloro-benzyl)-4-oxo-10-oxa-3-aza-tricyclo[5.2.1.0$^{1,5}$]dec-8-ene-6-carboxylic acid 2-chloro-benzylamide
(6) 1-(2-{[3-(2-Chloro-benzyl)-4-oxo-10-oxa-3-aza-tricyclo[5.2.1.0$^{1,5}$]dec-8-ene-6-carbonyl]-amino}-ethyl)-2,6-dimethyl-piperidinium
(7) Diisobutyl-{3-[(4-oxo-3-thiophen-2-ylmethyl-10-oxa-3-aza-tricyclo[5.2.1.0$^{1,5}$]dec-8-ene-6-carbonyl)-amino]propyl}-ammonium
(8) 3-[2-(3,4-Dimethoxy-phenyl)-ethyl]-4-oxo-10-oxa-3-aza-tricyclo[5.2.1.0$^{1,5}$]dec-8-ene-6-carboxylic acid phenethyl-amide
(9) 3-(2-Chloro-benzyl)-4-oxo-10-oxa-3-aza-tricyclo[5.2.1.0$^{1,5}$]dec-8-ene-6-carboxylic acid [2-(ethyl-phenyl-amino)-ethyl]-amide
(10) 3-Allyl-4-oxo-10-oxa-3-aza-tricyclo[5.2.1.0$^{1,5}$]dec-8-ene-2,6-dicarboxylic acid 6-[(3-methoxy-phenyl)-amide] 2-[(2-methyl-cyclohexyl)-amide]
(11) 3-[2-(3,4-Dimethoxy-phenyl)-ethyl]-4-oxo-10-oxa-3-aza-tricyclo[5.2.1.0$^{1,5}$]dec-8-ene-6-carboxylic acid 2-chloro-benzylamide
(12) 3-[2-(3,4-Dimethoxy-phenyl)-ethyl]-4-oxo-10-oxa-3-aza-tricyclo[5.2.1.0$^{1,5}$]dec-8-ene-6-carboxylic acid [2-(4-chloro-phenyl)-ethyl]-amide
(13) 3-tert-Butyl-4-oxo-10-oxa-3-aza-tricyclo[5.2.1.0$^{1,5}$]dec-8-ene-2,6-dicarboxylic acid 2-cyclohexylamide 6-[(3-methylsulfanyl-phenyl)-amide]
(14) 4-Oxo-3-propyl-10-oxa-3-aza-tricyclo[5.2.1.0$^{1,5}$]dec-8-ene-2,6-dicarboxylic acid 6-cyclohexylamide 2-[(3,5-dichloro-phenyl)-amide]
(15) 3-Benzyl-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]
(16) 4-Oxo-3-(tetrahydro-furan-2-ylmethyl)-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]
(17) 3-(4-Methyl-benzyl)-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]
(18) 3-Benzyl-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]
(19) 4-Oxo-3-pyridin-3-ylmethyl-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]
(20) 3-(4-Fluoro-benzyl)-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]
(21) 3-(2-Fluoro-benzyl)-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]
(22) 3-(2,3-Dimethyl-cyclohexyl)-4-oxo-10-oxa-3-aza-tricyclo[5.2.1.0$^{1,5}$]dec-8-ene-2,6-dicarboxylic acid 2-[(2-methyl-cyclohexyl)-amide]6-m-tolylamide
(23) 4-Oxo-3-thiophen-2-ylmethyl-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]
(24) 4-Oxo-3-(tetrahydro-furan-2-ylmethyl)-10-oxa-3-aza-tricyclo[5.2.1.0$^{1,5}$]dec-8-ene-2,6-dicarboxylic acid 6-[(2,3-dimethyl-cyclohexyl)-amide]2-[(3,5-dimethyl-phenyl)-amide]
(25) 2-[2-Cyclohexylcarbamoyl-6-(3-methoxy-phenylcarbamoyl)-4-oxo-10-oxa-3-aza-tricyclo[5.2.1.0$^{1,5}$]dec-8-en-3-ylmethyl]-1-ethyl-pyrrolidinium
(26) 4-Oxo-3-pyridin-3-ylmethyl-10-oxa-3-aza-tricyclo[5.2.1.0$^{1,5}$]dec-8-ene-2,6-dicarboxylic acid 6-[(2,3-dimethyl-cyclohexyl)-amide]2-[(3,5-dimethyl-phenyl)-amide]
(27) 3-(4-Methyl-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]
(28) 3-(4-Fluoro-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]
(29) 3-(2-Fluoro-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]
(30) 3-(4-Chloro-benzyl)-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]
(31) 4-Oxo-3-(tetrahydro-furan-2-ylmethyl)-10-oxa-3-aza-tricyclo[5.2.1.0$^{1,5}$]dec-8-ene-2,6-dicarboxylic acid 6-cyclohexylamide 2-[(3,5-dichloro-phenyl)-amide]
(32) 3-(2-Chloro-benzyl)-4-oxo-10-oxa-3-aza-tricyclo[5.2.1.0$^{1,5}$]dec-8-ene-2,6-dicarboxylic acid 2-cyclohexylamide 6-[(3-methoxy-phenyl)-amide]
(33) 3-Benzo[1,3]dioxol-5-ylmethyl-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]
(34) 3-(4-Methoxy-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]
(35) 3-(3-Methoxy-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]
(36) 3-(2-Fluoro-benzyl)-4-oxo-10-oxa-3-aza-tricyclo[5.2.1.0$^{1,5}$]dec-8-ene-2,6-dicarboxylic acid 6-[(2,3-dimethyl-cyclohexyl)-amide]2-[(3,5-dimethyl-phenyl)-amide]
(37) 3-(2-Chloro-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]
(38) 3-(4-Chloro-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(39) 3-(2,3-Dimethyl-cyclohexyl)-4-oxo-10-oxa-3-aza-tricyclo[5.2.1.0$^{1,5}$]dec-8-ene-2,6-dicarboxylic acid 6-[(4-chloro-phenyl)-amide]2-[(2,3-dimethyl-cyclohexyl)-amide]

(40) 3-(3-Methoxy-benzyl)-4-oxo-10-oxa-3-aza-tricyclo[5.2.1.0$^{1,5}$]dec-8-ene-2,6-dicarboxylic acid 6-[(2,3-dimethyl-cyclohexyl)-amide]2-[(3,5-dimethyl-phenyl)-amide]

(41) 3-Benzo[1,3]dioxol-5-ylmethyl-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(42) 4-Oxo-3-(1-phenyl-ethyl)-10-oxa-3-aza-tricyclo[5.2.1.0$^{1,5}$]dec-8-ene-2,6-dicarboxylic acid 2-[(2,3-dimethyl-cyclohexyl)-amide]6-[(3-methylsulfanyl-phenyl)-amide]

(43) 3-(2,3-Dimethyl-cyclohexyl)-4-oxo-10-oxa-3-aza-tricyclo[5.2.1.0$^{1,5}$]dec-8-ene-2,6-dicarboxylic acid 2-[(2,3-dimethyl-cyclohexyl)-amide]6-[(3-methylsulfanyl-phenyl)amide]

(44) 3-(3-Methoxy-benzyl)-4-oxo-10-oxa-3-aza-tricyclo[5.2.1.0$^{1,5}$]dec-8-ene-2,6-dicarboxylic acid 6-cyclohexylamide 2-[(3,5-dichloro-phenyl)-amide]

(45) 3-(4-Methyl-cyclohexyl)-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(46) 3-(2-Chloro-benzyl)-4-oxo-10-oxa-3-aza-tricyclo[5.2.1.0$^{1,5}$]dec-8-ene-2,6-dicarboxylic acid 6-cyclohexylamide 2-[(3,5-dichloro-phenyl)-amide]

(47) 3-(4-Fluoro-benzyl)-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(48) 3-(2,3-Dihydro-benzo[1,4]dioxin-2-ylmethyl)-4-oxo-10-oxa-3-aza-tricyclo[5.2.1.0$^{1,5}$]dec-8-ene-2,6-dicarboxylic acid 6-cyclohexylamide 2-[(3,5-dichloro-phenyl)-amide]

(49) 3-(3-Methoxy-benzyl)-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(50) 3-(4-Chloro-benzyl)-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(51) 3-[2-(4-Chloro-phenyl)-ethyl]-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(52) 3-(1-Methyl-3-phenyl-propyl)-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(53) 3-[2-(Benzyl-methyl-amino)-ethyl]-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(54) 3-[3-(Benzyl-methyl-amino)-propyl]-4-oxo-10-oxa-3-aza-tricyclo[5.2.1.0$^{1,5}$]dec-8-ene-2,6-dicarboxylic acid 6-[(3-chloro-4-fluoro-phenyl)-amide]2-[(2,3-dimethyl-cyclohexyl)-amide]

(55) 3-[2-(Benzyl-methyl-amino)-ethyl]-4-oxo-10-oxa-3-aza-tricyclo[5.2.1.0$^{1,5}$]dec-8-ene-2,6-dicarboxylic acid 2-cyclohexylamide 6-[(4-phenoxy-phenyl)-amide].

(56) 3-(1-Methyl-3-morpholin-4-yl-propyl)-4-oxo-10-oxa-3-aza-tricyclo[5.2.1.0$^{1,5}$]dec-8-ene-2,6-dicarboxylic acid 6-[(2,6-dichloro-tetrahydro-pyran-4-yl)-amide]2-[(2,3-dimethyl-phenyl)-amide]

(57) 3-(1-Methyl-3-pyridin-4-yl-propyl)-4-oxo-10-oxa-3-aza-tricyclo[5.2.1.0$^{1,5}$]decane-2,6-dicarboxylic acid 6-[(2,6-dichloro-pyridin-4-yl)-amide]2-[(2,3-dimethyl-cyclohexyl)-amide]

(58) 3-(4-Chloro-benzyl)-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]

(59) 3-(4-Chloro-benzyl)-4-oxo-10-oxa-3-aza-tricyclo[5.2.1.0$^{1,5}$]decane-2,6-dicarboxylic acid 6-[(3,5-dichloro-phenyl)-amide]2-[(2,3-dimethyl-cyclohexyl)-amide]

(60) 3-(4-Fluoro-piperazin-1-ylmethyl)-4-oxo-10-oxa-3-aza-tricyclo[5.2.1.0$^{1,5}$]dec-8-ene-2,6-dicarboxylic acid 6-[(6-chloro-4-fluoro-pyridin-2-yl)-amide]2-[(2,3-dimethyl-piperazin-1-yl)-amide]

(61) 3-(5-Fluoro-pyridin-2-ylmethyl)-4-oxo-10-oxa-2,3,6-triaza-tricyclo[5.2.1.0$^{1,5}$]dec-8-ene-2,6-dicarboxylic acid 6-[(3-chloro-5-fluoro-phenyl)-amide]2-[(2,3-dimethyl-cyclohexyl)-amide]

(62) 4-(1-Methyl-2-phenylamino-ethyl)-5-oxo-11-oxa-4-aza-tricyclo[6.2.1.0$^{1,6}$]undecane-3,7-dicarboxylic acid 7-[(4-chloro-5-fluoro-pyridin-2-yl)-amide]3-[(2,3-dimethyl-piperazin-1-yl)-amide]

(63) 4-(4-Fluoro-piperazin-1-ylmethyl)-5-oxo-11-oxa-4-aza-tricyclo[6.2.1.0$^{1,6}$]undec-9-ene-3,7-dicarboxylic acid 7-[(6-chloro-4-fluoro-pyridin-2-yl)-amide]3-[(2,3-dimethyl-piperazin-1-yl)-amide]

(64) 4-(Cyclopropylaminomethyl-methyl-amino)-5-oxo-11-oxa-4-aza-tricyclo[6.2.1.0$^{1,6}$]undec-9-ene-3,7-dicarboxylic acid 7-[(4,5-difluoro-pyridin-2-yl)-amide]3-[(2,3-dimethyl-morpholin-4-yl)-amide]

(65) 4-[2-(4-Chloro-piperazin-1-yl)-1-methyl-ethyl]-5-oxo-11-oxa-4-aza-tricyclo[6.2.1.0$^{1,6}$]undecane-3,7-dicarboxylic acid 7-[(4,5-difluoro-pyridin-2-yl)-amide]3-[(2,3-dimethyl-piperazin-1-yl)-amide]

(66) 5-Oxo-4-{1-[(pyridin-4-ylmethyl)-amino]-ethyl}-11-oxa-4-aza-tricyclo[6.2.1.0$^{1,6}$]undecane-3,7-dicarboxylic acid 7-[(3,5-dichloro-phenyl)-amide]3-[(2,3-dimethyl-piperidin-1-yl)-amide]

In one embodiment of the pharmaceutical composition, the compound having a structural formula (I) is in a therapeutically effective amount.

In another aspect, the present invention provides a method for treating a condition, disorder, or disease, or stimulating contraceptive effect, in a patient in need thereof comprising administering to the patient a therapeutically effective amount of the compound of formula (I) as defined above in the pharmaceutical composition, or a salt, solvent, ester, and/or prodrug thereof, wherein the condition, disorder, or disease is implicated in the activation or hyperactivity of low voltage-gated calcium channels.

Preferably, the condition, disorder, or disease is selected from the group consisting of epilepsy, peripheral neuropathy, Parkinson's disease, essential tremor, insomnia, psychosis, schizophrenia, hypertension, angina, arteriosclerosis, nervous system injury, anxiety disorder, seizure, convulsion, Huntington's chorea, Alzheimer's disease, multiple sclerosis, autoimmune disease, tremor, retinopathy, neoplasm, inflammation, cranial neuropathy, myocardial infarction, stroke, pain, acute pain, chronic pain, neuropathic pain, inflammatory pain, arthritis, migraine, cluster headaches, trigeminal neuralgia, herpetic neuralgia, general neuralgias, neurodegenerative disorders, anxiety, depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck-pain, severe or intractable pain, nociceptive pain, breakthrough pain, postsurgical pain, cancer pain, cancer, hypertension, stroke, type 1 or type 2 diabetes, hyperaldosteronemia, preterm labor, urinary incontinence, and brain aging.

In another aspect, the present invention provides a method for enhancing the quality of sleep in a patient in need thereof comprising administering to the patient a therapeutically effective amount of the compound of formula (I) as defined above in the pharmaceutical composition, or a salt, solvent, ester, and/or prodrug thereof.

In another aspect, the present invention provides a method for increasing slow-wave sleep in a patient in need thereof comprising administering to the patient a therapeutically effective amount of the compound of formula (I) as defined above in the pharmaceutical composition, or a salt, solvent, ester, and/or prodrug thereof.

In another aspect, the present invention provides a method for decreasing fragmentation of sleep patterns in a patient in need thereof comprising administering to the patient a therapeutically effective amount of the compound of formula (I) as defined above in the pharmaceutical composition, or a salt, solvent, ester, and/or prodrug thereof.

In another aspect, the present invention provides a method for enhancing cognition of sleep patterns in a patient in need thereof comprising administering to the patient a therapeutically effective amount of the compound of formula (I) as defined above in the pharmaceutical composition, or a salt, solvent, ester, and/or prodrug thereof.

In another aspect, the present invention provides a method for increasing memory retention in a patient in need thereof comprising administering to the patient a therapeutically effective amount of the compound of formula (I) as defined above in the pharmaceutical composition, or a salt, solvent, ester, and/or prodrug thereof.

In another aspect, the present invention provides a method of modulating calcium ion channels comprising contacting the compound of formula (I) as defined above in the pharmaceutical composition, or a salt, solvent, ester, and/or prodrug thereof, with the calcium ion channels. In embodiment of the present invention, the modulation comprises selectively antagonizing at least one subunit of T-type calcium ion channels in a patient in need thereof.

In another aspect, the present invention provides a compound having a structural formula (II), (III) or (IV), or a salt, solvate, ester, and/or prodrug thereof:

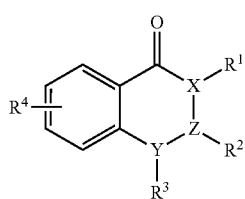

(II)

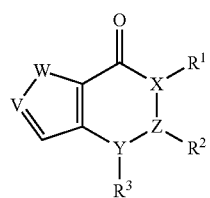

(III)

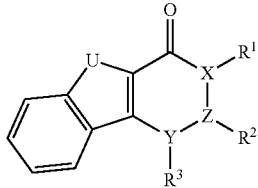

(IV)

wherein:
X—Z is —C═C— or —N—C— or —C—N—;
Y—Z is —N—C—, —N═C—, —CH—CH—, or —C—N—;
provided that X—Z is not —C═C— when Y—Z is —N═C—;
$R^1$ is —S(O)$_k$R$^5$, —NH—S(O)$_k$R$^5$, alkyl, substituted alkyl, aryl, substituted aryl, arylalkyl, substituted arylalkyl, cycloalkylalkyl, substituted cycloalkylalkyl, cycloheteroalkylalkyl, substituted cycloheteroalkylalkyl, heteroaryl, substituted heteroaryl, heteroarylalkyl, substituted heteroarylalkyl, heteroalkyl, substituted heteroalkyl, —CONR$^6$R$^7$ or alternatively R$^1$ and R$^2$ along with the atoms to which they are attached form a cycloalkyl, substituted cycloalkyl, cycloheteroalkyl, substituted cycloheteroalkyl, aryl, substituted aryl, heteroaryl, substituted heteroaryl ring, fused indanoyl or substituted fused indanoyl ring;
k is 0, 1 or 2;
$R^2$ is hydrogen, —S(O)$_l$R$^8$, ═O, —NR$^{21}$COR$^{18}$, —NR$^{19}$R$^{20}$, alkoxycarbonyl, substituted alkoxycarbonyl, alkyl, substituted alkyl, aryl, substituted aryl, arylalkyl, substituted arylalkyl, heteroaryl, substituted heteroaryl, heteroarylalkyl, substituted heteroarylalkyl or alternatively $R^2$ and $R^3$ along with the atoms to which they are attached form a cycloalkyl, substituted cycloalkyl, cycloheteroalkyl, substituted cycloheteroalkyl, aryl, substituted aryl, heteroaryl or substituted heteroaryl ring;
l is 0, 1 or 2;
$R^3$ is hydrogen, alkyl, substituted alkyl, arylalkyl, substituted arylalkyl, heteroaryl, substituted heteroaryl, heteroarylalkyl, substituted heteroarylalkyl, heteroalkyl, substituted heteroalkyl or —CONR$^8$R$^9$ when Y—Z is —N—C—, or —CH—CH— and is not defined when Y—Z is —N═C—;
provided that $R^2$ does not form a ring with both $R^1$ and $R^3$;
$R^4$ is alkyl, acyl, substituted acyl, acyloxycarbonyl, substituted acyloxycarbonyl, aryloxycarbonyl, substituted aryloxycarbonyl, alkoxy, substituted alkoxy, alkyl, substituted alkyl, arylalkyl, substituted arylalkyl, heteroaryl, substituted heteroaryl, heteroarylalkyl, substituted heteroarylalkyl, heteroalkyl, substituted arylalkyl, halo, hydroxyl, nitro, cyano, —CONR$^{10}$R$^{11}$, —NR$^{12}$R$^{13}$, carboxyl or —S(O)$_m$R$^{14}$;
m is 0, 1 or 2;
$R^5$, $R^8$ and $R^{14}$ are independently alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;
$R^6$ and $R^7$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively $R^6$ and $R^7$ along with the atoms to which they are attached form a cycloheteroalkyl or substituted cycloheteroalkyl, ring;
$R^8$ and $R^9$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively R⁸ and R⁹ along with the atoms to which they are attached form a cycloheteroalkyl or substituted cycloheteroalkyl, ring;

R¹⁰ and R¹¹ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively R¹⁰ and R¹¹ along with the atoms to which they are attached form a cycloheteroalkyl or substituted cycloheteroalkyl, ring;

R¹² and R¹³ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively R¹² and R¹³ along with the atoms to which they are attached form a cycloheteroalkyl or substituted cycloheteroalkyl, ring;

W is —O—, —NR¹⁵ or —S—;
U is —O—, —NR¹⁶ or —S—;
V is —CH— or —N—;

R¹⁵ and R¹⁶ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;

R¹⁸ and R²¹ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;

R¹⁹ and R²⁰ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl; and provided that the above Formula (II), (III) or (IV) does not include the compounds of Table 2.

Some representative compounds of formula II, III and IV, as examples, are given in the Table 2. In order that the invention described herein may be more fully understood, the following examples are set forth. It should be understood that these examples are for illustrative purposes only and are not to be construed as limiting this invention in any manner. The following compounds can be readily synthesized described in the literature by one skilled in the art of organic synthesis or readily acquired from commercially available sources.

TABLE 2

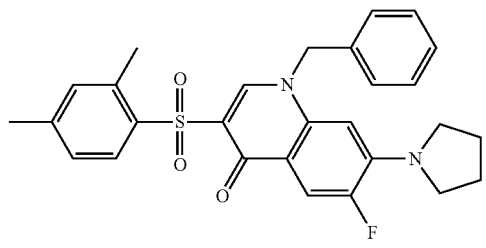

(101)

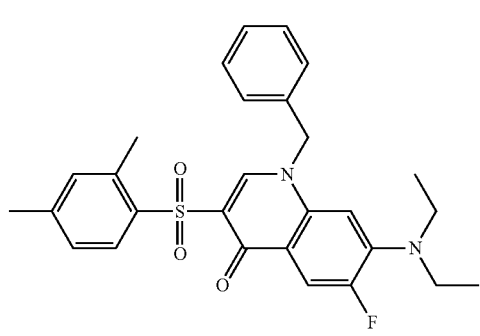

(102)

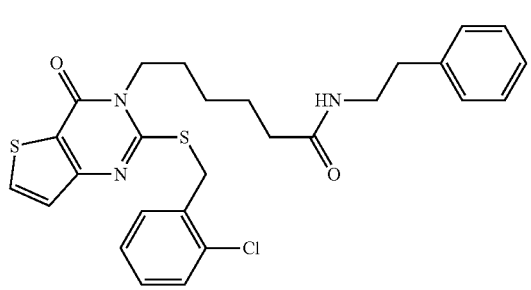

(103)

TABLE 2-continued
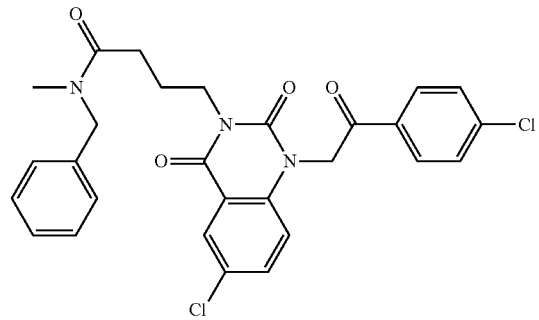
(104)
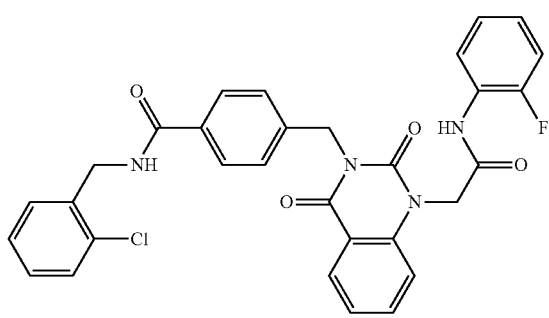
(105)
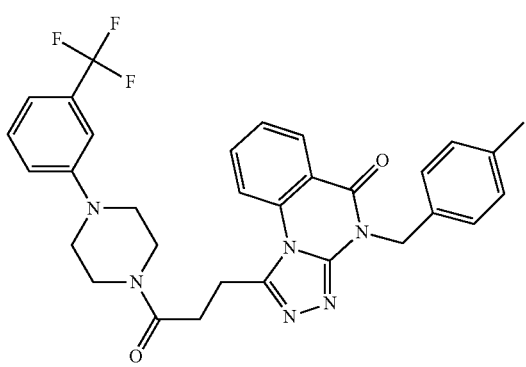
(106)
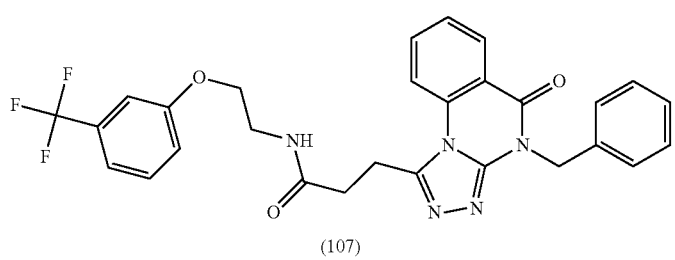 [SMILES: O=C(CCc1nnc2n(Cc3ccccc3)c(=O)c3ccccc3n12)NCCOc1cccc(C(F)(F)F)c1]
(107)

TABLE 2-continued
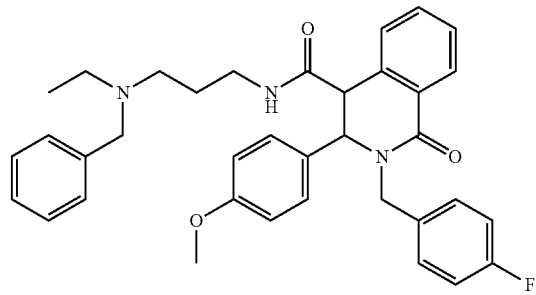
(108)
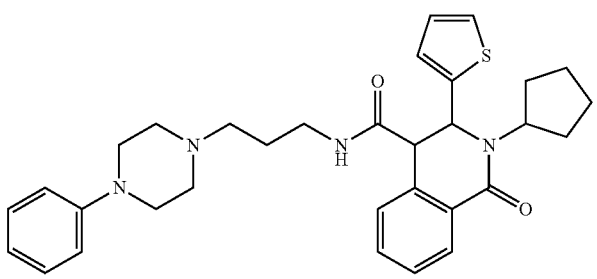
(109)
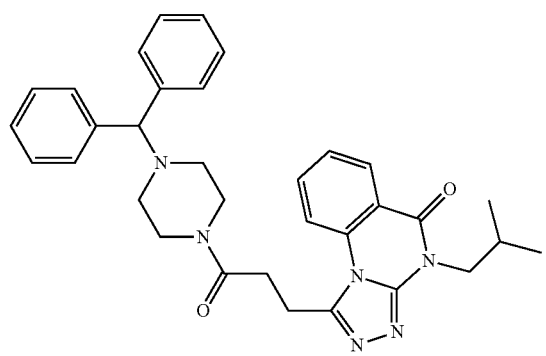
(110)
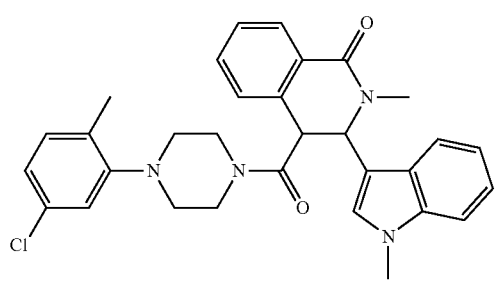
(111)

TABLE 2-continued
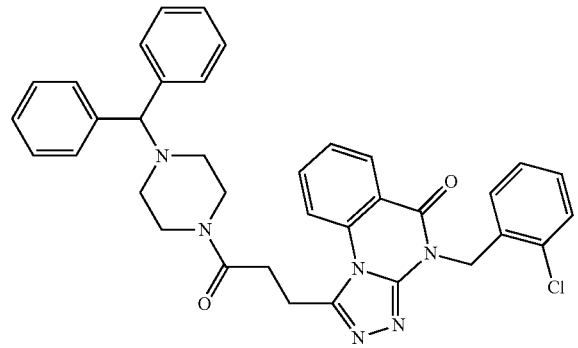
(112)
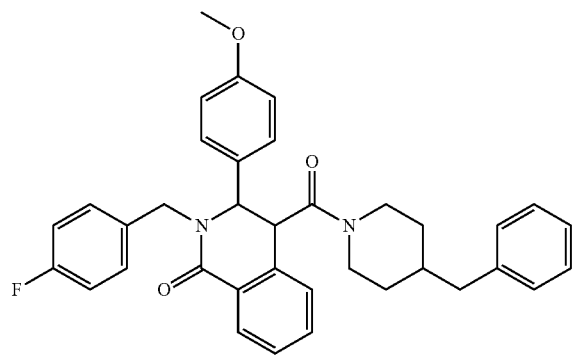
(113)
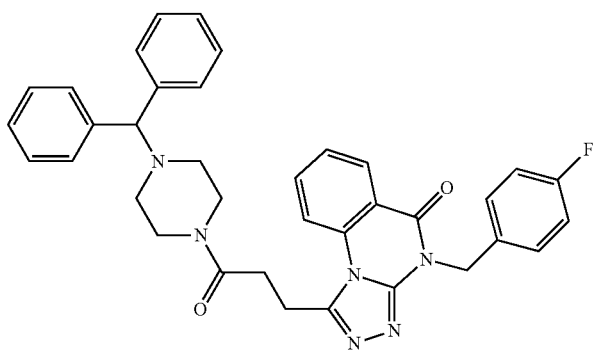
(114)
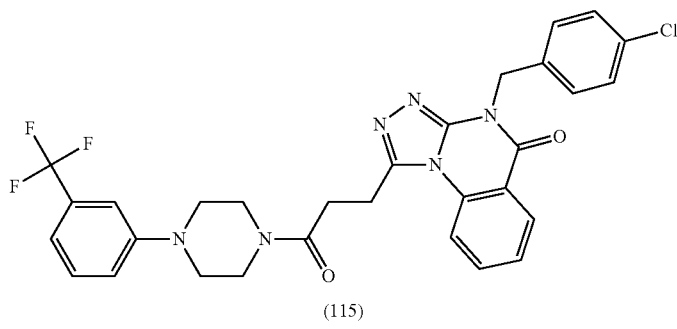 [SMILES: O=C(CCc1nnc2n(Cc3ccc(Cl)cc3)c(=O)c3ccccc3n12)N1CCN(c2cccc(C(F)(F)F)c2)CC1]
(115)

TABLE 2-continued
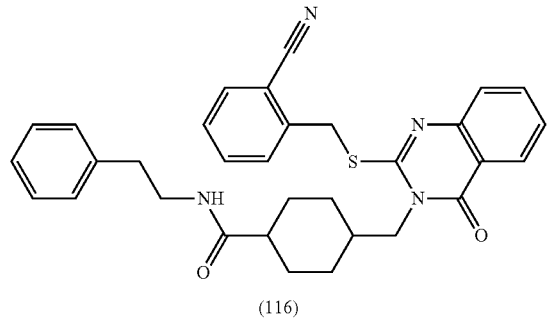 [SMILES: N#Cc1ccccc1CSc1nc2ccccc2c(=O)n1CC1CCC(C(=O)NCCc2ccccc2)CC1]
(116)
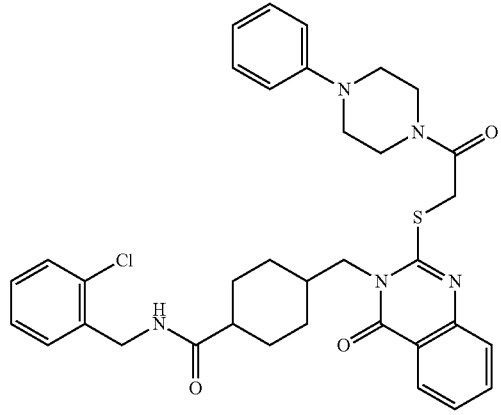
(117)
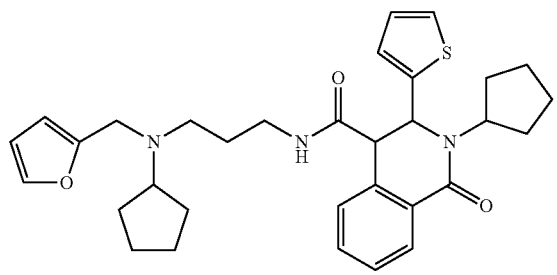
(118)
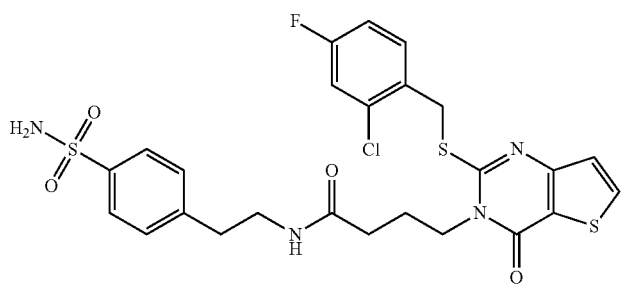
(119)

TABLE 2-continued
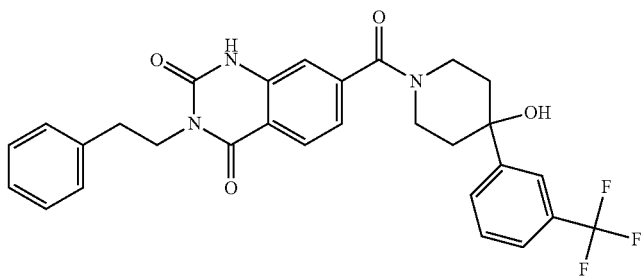
(120)
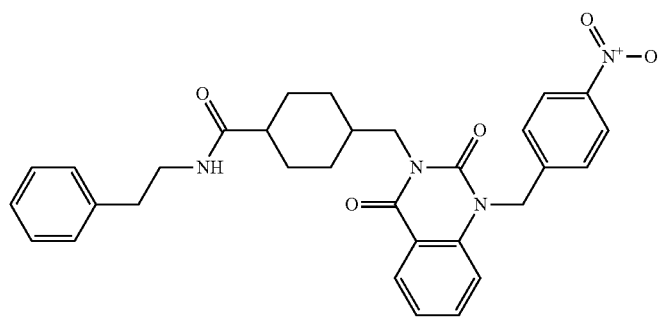
(121)
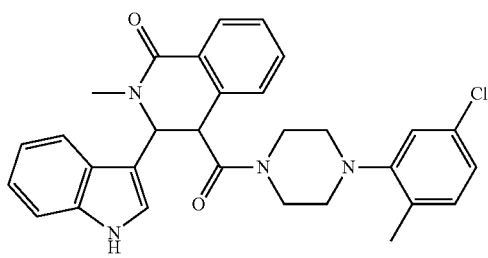
(122)
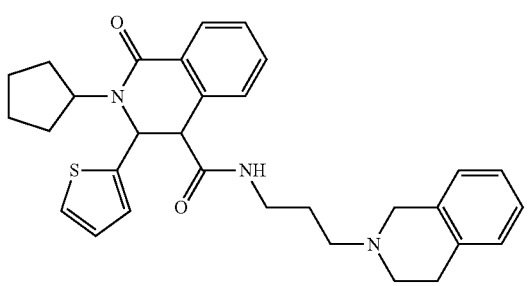
(123)
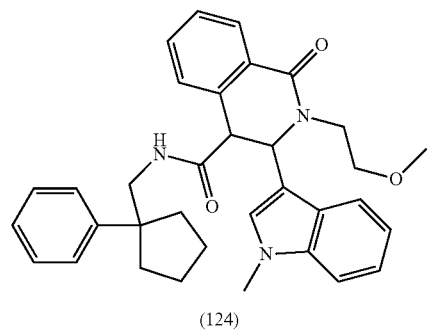 [SMILES: COCCN1C(=O)c2ccccc2C(C(=O)NCC2(c3ccccc3)CCCC2)C1c1cn(C)c2ccccc12]
(124)

TABLE 2-continued
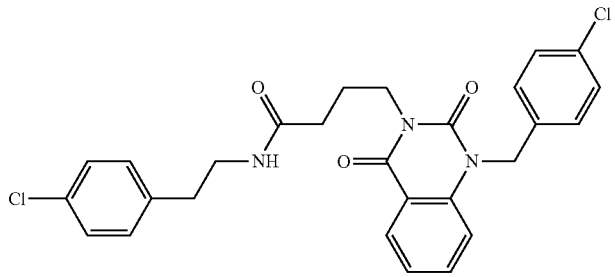
(125)
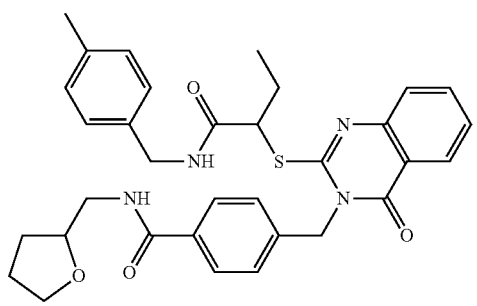
(126)
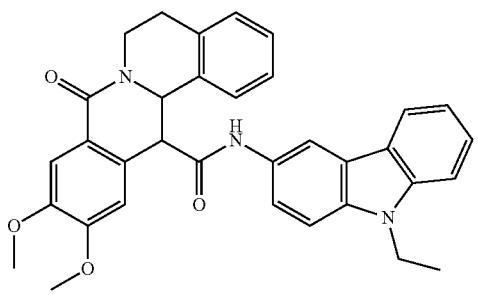
(127)
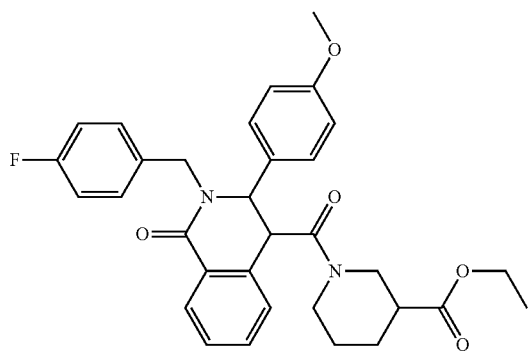
(128)

TABLE 2-continued
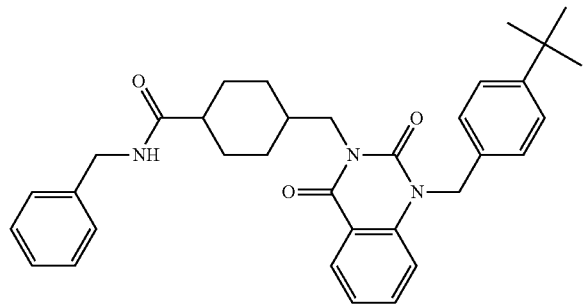
(129)
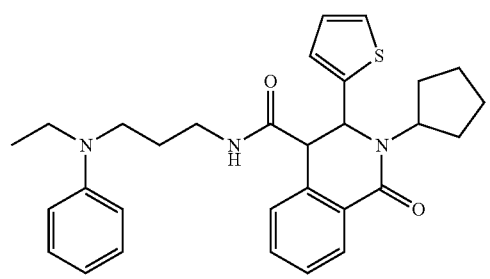
(130)
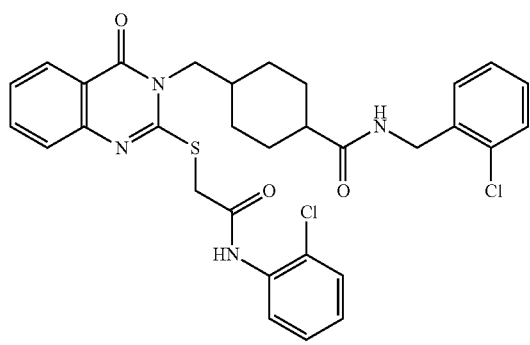
(131)
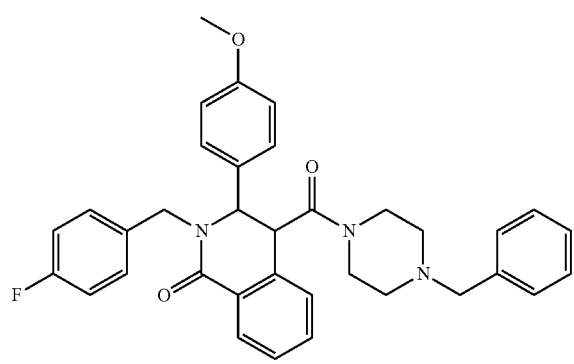
(132)

TABLE 2-continued
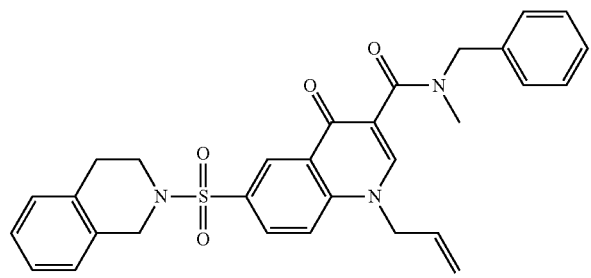
(133)
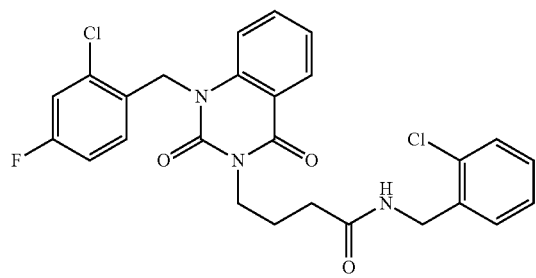
(134)
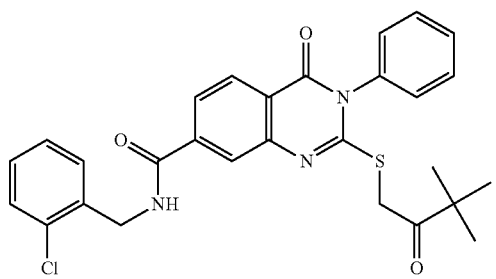
(135)
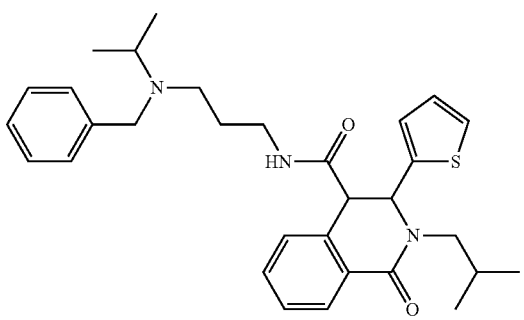
(136)
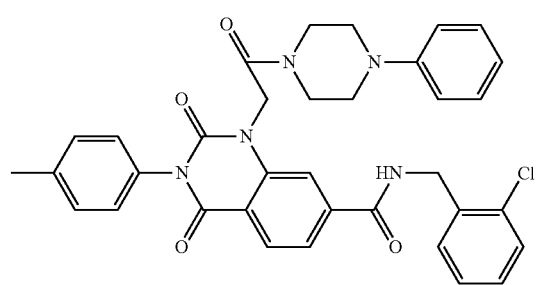
(137)

TABLE 2-continued
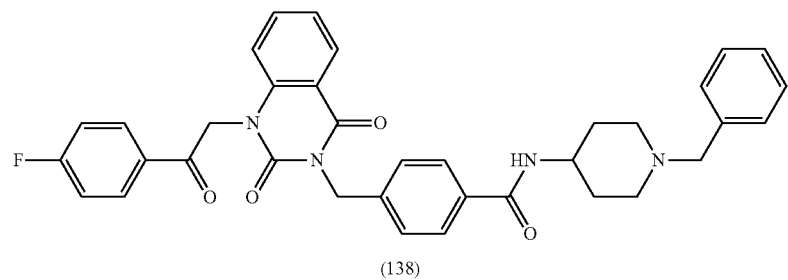 [SMILES: O=C(Cn1c(=O)n(Cc2ccc(C(=O)NC3CCN(Cc4ccccc4)CC3)cc2)c(=O)c2ccccc21)c1ccc(F)cc1]
(138)
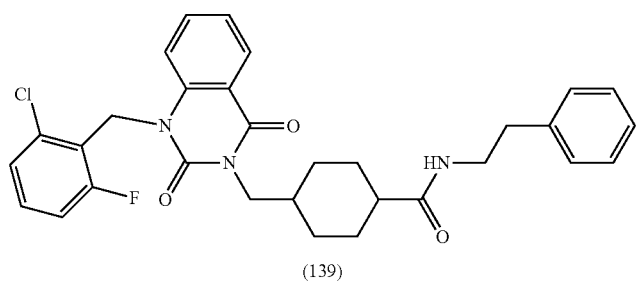 [SMILES: O=C(NCCc1ccccc1)C1CCC(Cn2c(=O)c3ccccc3n(Cc3c(F)cccc3Cl)c2=O)CC1]
(139)
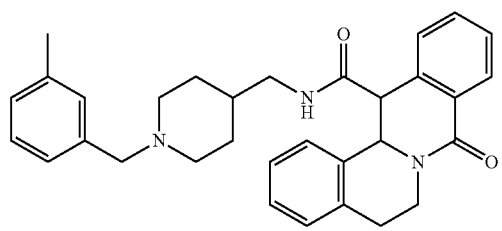
(140)
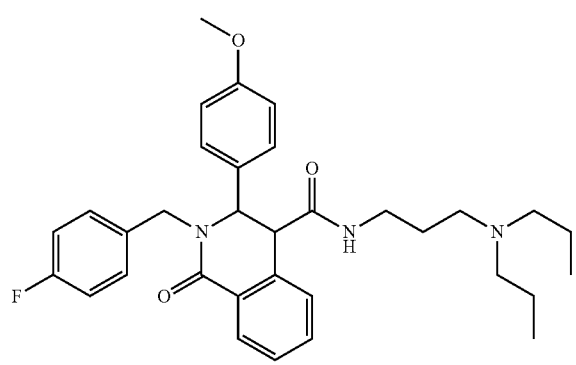
(141)

TABLE 2-continued
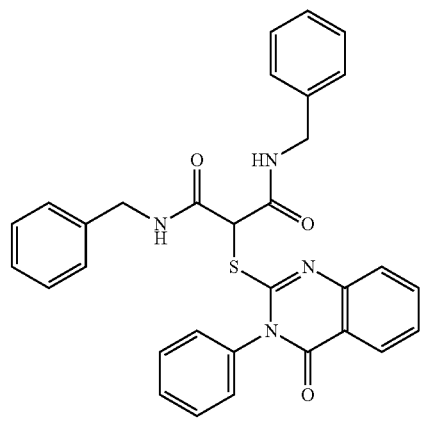
(142)
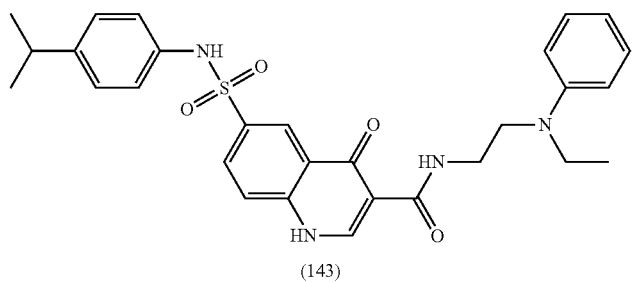 [SMILES: CCN(CCNC(=O)c1c[nH]c2ccc(S(=O)(=O)Nc3ccc(C(C)C)cc3)cc2c1=O)c1ccccc1]
(143)
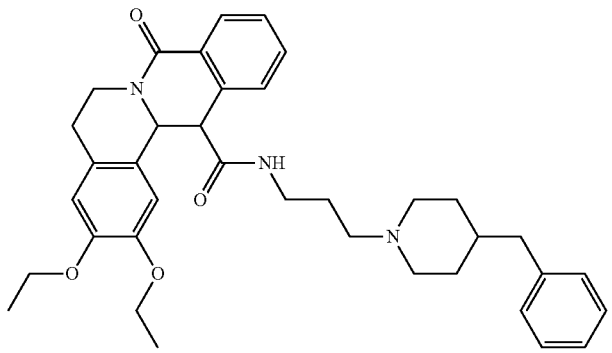
(144)
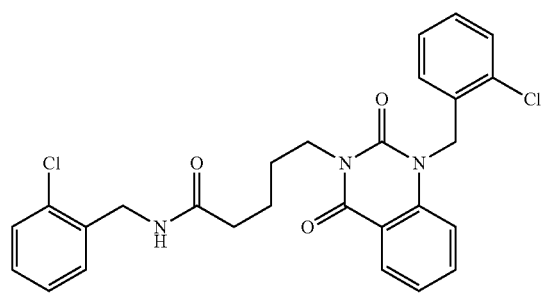
(145)

TABLE 2-continued
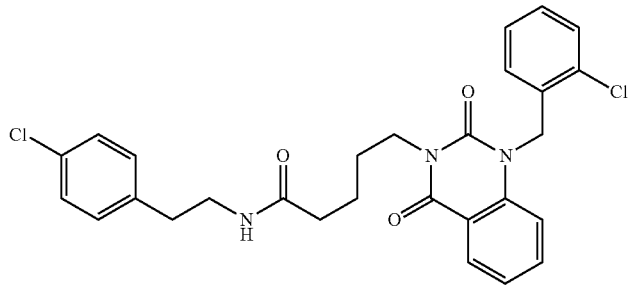
(146)
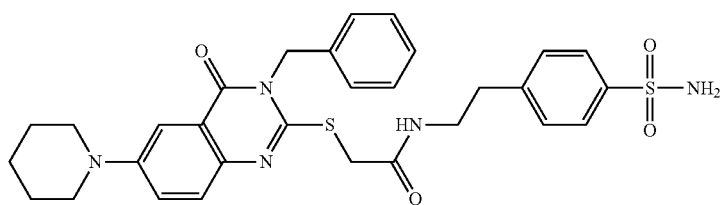
(147)
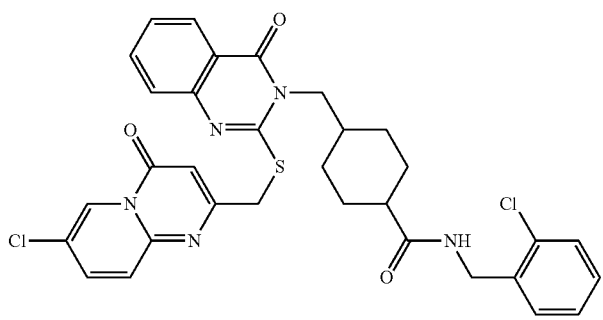
(148)
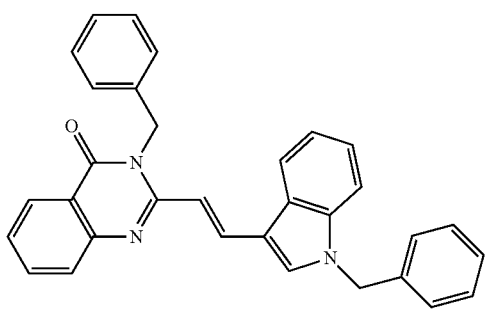
(149)
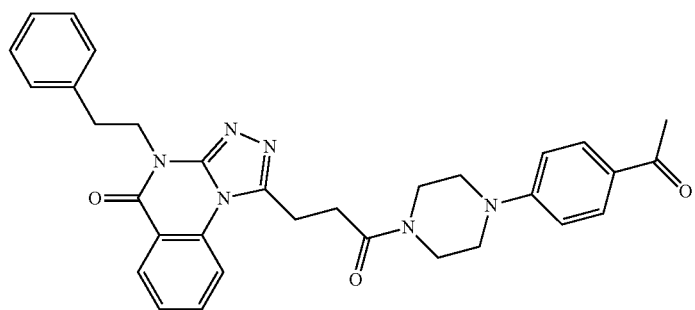
(150)

TABLE 2-continued
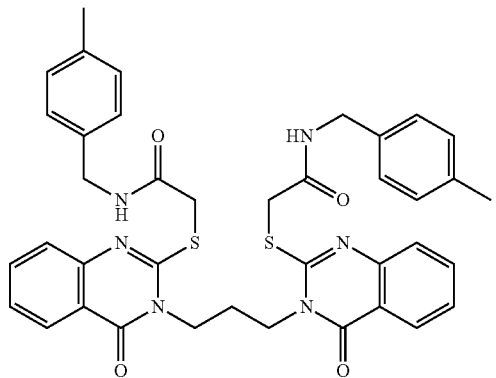
(151)
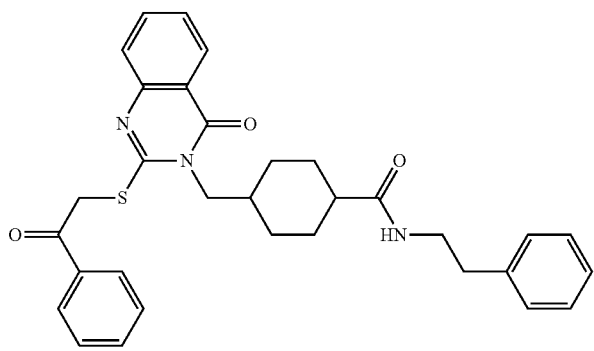
(152)
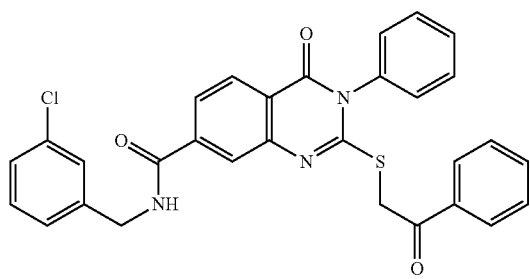
(153)
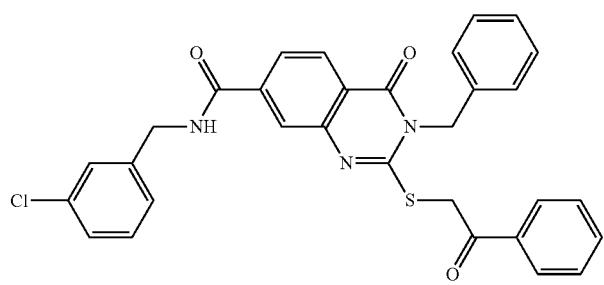
(154)

TABLE 2-continued
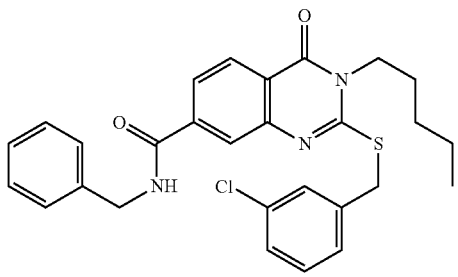
(155)
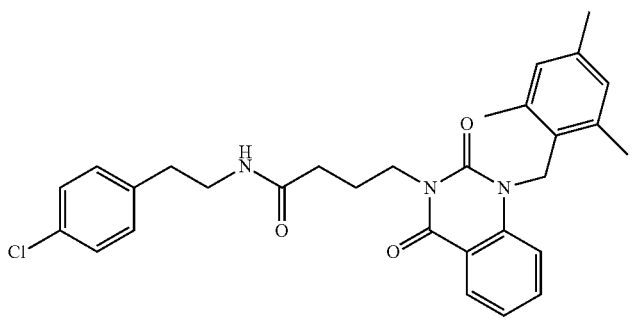
(156)
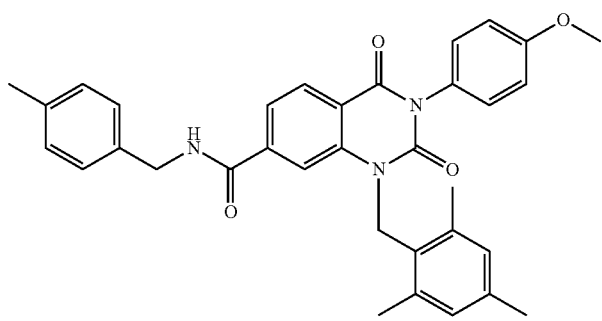
(157)
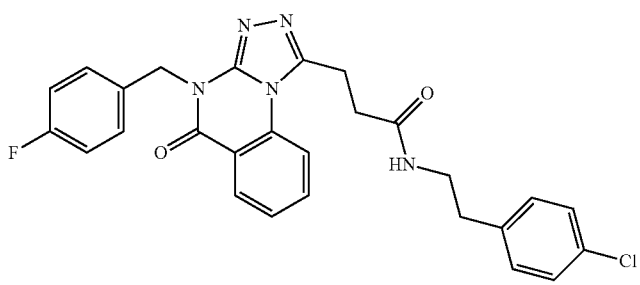
(158)

TABLE 2-continued
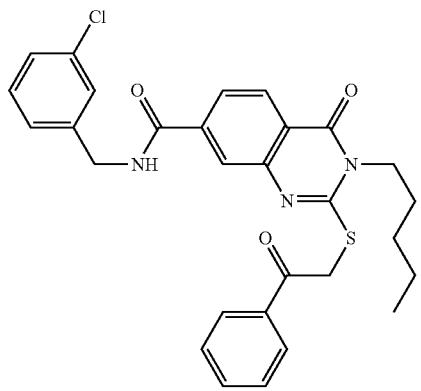
(159)
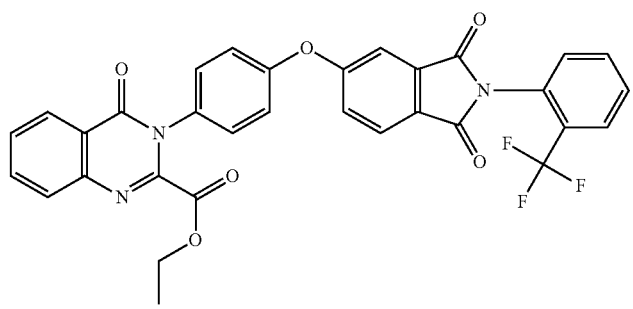
(160)
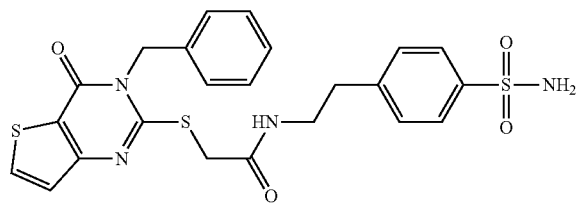
(161)
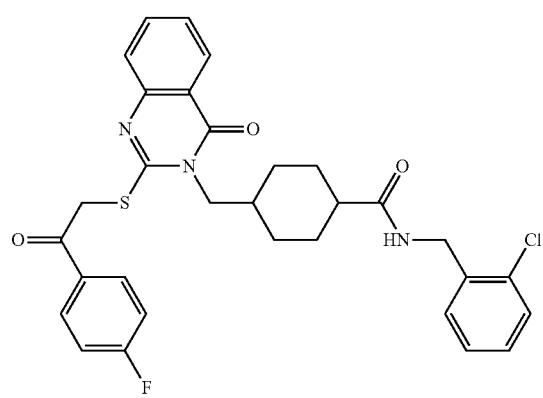
(162)

TABLE 2-continued
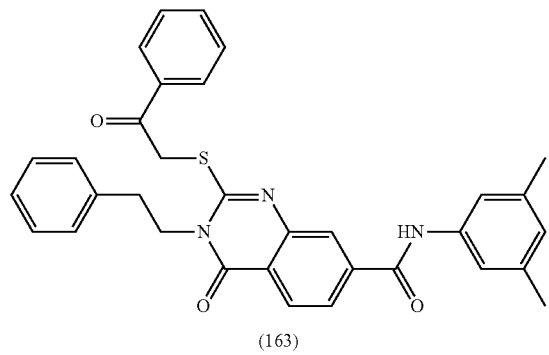 [SMILES: Cc1cc(C)cc(NC(=O)c2ccc3c(=O)n(CCc4ccccc4)c(SCC(=O)c4ccccc4)nc3c2)c1]
(163)
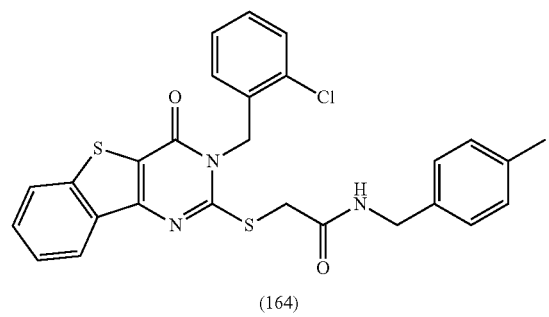 [SMILES: Cc1ccc(CNC(=O)CSc2nc3c(sc4ccccc43)c(=O)n2Cc2ccccc2Cl)cc1]
(164)
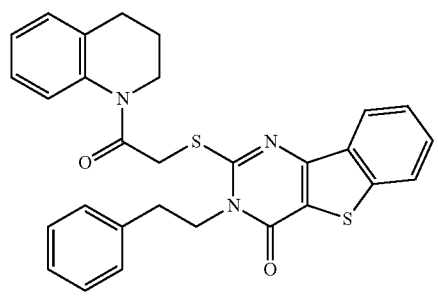
(165)
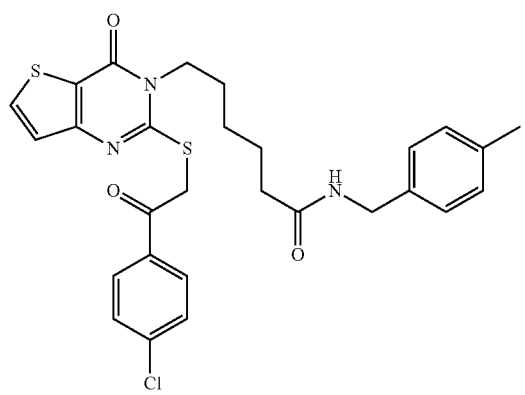
(166)

TABLE 2-continued

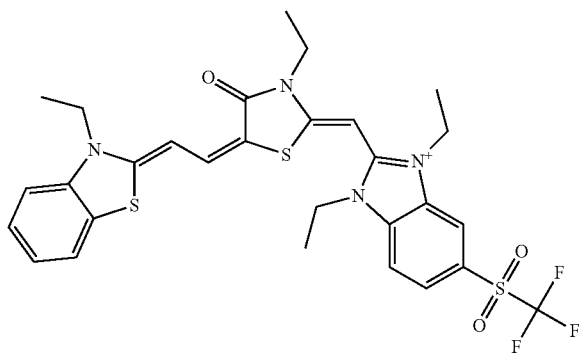

(167)

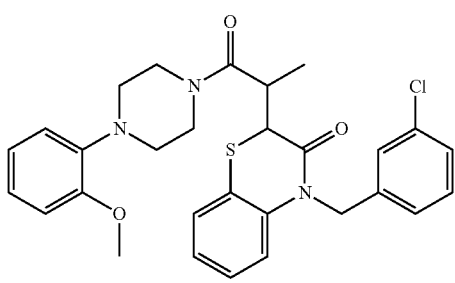

(168)

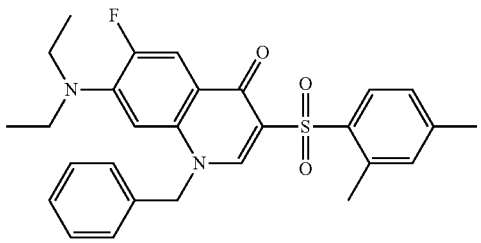

(169)

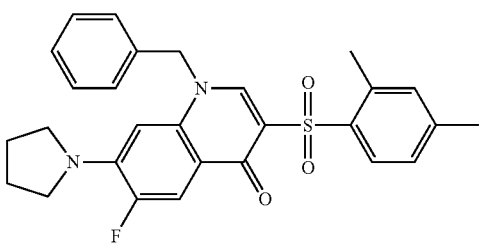

(170)

or the salt, solvate, ester, and/or prodrug thereof.

The above-listed compounds may also be represented by their chemical names as follows:

(101) 3-(2,4-dimethylphenylsulfonyl)-1-benzyl-6-fluoro-7-(pyrrolidin-1-yl)quinolin-4(1H)-one
(102) 3-(2,4-dimethylphenylsulfonyl)-1-benzyl-7-(diethylamino)-6-fluoroquinolin-4(1H)-one
(103) 6-(2-(2-chlorobenzylthio)-4-oxothieno[3,2-d]pyrimidin-3(4H)-yl)-N-phenethylhexanamide
(104) N-Benzyl-4-{6-chloro-1-[2-(4-chloro-phenyl)-2-oxo-ethyl]-2,4-dioxo-1,4-dihydro-2H-quinazolin-3-yl}-N-methyl-butyramide
(105) N-(2-Chloro-benzyl)-4-{1-[(2-fluoro-phenylcarbamoyl)-methyl]-2,4-dioxo-1,4-dihydro-2H-quinazolin-3-ylmethyl}-benzamide
(106) 4-(4-Methyl-benzyl)-1-{3-oxo-3-[4-(3-trifluoromethyl-phenyl)-piperazin-1-yl]-propyl}-4H-[1,2,4]triazolo[4,3-a]quinazolin-5-one
(107) 3-(4-Benzyl-5-oxo-4,5-dihydro-[1,2,4]triazolo[4,3-a]quinazolin-1-yl)-N-[2-(3-trifluoromethyl-phenoxy)-ethyl]-propionamide
(108) 2-(4-Fluoro-benzyl)-3-(4-methoxy-phenyl)-1-oxo-1,2,3,4-tetrahydro-isoquinoline-4-carboxylic acid [3-(benzyl-ethyl-amino)-propyl]-amide (109) 2-Cyclopentyl-1-oxo-3-thiophen-2-yl-1,2,3,4-tetrahydro-isoquinoline-4-carboxylic acid [3-(4-phenyl-piperazin-1-yl)-propyl]-amide
(110) 1-[3-(4-Benzhydryl-piperazin-1-yl)-3-oxo-propyl]-4-isobutyl-4H-[1,2,4]triazolo[4,3-a]quinazolin-5-one
(111) 4-[4-(5-Chloro-2-methyl-phenyl)-piperazine-1-carbonyl]-2-methyl-3-(1-methyl-1H-indol-3-yl)-3,4-dihydro-2H-isoquinolin-1-one
(112) 1-[3-(4-Benzhydryl-piperazin-1-yl)-3-oxo-propyl]-4-(2-chloro-benzyl)-4H-[1,2,4]triazolo[4,3-a]quinazolin-5-one
(113) 4-(4-Benzyl-piperidine-1-carbonyl)-2-(4-fluoro-benzyl)-3-(4-methoxy-phenyl)-3,4-dihydro-2H-isoquinolin-1-one
(114) 1-[3-(4-Benzhydryl-piperazin-1-yl)-3-oxo-propyl]-4-(4-fluoro-benzyl)-4H-[1,2,4]triazolo[4,3-a]quinazolin-5-one
(115) 4-(4-Chloro-benzyl)-1-{3-oxo-3-[4-(3-trifluoromethyl-phenyl)-piperazin-1-yl]-propyl}-4H-[1,2,4]triazolo[4,3-a]quinazolin-5-one
(116) 4-[2-(2-Cyano-benzylsulfanyl)-4-oxo-4H-quinazolin-3-ylmethyl]-cyclohexanecarboxylic acid phenethyl-amide
(117) 4-{4-Oxo-2-[2-oxo-2-(4-phenyl-piperazin-1-yl)-ethylsulfanyl]-4H-quinazolin-3-ylmethyl}-cyclohexanecarboxylic acid 2-chloro-benzylamide
(118) 2-Cyclopentyl-1-oxo-3-thiophen-2-yl-1,2,3,4-tetrahydro-isoquinoline-4-carboxylic acid [3-(cyclopentyl-furan-2-ylmethyl-amino)-propyl]-amide
(119) 4-[2-(2-Chloro-4-fluoro-benzylsulfanyl)-4-oxo-4H-thieno[3,2-d]pyrimidin-3-yl]-N-[2-(4-sulfamoyl-phenyl)-ethyl]-butyramide
(120) 7-[4-Hydroxy-4-(3-trifluoromethyl-phenyl)-piperidine-1-carbonyl]-3-phenethyl-1H-quinazoline-2,4-dione
(121) 4-[1-(4-Nitro-benzyl)-2,4-dioxo-1,4-dihydro-2H-quinazolin-3-ylmethyl]-cyclohexanecarboxylic acid phenethyl-amide
(122) 4-[4-(5-Chloro-2-methyl-phenyl)-piperazine-1-carbonyl]-3-(1H-indol-3-yl)-2-methyl-3,4-dihydro-2H-isoquinolin-1-one
(123) 2-Cyclopentyl-1-oxo-3-thiophen-2-yl-1,2,3,4-tetrahydro-isoquinoline-4-carboxylic acid [3-(3,4-dihydro-1H-isoquinolin-2-yl)-propyl]-amide
(124) 2-(2-Methoxy-ethyl)-3-(1-methyl-1H-indol-3-yl)-1-oxo-1,2,3,4-tetrahydro-isoquinoline-4-carboxylic acid (1-phenyl-cyclopentylmethyl)-amide
(125) 4-[1-(4-Chloro-benzyl)-2,4-dioxo-1,4-dihydro-2H-quinazolin-3-yl]-N-[2-(4-chloro-phenyl)-ethyl]-butyramide
(126) 4-{2-[1-(4-Methyl-benzylcarbamoyl)-propylsulfanyl]-4-oxo-4H-quinazolin-3-ylmethyl}-N-(tetrahydro-furan-2-ylmethyl)-benzamide
(127) 10,11-Dimethoxy-8-oxo-5,8,13,13a-tetrahydro-6H-isoquino[3,2-a]isoquinoline-13-carboxylic acid (9-ethyl-9H-carbazol-3-yl)-amide
(128) 1-[2-(4-Fluoro-benzyl)-3-(4-methoxy-phenyl)-1-oxo-1,2,3,4-tetrahydro-isoquinoline-4-carbonyl]-piperidine-3-carboxylic acid ethyl ester
(129) 4-[1-(4-tert-Butyl-benzyl)-2,4-dioxo-1,4-dihydro-2H-quinazolin-3-ylmethyl]-cyclohexanecarboxylic acid benzylamide
(130) 2-Cyclopentyl-1-oxo-3-thiophen-2-yl-1,2,3,4-tetrahydro-isoquinoline-4-carboxylic acid [3-(ethyl-phenyl-amino)-propyl]-amide
(131) 4-{2-[(2-Chloro-phenylcarbamoyl)-methylsulfanyl]-4-oxo-4H-quinazolin-3-ylmethyl}-cyclohexanecarboxylic acid 2-chloro-benzylamide
(132) 4-(4-Benzyl-piperazine-1-carbonyl)-2-(4-fluoro-benzyl)-3-(4-methoxy-phenyl)-3,4-dihydro-2H-isoquinolin-1-one
(133) 1-Allyl-6-(3,4-dihydro-1H-isoquinoline-2-sulfonyl)-4-oxo-1,4-dihydro-quinoline-3-carboxylic acid benzyl-methyl-amide
(134) N-(2-Chloro-benzyl)-4-[1-(2-chloro-4-fluoro-benzyl)-2,4-dioxo-1,4-dihydro-2H-quinazolin-3-yl]-butyramide
(135) 2-(3,3-Dimethyl-2-oxo-butylsulfanyl)-4-oxo-3-phenyl-3,4-dihydro-quinazoline-7-carboxylic acid 2-chloro-benzylamide
(136) 2-Isobutyl-1-oxo-3-thiophen-2-yl-1,2,3,4-tetrahydro-isoquinoline-4-carboxylic acid [3-(benzyl-isopropyl-amino)-propyl]-amide
(137) 2,4-Dioxo-1-[2-oxo-2-(4-phenyl-piperazin-1-yl)-ethyl]-3-p-tolyl-1,2,3,4-tetrahydro-quinazoline-7-carboxylic acid 2-chloro-benzylamide
(138) N-(1-Benzyl-piperidin-4-yl)-4-{1-[2-(4-fluoro-phenyl)-2-oxo-ethyl]-2,4-dioxo-1,4-dihydro-2H-quinazolin-3-ylmethyl}-benzamide
(139) 4-[1-(2-Chloro-6-fluoro-benzyl)-2,4-dioxo-1,4-dihydro-2H-quinazolin-3-ylmethyl]-cyclohexanecarboxylic acid phenethyl-amide
(140) 8-Oxo-5,8,13,13a-tetrahydro-6H-isoquino[3,2-a]isoquinoline-13-carboxylic acid [1-(3-methyl-benzyl)-piperidin-4-ylmethyl]-amide
(141) 2-(4-Fluoro-benzyl)-3-(4-methoxy-phenyl)-1-oxo-1,2,3,4-tetrahydro-isoquinoline-4-carboxylic acid (3-dipropylamino-propyl)-amide
(142) N,N'-Dibenzyl-2-(4-oxo-3-phenyl-3,4-dihydro-quinazolin-2-ylsulfanyl)-malonamide
(143) 6-(4-Isopropyl-phenylsulfamoyl)-4-oxo-1,4-dihydro-quinoline-3-carboxylic acid [2-(ethyl-phenyl-amino)-ethyl]-amide
(144) 2,3-Diethoxy-8-oxo-5,8,13,13a-tetrahydro-6H-isoquino[3,2-a]isoquinoline-13-carboxylic acid [3-(4-benzyl-piperidin-1-yl)-propyl]-amide
(145) 5-[1-(2-Chloro-benzyl)-2,4-dioxo-1,4-dihydro-2H-quinazolin-3-yl]-pentanoic acid 2-chloro-benzylamide
(146) 5-[1-(2-Chloro-benzyl)-2,4-dioxo-1,4-dihydro-2H-quinazolin-3-yl]-pentanoic acid [2-(4-chloro-phenyl)-ethyl]-amide
(147) 2-(3-Benzyl-4-oxo-6-piperidin-1-yl-3,4-dihydro-quinazolin-2-ylsulfanyl)-N-[2-(4-sulfamoyl-phenyl)-ethyl]-acetamide
(148) 4-[2-(7-Chloro-4-oxo-4H-pyrido[1,2-a]pyrimidin-2-ylmethylsulfanyl)-4-oxo-4H-quinazolin-3-ylmethyl]-cyclohexanecarboxylic acid 2-chloro-benzylamide
(149) 3-Benzyl-2-[2-(1-benzyl-1H-indol-3-yl)-vinyl]-3H-quinazolin-4-one
(150) 1-{3-[4-(4-Acetyl-phenyl)-piperazin-1-yl]-3-oxo-propyl}-4-phenethyl-4H-[1,2,4]triazolo[4,3-a]quinazolin-5-one
(151) N-(4-Methyl-benzyl)-2-[3-(3-{2-[(4-methyl-benzylcarbamoyl)-methylsulfanyl]-4-oxo-4H-quinazolin-3-yl}-propyl)-4-oxo-3,4-dihydro-quinazolin-2-ylsulfanyl]-acetamide
(152) 4-[4-Oxo-2-(2-oxo-2-phenyl-ethylsulfanyl)-4H-quinazolin-3-ylmethyl]-cyclohexanecarboxylic acid phenethyl-amide
(153) 4-Oxo-2-(2-oxo-2-phenyl-ethylsulfanyl)-3-phenyl-3,4-dihydro-quinazoline-7-carboxylic acid 3-chloro-benzylamide
(154) 3-Benzyl-4-oxo-2-(2-oxo-2-phenyl-ethylsulfanyl)-3,4-dihydro-quinazoline-7-carboxylic acid 3-chloro-benzylamide (155) 2-(3-Chloro-benzylsulfanyl)-4-oxo-3-pentyl-3,4-dihydro-quinazoline-7-carboxylic acid benzylamide (156) N-[2-(4-Chloro-phenyl)-ethyl]-4-[2,4-dioxo-1-(2,4,6-trimethyl-benzyl)-1,4-dihydro-2H-quinazolin-3-yl]-butyramide
(157) 3-(4-Methoxy-phenyl)-2,4-dioxo-1-(2,4,6-trimethyl-benzyl)-1,2,3,4-tetrahydro-quinazoline-7-carboxylic acid 4-methyl-benzylamide
(158) N-[2-(4-Chloro-phenyl)-ethyl]-3-[4-(4-fluoro-benzyl)-5-oxo-4,5-dihydro-[1,2,4]triazolo[4,3-a]quinazolin-1-yl]-propionamide
(159) 4-Oxo-2-(2-oxo-2-phenyl-ethylsulfanyl)-3-pentyl-3,4-dihydro-quinazoline-7-carboxylic acid 3-chloro-benzylamide
(160) 3-{4-[1,3-Dioxo-2-(2-trifluoromethyl-phenyl)-2,3-dihydro-1H-isoindol-5-yloxy]-phenyl}-4-oxo-3,4-dihydro-quinazoline-2-carboxylic acid ethyl ester
(161) 2-(3-Benzyl-4-oxo-3,4-dihydro-thieno[3,2-d]pyrimidin-2-ylsulfanyl)-N-[2-(4-sulfamoyl-phenyl)-ethyl]-acetamide
(162) 4-{2-[2-(4-Fluoro-phenyl)-2-oxo-ethylsulfanyl]-4-oxo-4H-quinazolin-3-ylmethyl}-cyclohexanecarboxylic acid 2-chloro-benzylamide
(163) 4-Oxo-2-(2-oxo-2-phenyl-ethylsulfanyl)-3-phenethyl-3,4-dihydro-quinazoline-7-carboxylic acid (3,5-dimethyl-phenyl)-amide (164) 2-[3-(2-Chloro-benzyl)-4-oxo-3,4-dihydro-benzo[4,5]thieno[3,2-d]pyrimidin-2-ylsulfanyl]-N-(4-methyl-benzyl)-acetamide
(165) 2-[2-(3,4-Dihydro-2H-quinolin-1-yl)-2-oxo-ethylsulfanyl]-3-phenethyl-3H-benzo[4,5]thieno[3,2-d]pyrimidin-4-one
(166) 6-{2-[2-(4-Chloro-phenyl)-2-oxo-ethylsulfanyl]-4-oxo-4H-thieno[3,2-d]pyrimidin-3-yl}-hexanoic acid 4-methyl-benzylamide
(167) 1,3-Diethyl-2-{3-ethyl-5-[2-(3-ethyl-3H-benzothiazol-2-ylidene)-ethylidene]-4-oxo-thiazolidin-2-ylidenemethyl}-6-trifluoromethanesulfonyl-3H-benzoimidazol-1-ium
(168) 4-(3-chlorobenzyl)-2-(1-(4-(2-methoxyphenyl)piperazin-1-yl)-1-oxopropan-2-yl)-2H-benzo[b][1,4]thiazin-3(4H)-one
(169) 1-Benzyl-7-diethylamino-3-(2,4-dimethyl-benzenesulfonyl)-6-fluoro-1H-quinolin-4-one
(170) 1-Benzyl-3-(2,4-dimethyl-benzenesulfonyl)-6-fluoro-7-pyrrolidin-1-yl-1H-quinolin-4-one In one embodiment of formula (II), (III), or (IV), X—Z is —C═C— and Y—Z is —N—C—, or —CH—CH—.

In one embodiment of formula (II), (III), or (IV), X—Z is —N—C— and Y—Z is —N—C—, —N═C—, or —CH—CH—.

In one embodiment of formula (II), (III), or (IV), $R^1$ is —NH—S(O)$_k$R$^5$, alkyl, substituted alkyl, cycloalkylalkyl, substituted cycloalkylalkyl, cycloheteroalkylalkyl, substituted cycloheteroalkylalkyl, heteroarylalkyl, substituted heteroarylalkyl, heteroalkyl, substituted heteroalkyl or —CONR$^6$R$^7$.

In one embodiment of formula (II), (III), or (IV), $R^2$ is hydrogen, ═O, —NR$^{21}$COR$^{18}$, —NR$^{19}$R$^{20}$, alkoxycarbonyl, substituted alkoxycarbonyl, alkyl, substituted alkyl, heteroaryl, substituted heteroaryl, heteroarylalkyl, substituted heteroarylalkyl or alternatively $R^1$ and $R^2$ along with the atoms to which they are attached form a fused indanoyl or substituted fused indanoyl ring.

In one embodiment of formula (II), (III), or (IV), $R^3$ is alkyl, substituted alkyl, heteroarylalkyl, substituted heteroarylalkyl, —CONR$^8$R$^9$ or alternatively $R^2$ and $R^3$ along with the atoms to which they are attached form a heteroaryl or substituted heteroaryl ring.

In one embodiment of formula (II), (III), or (IV), $R^1$ is —NH—S(O)$_k$R$^5$, alkyl, substituted alkyl, cycloalkylalkyl, substituted cycloalkylalkyl, cycloheteroalkylalkyl, substituted cycloheteroalkylalkyl, heteroarylalkyl, substituted heteroarylalkyl, heteroalkyl, substituted heteroalkyl or —CONR$^6$R$^7$ and $R^2$ is hydrogen, ═O, —NR$^{21}$COR$^{18}$, —NR$^{19}$R$^{20}$, alkoxycarbonyl, substituted alkoxycarbonyl, alkyl, substituted alkyl, heteroaryl, substituted heteroaryl, heteroarylalkyl, substituted heteroarylalkyl or alternatively $R^1$ and $R^2$ along with the atoms to which they are attached form a fused indanoyl or substituted fused indanoyl ring.

In one embodiment of formula (II), (III), or (IV), $R^1$ is —NH—S(O)$_k$R$^5$, alkyl, substituted alkyl, cycloalkylalkyl, substituted cycloalkylalkyl, cycloheteroalkylalkyl, substituted cycloheteroalkylalkyl, heteroarylalkyl, substituted heteroarylalkyl, heteroalkyl, substituted heteroalkyl or —CONR$^6$R$^7$ and $R^3$ is alkyl, substituted alkyl, heteroarylalkyl, substituted heteroarylalkyl, —CONR$^8$R$^9$ or alternatively $R^2$ and $R^3$ along with the atoms to which they are attached form a heteroaryl or substituted heteroaryl ring.

In one embodiment of formula (II), (III), or (IV), $R^1$ is —NH—S(O)$_k$R$^5$, alkyl, substituted alkyl, cycloalkylalkyl, substituted cycloalkylalkyl, cycloheteroalkylalkyl, substituted cycloheteroalkylalkyl, heteroarylalkyl, substituted heteroarylalkyl, heteroalkyl, substituted heteroalkyl or —CONR$^6$R$^7$, $R^2$ is hydrogen, ═O, —NR$^{21}$COR$^{18}$, —NR$^{19}$R$^{20}$, alkoxycarbonyl, substituted alkoxycarbonyl, alkyl, substituted alkyl, heteroaryl, substituted heteroaryl, heteroarylalkyl, substituted heteroarylalkyl or alternatively $R^1$ and $R^2$ along with the atoms to which they are attached form a fused indanoyl or substituted fused indanoyl ring and $R^3$ is alkyl, substituted alkyl, heteroarylalkyl, substituted heteroarylalkyl, —CONR$^8$R$^9$ or alternatively $R^2$ and $R^3$ along with the atoms to which they are attached form a heteroaryl or substituted heteroaryl ring.

In one embodiment of formula (II), (III), or (IV), the compound can be represented by a structural formula (V), (VI), (VII), (VIII), (IX), (X) or (XI):

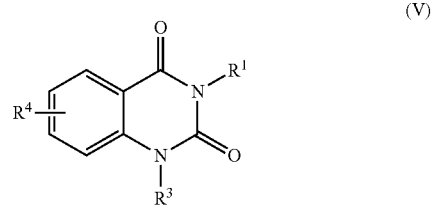

(V)

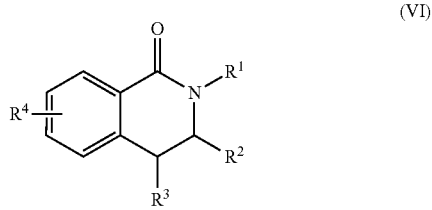

(VI)

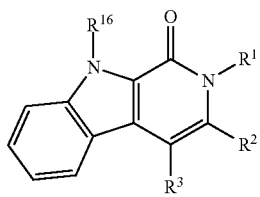 (VII)

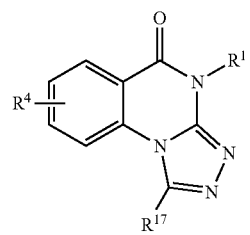 (VIII)

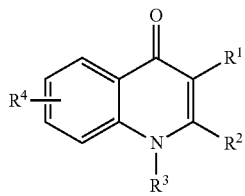 (IX)

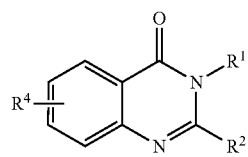 (X)

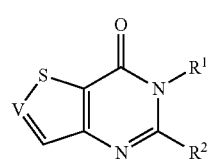 (XI)

wherein $R^1$, $R^2$, $R^3$, $R^4$, and $R^{16}$ are the same as defined in structural formulae (II), (III) and (IV);

$R^{17}$ is hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl.

In one embodiment of formula (II), (III), or (IV), the compound is selected from the group consisting of

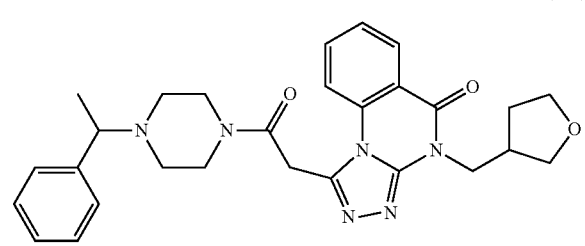 (181)

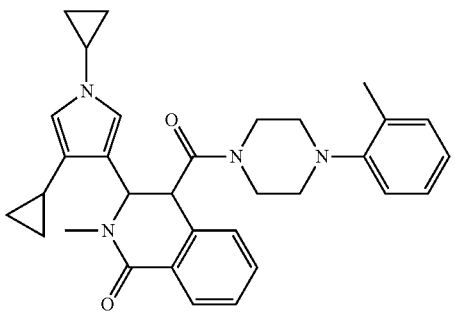 (182)

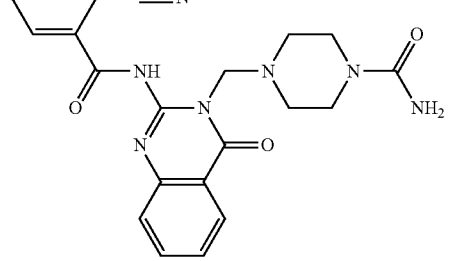 (183)

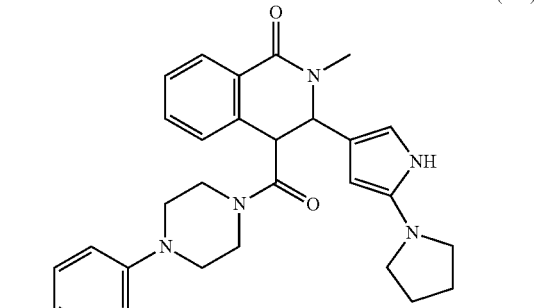 (184)

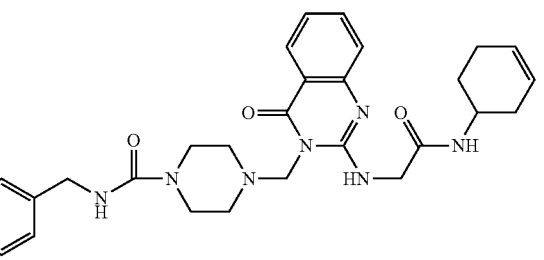 (185)

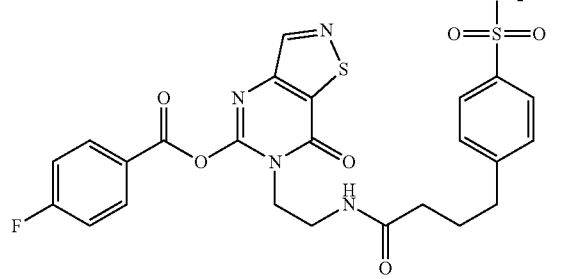 (186)

(187)
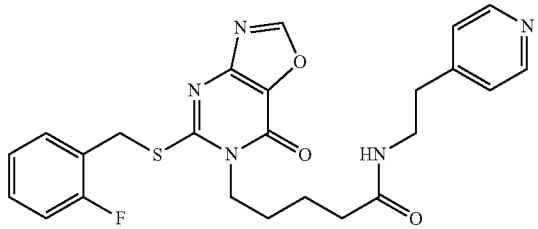

(188)
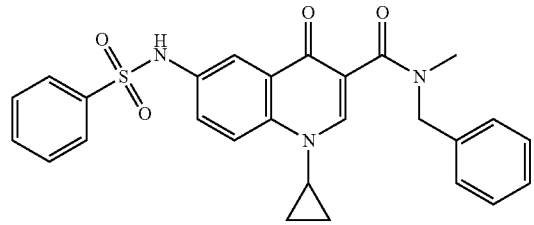

(189)
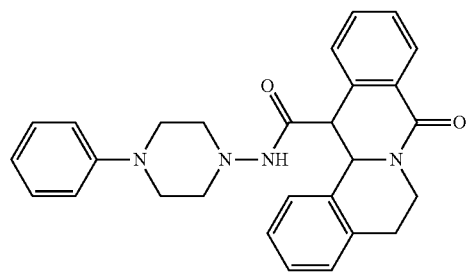

(190)
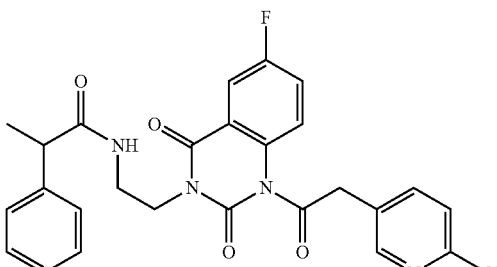

(191)
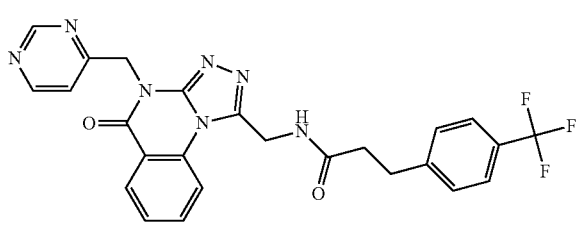

(192)
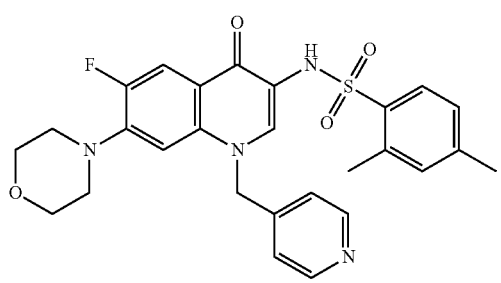

(193)
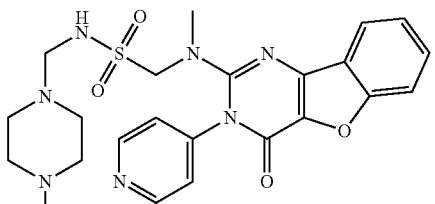

(194)
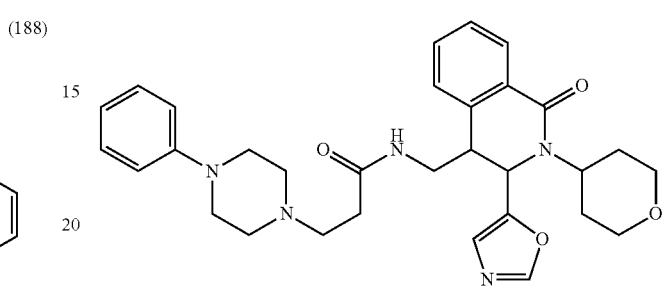

or the salt, solvate, ester, and/or prodrug thereof.

The above-listed compounds may also be represented by their chemical names as follows:

(181) 1-{2-Oxo-2-[4-(1-phenyl-ethyl)-piperazin-1-yl]-ethyl}-4-(tetrahydro-furan-3-ylmethyl)-4H-[1,2,4]triazolo[4,3-a]quinazolin-5-one (182) 3-(1,4-Dicyclopropyl-1H-pyrrol-3-yl)-2-methyl-4-(4-o-tolyl-piperazine-1-carbonyl)-3,4-dihydro-2H-isoquinolin-1-one (183) 4-[2-(2-Cyano-benzoylamino)-4-oxo-4H-quinazolin-3-ylmethyl]-piperazine-1-carboxylic acid amide (184) 4-[4-(4-Chloro-phenyl)-piperazine-1-carbonyl]-2-methyl-3-(2,3,4,5-tetrahydro-1'H-[1,2']bipyrrolyl-4'-yl)-3,4-dihydro-2H-isoquinolin-1-one (185) 4-{2-[(Cyclohex-3-enylcarbamoylmethyl)-amino]-4-oxo-4H-quinazolin-3-ylmethyl}-piperazine-1-carboxylic acid benzylamide (186) 4-Fluoro-benzoic acid 7-oxo-6-{2-[4-(4-sulfamoyl-phenyl)-butyrylamino]-ethyl}-6,7-dihydro-isothiazolo[4,5-d]pyrimidin-5-yl ester (187) 5-[5-(2-Fluoro-benzylsulfanyl)-7-oxo-7H-oxazolo[4,5-d]pyrimidin-6-yl]-pentanoic acid (2-pyridin-4-yl-ethyl)-amide (188) 6-Benzenesulfonylamino-1-cyclopropyl-4-oxo-1,4-dihydro-quinoline-3-carboxylic acid benzyl-methyl-amide (189) 8-Oxo-5,8,13,13a-tetrahydro-6H-isoquino[3,2-a]isoquinoline-13-carboxylic acid (4-phenyl-piperazin-1-yl)-amide (190) N-(2-{1-[2-(6-Chloro-pyridin-3-yl)-acetyl]-6-fluoro-2,4-dioxo-1,4-dihydro-2H-quinazolin-3-yl}-ethyl)-2-phenyl-propionamide (191) N-(5-Oxo-4-pyrimidin-4-ylmethyl-4,5-dihydro-[1,2,4]triazolo[4,3-a]quinazolin-1-ylmethyl)-3-(4-trifluoromethyl-phenyl)-propionamide (192) N-(6-Fluoro-7-morpholin-4-yl-4-oxo-1-pyridin-4-ylmethyl-1,4-dihydro-quinolin-3-yl)-2,4-dimethyl-benzenesulfonamide (193) N-(4-Methyl-piperazin-1-ylmethyl)-C-(4-oxo-3-pyridin-4-ylmethyl-3,4-dihydro-benzo[4,5]furo[3,2-d]pyrimidin-2-ylamino)-methanesulfonamide (194) N-[3-Oxazol-5-yl-1-oxo-2-(tetrahydro-pyran-4-yl)-1,2,3,4-tetrahydro-isoquinolin-4-ylmethyl]-3-(4-phenyl-piperazin-1-yl)-propionamide In another aspect, the present invention provides a pharmaceutical composition comprising a compound having a structural formula (II), (III) or (IV), or a salt, solvate, ester, and/or prodrug thereof,

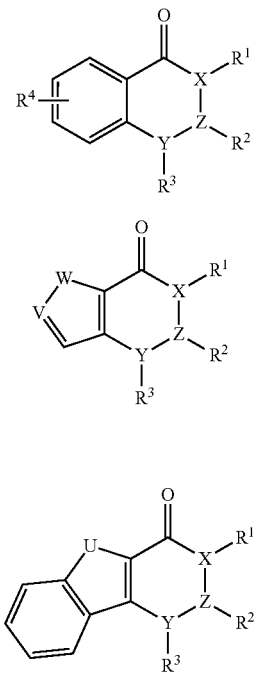

wherein:
X—Z is —C=C— or —N=C—;
Y—Z is —N—C—, —N=C—, —CH—CH— or —S—CH—;
provided that X—Z is not —C=C— when Y—Z is —N=C—;
$R^1$ is —S(O)$_k$R$^5$, —NH—S(O)$_k$R$^5$, alkyl, substituted alkyl, aryl, substituted aryl, arylalkyl, substituted arylalkyl, cycloalkylalkyl, substituted cycloalkylalkyl, cycloheteroalkylalkyl, substituted cycloheteroalkylalkyl, heteroaryl, substituted heteroaryl, heteroarylalkyl, substituted heteroarylalkyl, heteroalkyl, substituted heteroalkyl, —CONR$^6$R$^7$ or alternatively $R^1$ and $R^2$ along with the atoms to which they are attached form a cycloalkyl, substituted cycloalkyl, cycloheteroalkyl, substituted cycloheteroalkyl, aryl, substituted aryl, heteroaryl, substituted heteroaryl ring, fused indanoyl or substituted fused indanoyl ring;
k is 0, 1 or 2;
$R^2$ is hydrogen, —S(O)$_l$R$^8$, =O, —NR$^{21}$COR$^{18}$, —NR$^{19}$R$^{20}$, alkoxycarbonyl, substituted alkoxycarbonyl, alkyl, substituted alkyl, aryl, substituted aryl, arylalkyl, substituted arylalkyl, heteroaryl, substituted heteroaryl, heteroarylalkyl, substituted heteroarylalkyl or alternatively $R^2$ and $R^3$ along with the atoms to which they are attached form a cycloalkyl, substituted cycloalkyl, cycloheteroalkyl, substituted cycloheteroalkyl, aryl, substituted aryl, heteroaryl or substituted heteroaryl ring;
l is 0, 1 or 2;
$R^3$ is hydrogen, alkyl, substituted alkyl, arylalkyl, substituted arylalkyl, heteroaryl, substituted heteroaryl, heteroarylalkyl, substituted heteroarylalkyl, heteroalkyl, substituted heteroalkyl or —CONR$^8$R$^9$ when Y—Z is —N—C—, or —CH—CH— and is not defined when Y—Z is —N=C—;
provided that $R^2$ does not form a ring with both $R^1$ and $R^3$;

$R^4$ is alkyl, acyl, substituted acyl, acyloxycarbonyl, substituted acyloxycarbonyl, aryloxycarbonyl, substituted aryloxycarbonyl, alkoxy, substituted alkoxy, alkyl, substituted alkyl, arylalkyl, substituted arylalkyl, heteroaryl, substituted heteroaryl, heteroarylalkyl, substituted heteroarylalkyl, heteroalkyl, substituted arylalkyl, halo, hydroxyl, nitro, cyano, —CONR$^{10}$R$^{11}$, —NR$^{12}$R$^{13}$, carboxyl or —S(O)$_m$R$^{14}$;
m is 0, 1 or 2;
$R^5$, $R^8$ and $R^{14}$ are independently alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;
$R^6$ and $R^7$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively $R^6$ and $R^7$ along with the atoms to which they are attached form a cycloheteroalkyl or substituted cycloheteroalkyl, ring;
$R^8$ and $R^9$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively $R^8$ and $R^9$ along with the atoms to which they are attached form a cycloheteroalkyl or substituted cycloheteroalkyl, ring;
$R^{10}$ and $R^{11}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively $R^{10}$ and $R^{11}$ along with the atoms to which they are attached form a cycloheteroalkyl or substituted cycloheteroalkyl, ring;
$R^{12}$ and $R^{13}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl or alternatively $R^{12}$ and $R^{13}$ along with the atoms to which they are attached form a cycloheteroalkyl or substituted cycloheteroalkyl, ring;
W is —O—, —NR$^{15}$ or —S—;
U is —O—, —NR$^{16}$ or —S—;
V is —CH— or —N—;
$R^{15}$ and $R^{16}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;
$R^{18}$ and $R^{21}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl; and
$R^{19}$ and $R^{20}$ are independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;
provided that Formula (II), (III), or (IV) does not include 3-{2-[4-(4-Fluoro-benzoyl)-piperidin-1-yl]-ethyl}-1H-quinazoline-2,4-dione; and
a pharmaceutically acceptable vehicle.

In one embodiment of the pharmaceutical composition, the compound having a structural Formula (II), (III) or (IV) is selected from the group consisting of

101                                         102
(101)                                         (102)
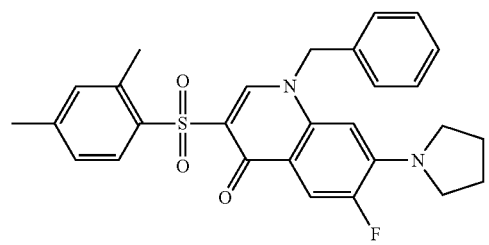                          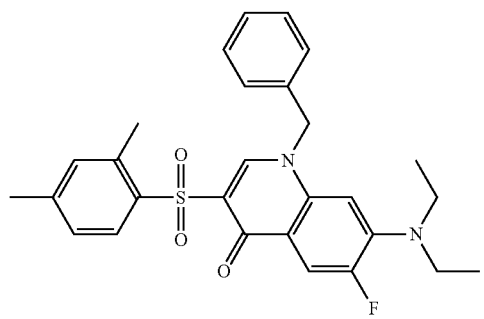
(103)                                         (104)
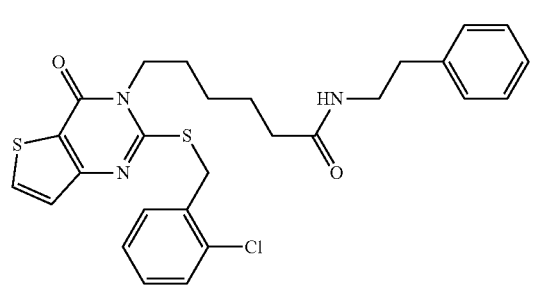                          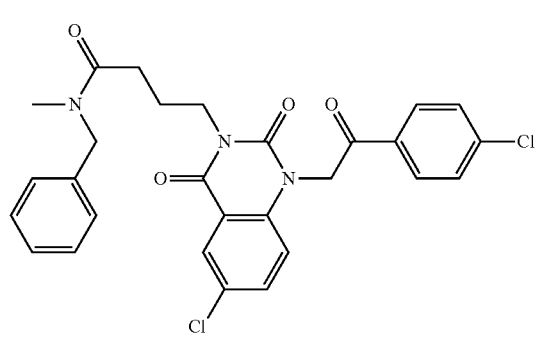
(105)                                         (106)
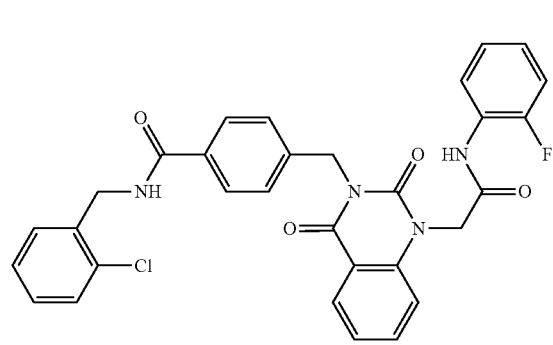                          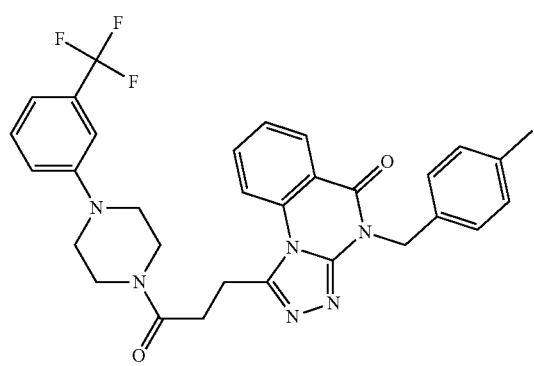
(107)                                         (108)
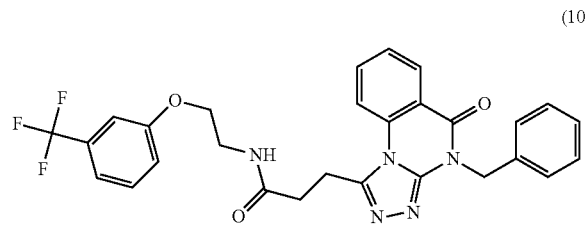                          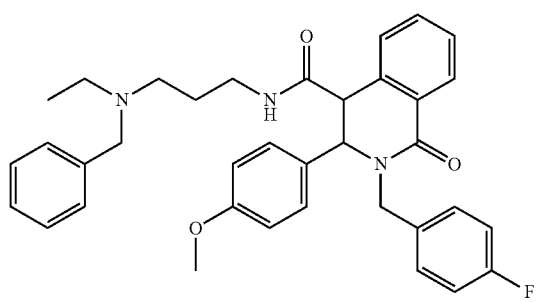

-continued
(109)
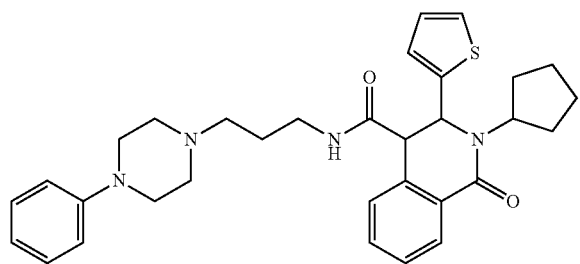
(110)
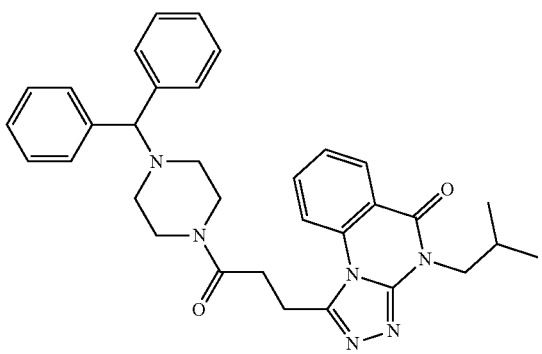
(111)
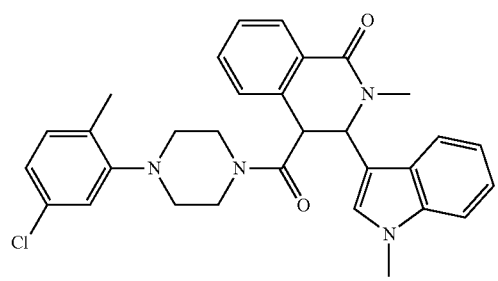
(112)
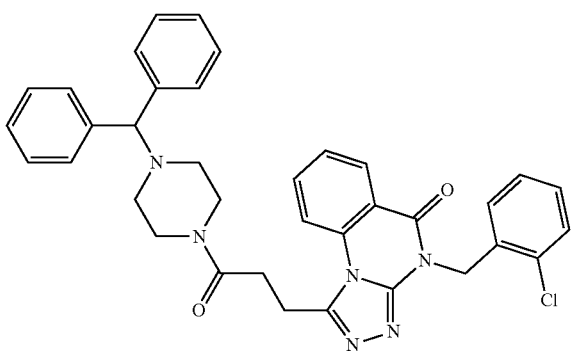
(113)
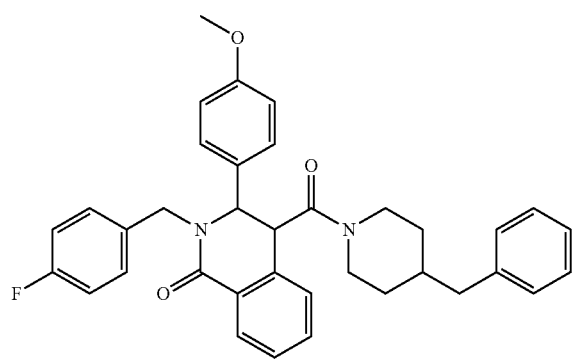
(114)
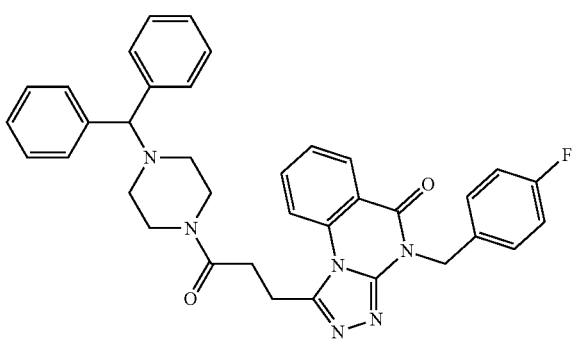
(115)
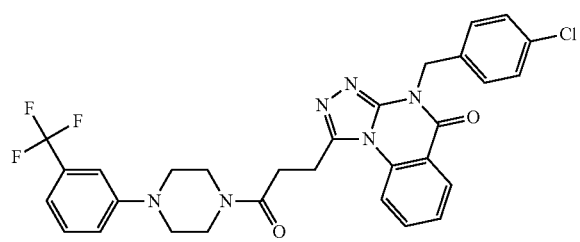
(116)
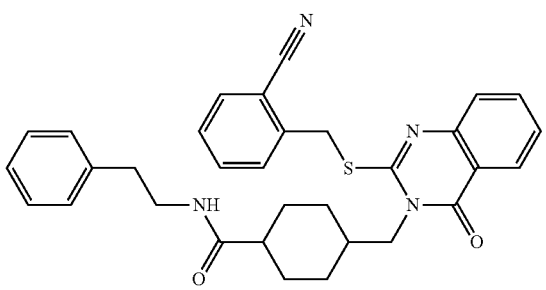

-continued
(117)
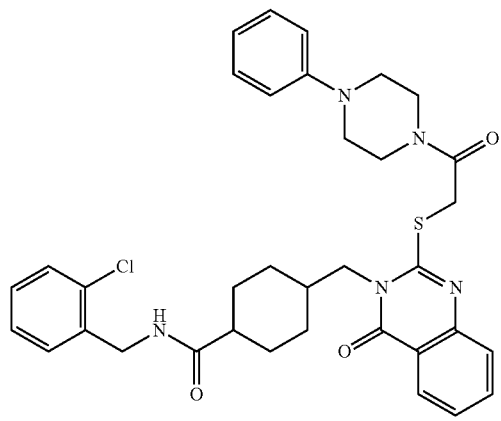
(118)
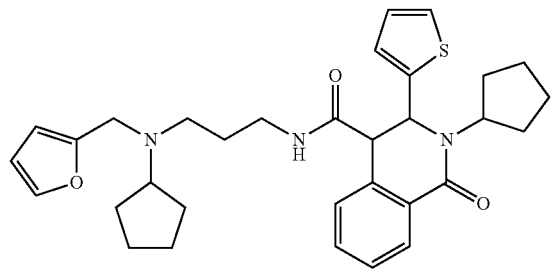
(119)
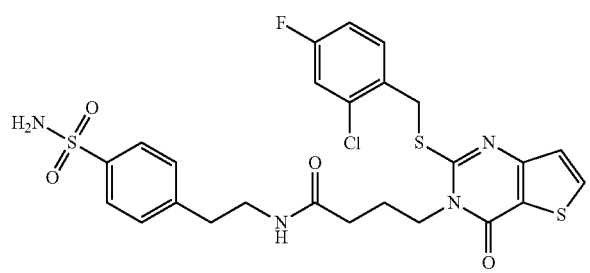
(120)
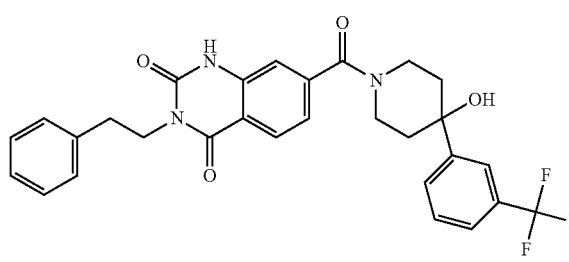
(121)
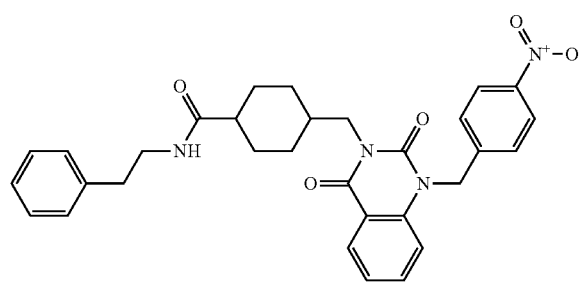
(122)
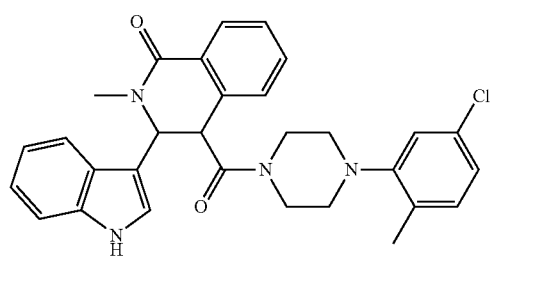
(123)
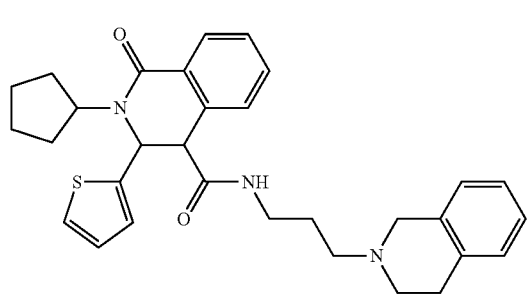
(124)
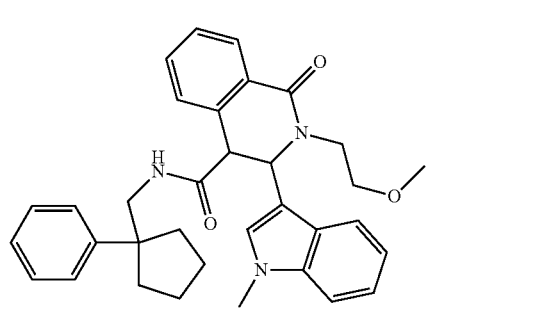
(125)
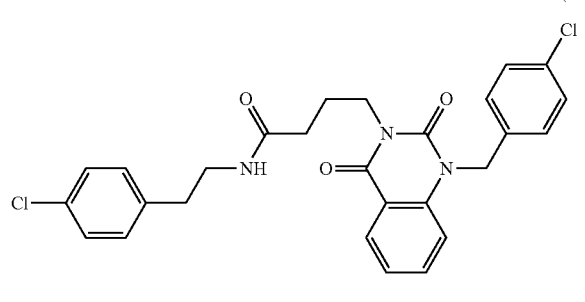
(126)
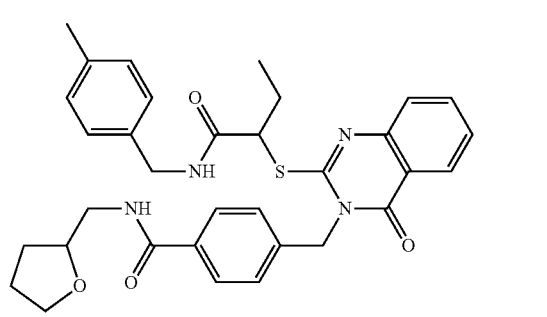

-continued
(127)
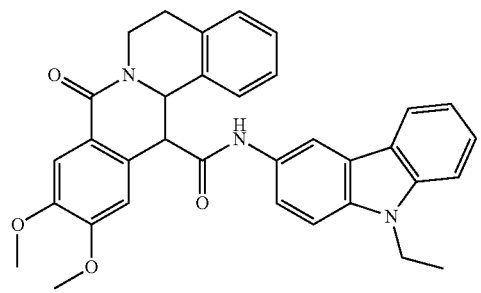
(128)
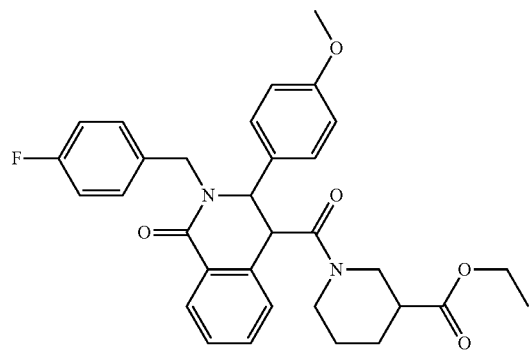
(129)
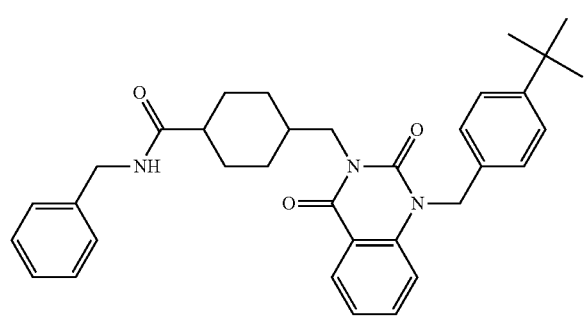
(130)
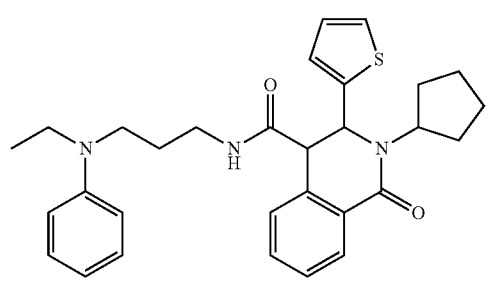
(131)
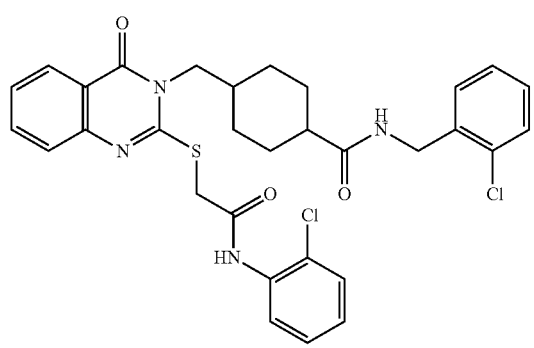
(132)
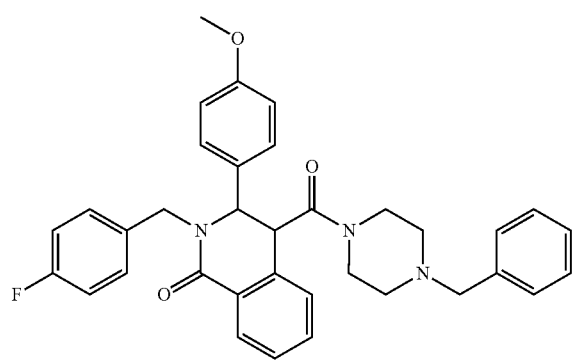
(133)
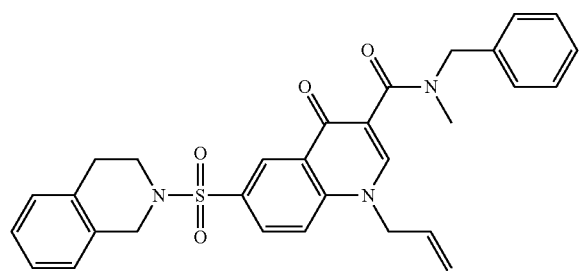
(134)
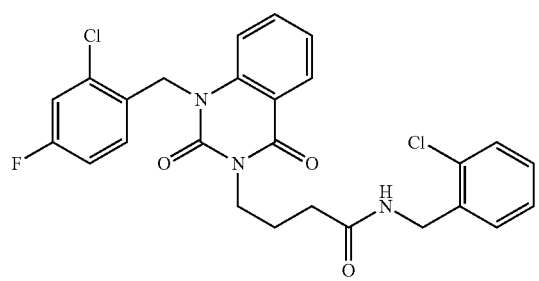

-continued
(135)
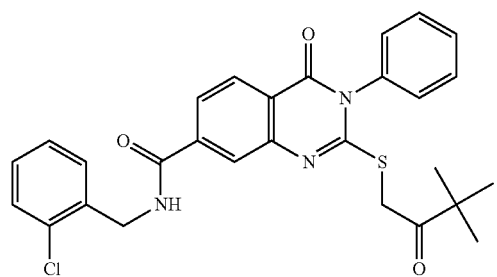
(136)
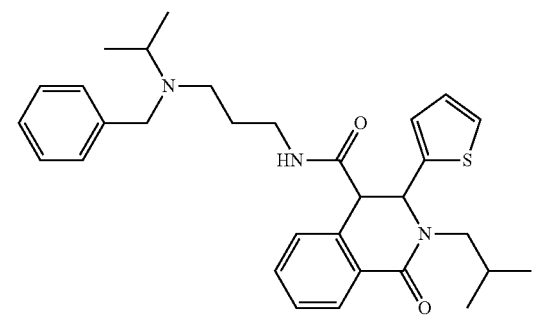
(137)
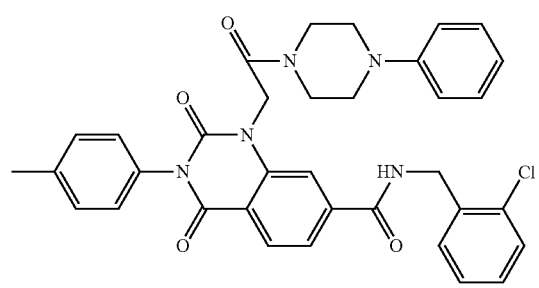
(138)
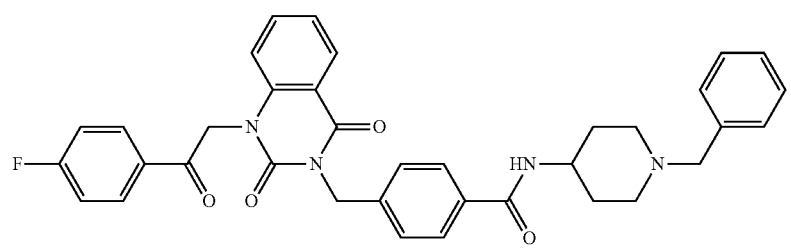
(139)
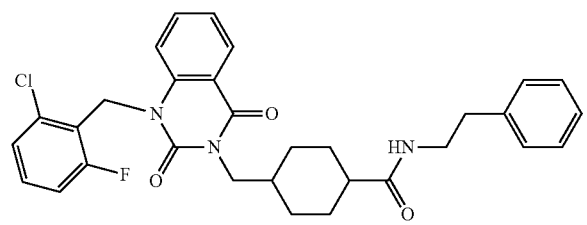
(140)
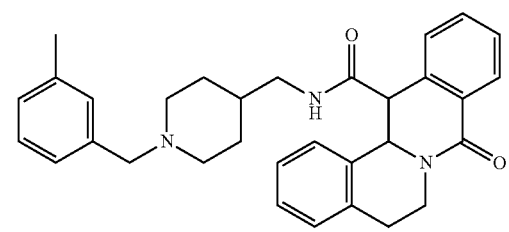
(141)
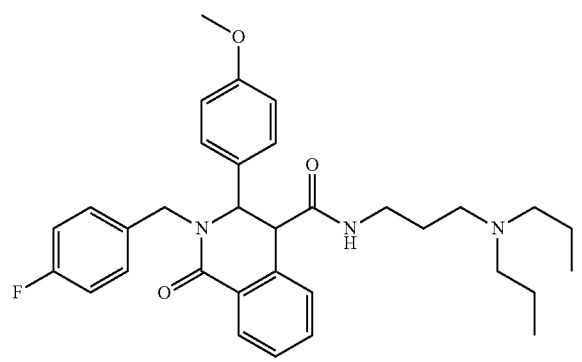
(142)
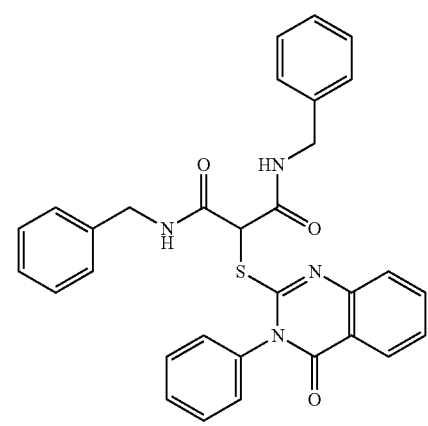

111
112
-continued
(143)
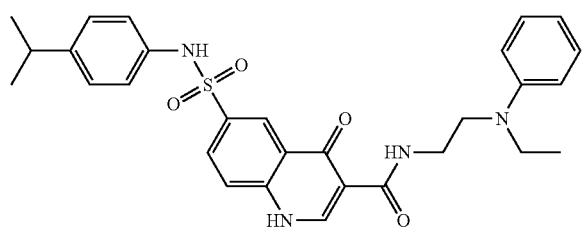
(144)
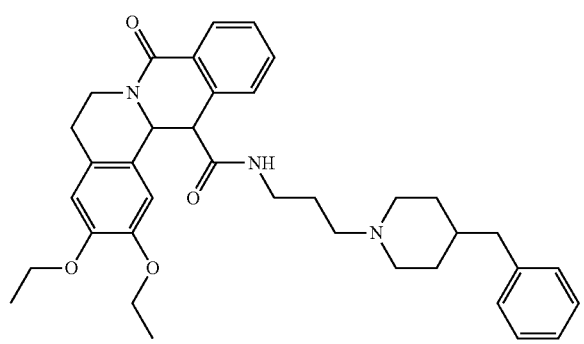
(145)
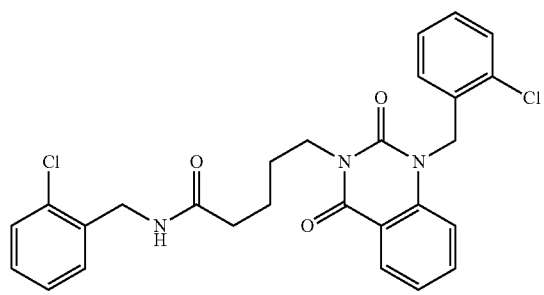
(146)
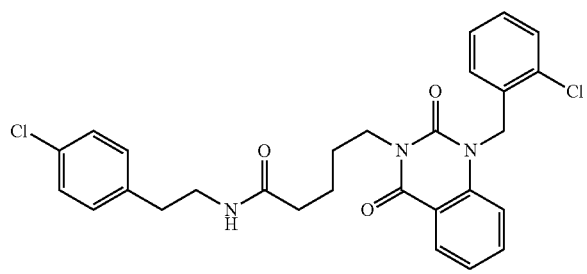
(147)
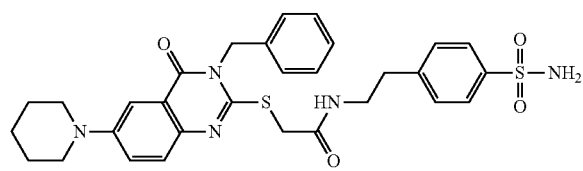
(148)
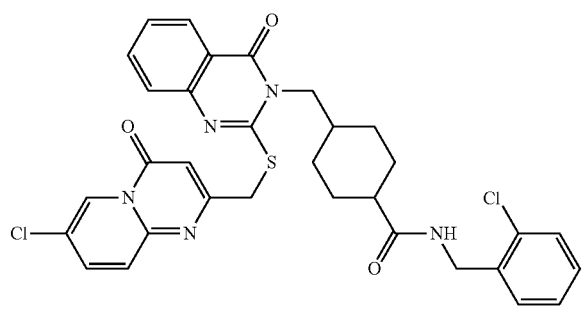
(149)
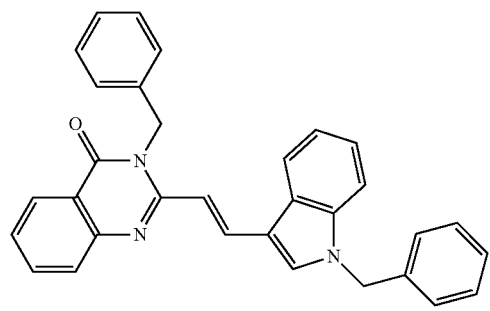
(150)
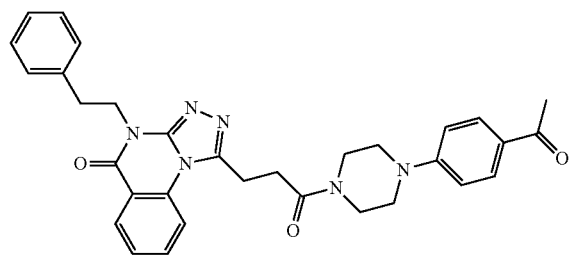

-continued
(151)
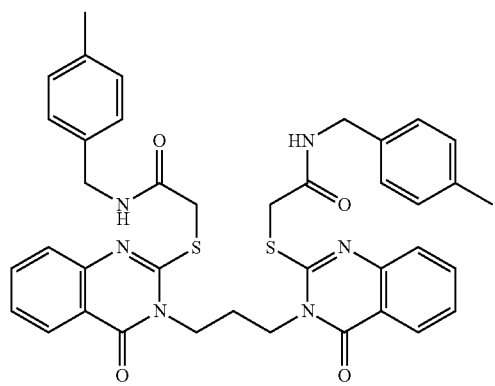
(152)
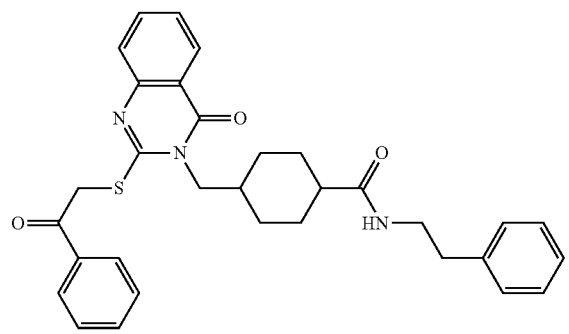
(153)
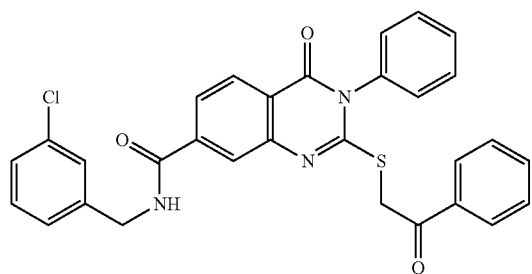
(154)
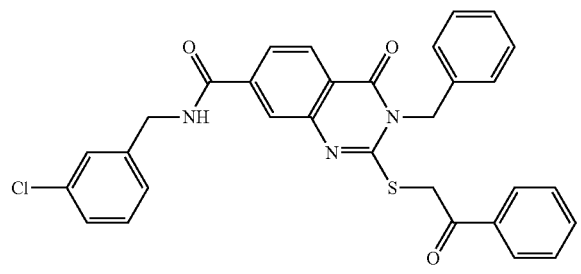
(155)
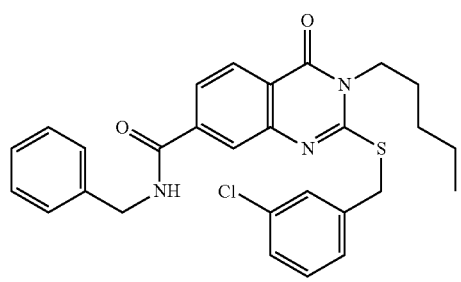
(156)
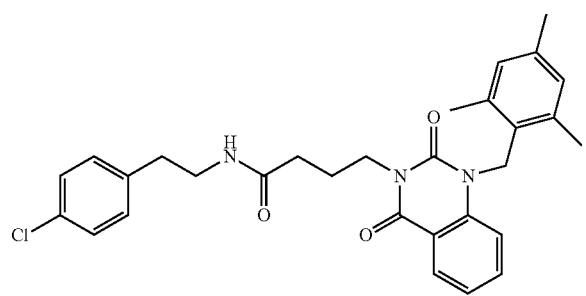
(157)
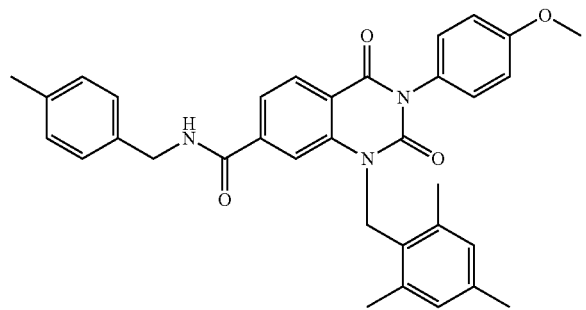
(158)
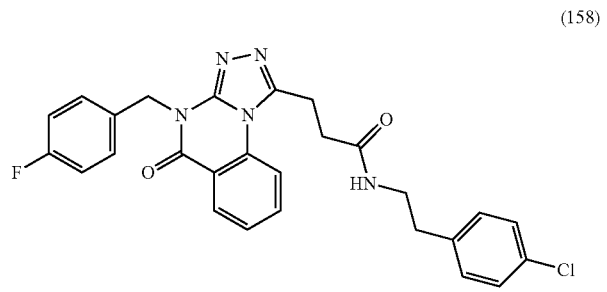

-continued
(159)
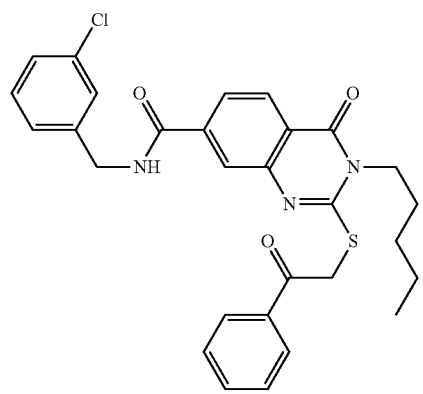
(160)
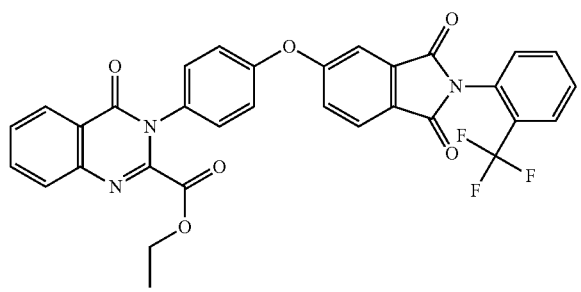
(161)
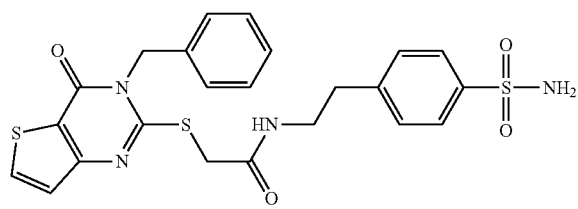
(162)
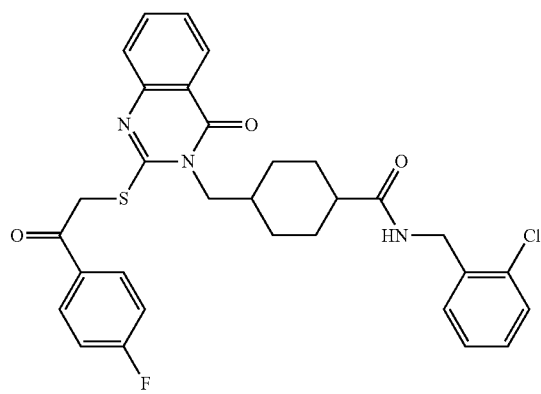
(163)
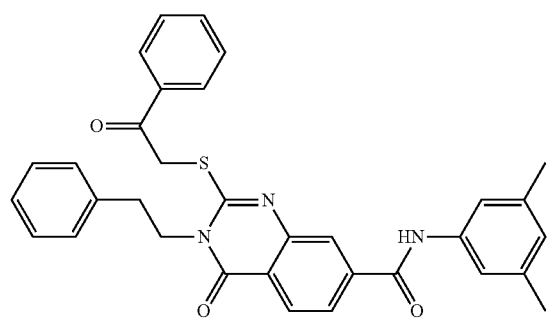
(164)
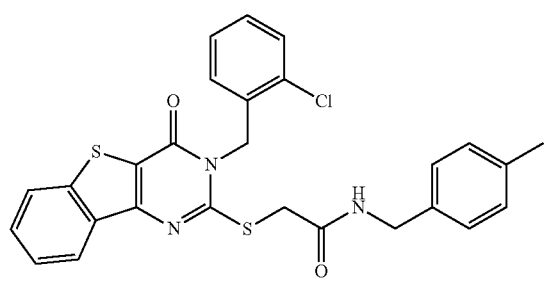
(165)
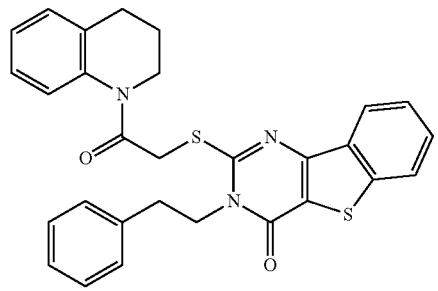
(166)
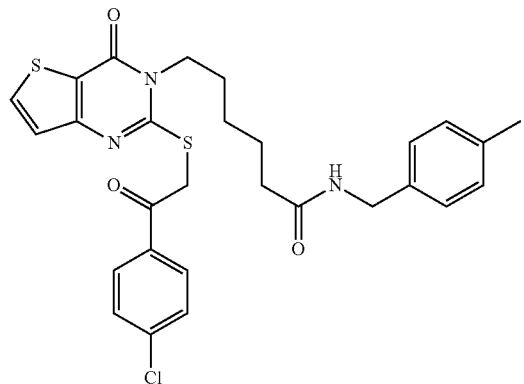

-continued
(167)
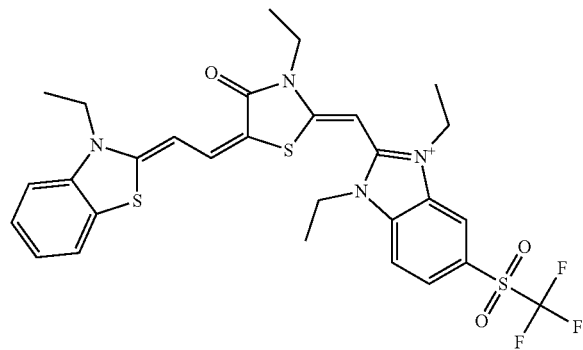
(168)
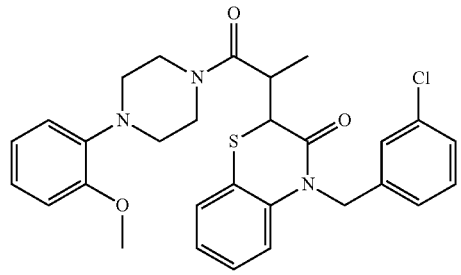
(169)
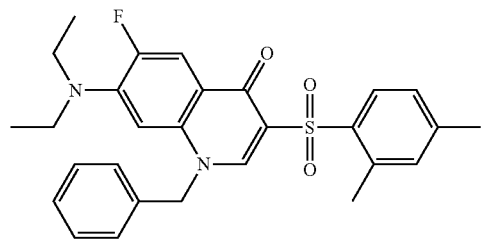
(170)
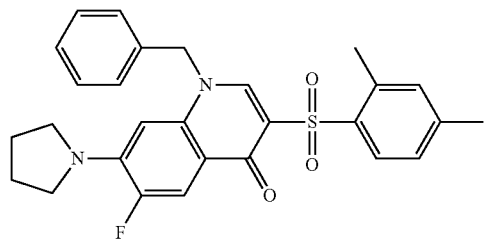
(181)
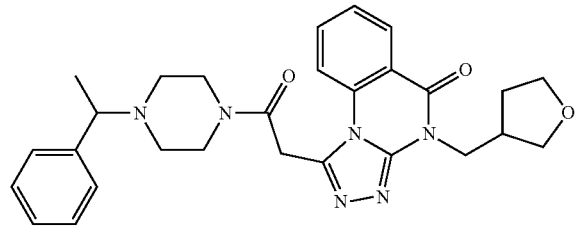
(182)
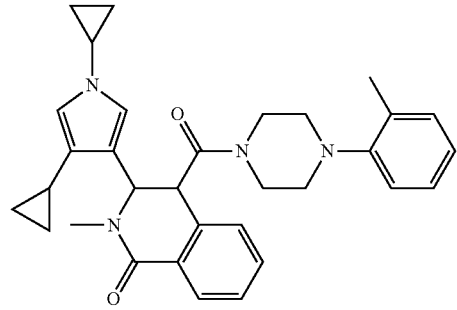
(183)
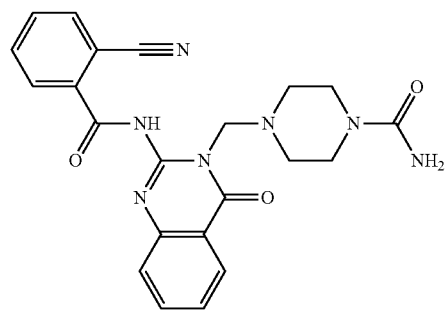
(184)
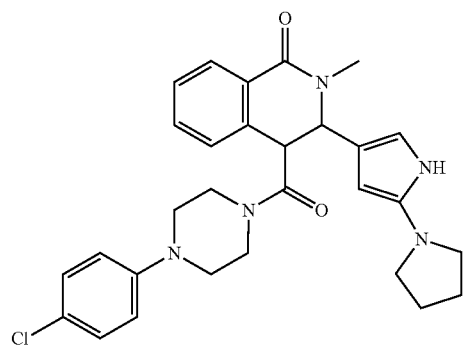
(185)
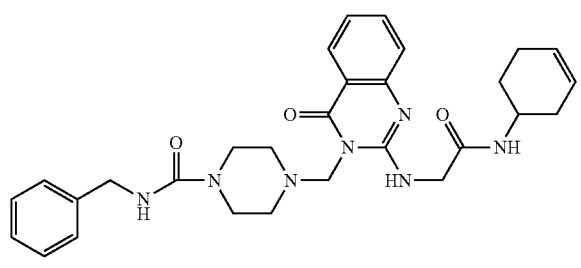
(186)
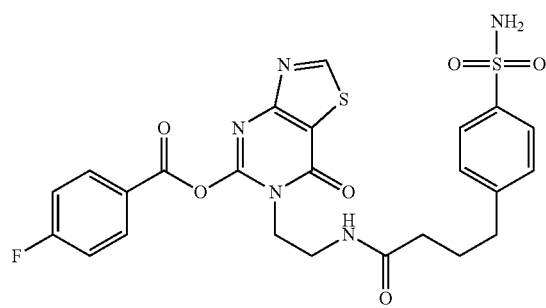

-continued (187) 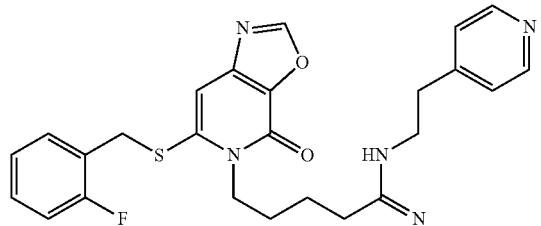

(188) 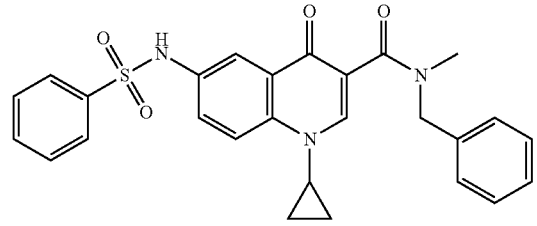

(189) 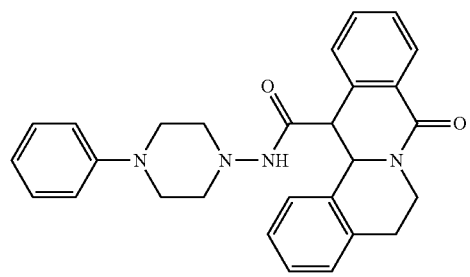

(190) 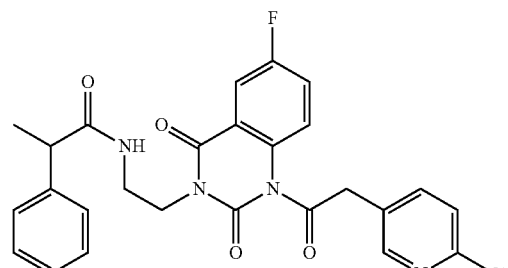

(191) 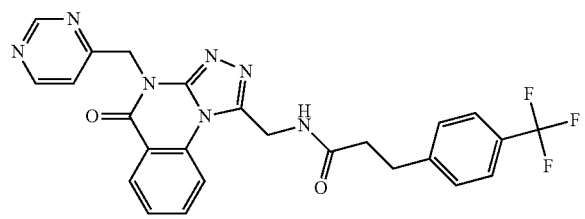

(192) 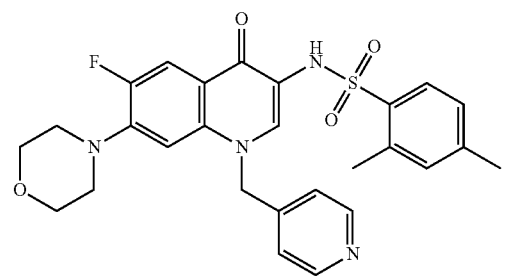

(193) 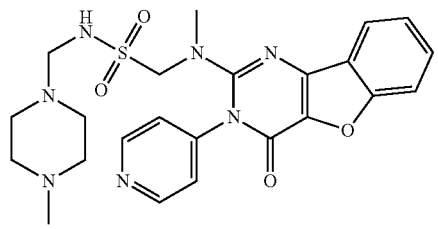

(194) 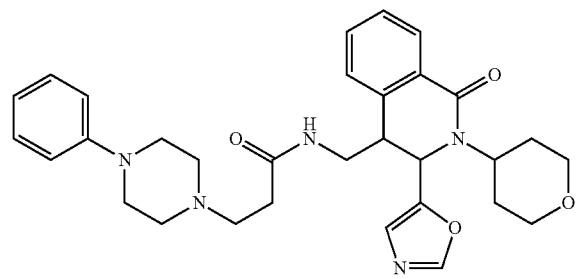

or the salt, solvate, ester, and/or prodrug thereof.

The above-listed compounds may also be represented by their chemical names as follows:

(101) 3-(2,4-dimethylphenylsulfonyl)-1-benzyl-6-fluoro-7-(pyrrolidin-1-yl)quinolin-4(1H)-one
(102) 3-(2,4-dimethylphenylsulfonyl)-1-benzyl-7-(diethylamino)-6-fluoroquinolin-4(1H)-one
(103) 6-(2-(2-chlorobenzylthio)-4-oxothieno[3,2-d]pyrimidin-3(4H)-yl)-N-phenethylhexanamide
(104) N-Benzyl-4-{6-chloro-1-[2-(4-chloro-phenyl)-2-oxo-ethyl]-2,4-dioxo-1,4-dihydro-2H-quinazolin-3-yl}-N-methyl-butyramide
(105) N-(2-Chloro-benzyl)-4-{1-[(2-fluoro-phenylcarbamoyl)-methyl]-2,4-dioxo-1,4-dihydro-2H-quinazolin-3-ylmethyl}-benzamide
(106) 4-(4-Methyl-benzyl)-1-{3-oxo-3-[4-(3-trifluoromethyl-phenyl)-piperazin-1-yl]-propyl}-4H-[1,2,4]triazolo[4,3-a]quinazolin-5-one
(107) 3-(4-Benzyl-5-oxo-4,5-dihydro-[1,2,4]triazolo[4,3-a]quinazolin-1-yl)-N-[2-(3-trifluoromethyl-phenoxy)-ethyl]-propionamide
(108) 2-(4-Fluoro-benzyl)-3-(4-methoxy-phenyl)-1-oxo-1,2,3,4-tetrahydro-isoquinoline-4-carboxylic acid [3-(benzyl-ethyl-amino)-propyl]-amide
(109) 2-Cyclopentyl-1-oxo-3-thiophen-2-yl-1,2,3,4-tetrahydro-isoquinoline-4-carboxylic acid [3-(4-phenyl-piperazin-1-yl)-propyl]-amide
(110) 1-[3-(4-Benzhydryl-piperazin-1-yl)-3-oxo-propyl]-4-isobutyl-4H-[1,2,4]triazolo[4,3-a]quinazolin-5-one
(111) 4-[4-(5-Chloro-2-methyl-phenyl)-piperazine-1-carbonyl]-2-methyl-3-(1-methyl-1H-indol-3-yl)-3,4-dihydro-2H-isoquinolin-1-one
(112) 1-[3-(4-Benzhydryl-piperazin-1-yl)-3-oxo-propyl]-4-(2-chloro-benzyl)-4H-[1,2,4]triazolo[4,3-a]quinazolin-5-one
(113) 4-(Benzyl-piperidine-1-carbonyl)-2-(4-fluoro-benzyl)-3-(4-methoxy-phenyl)-3,4-dihydro-2H-1-isoquinolin-1-one (114) 1-[3-(4-Benzhydryl-piperazin-1-yl)-3-oxo-propyl]-4-(4-fluoro-benzyl)-4H-[1,2,4]triazolo[4,3-a]quinazolin-5-one
(115) 4-(4-Chloro-benzyl)-1-{3-oxo-3-[4-(3-trifluoromethyl-phenyl)-piperazin-1-yl]-propyl}-4H-[1,2,4]triazolo[4,3-a]quinazolin-5-one
(116) 4-[2-(2-Cyano-benzylsulfanyl)-4-oxo-4H-quinazolin-3-ylmethyl]-cyclohexanecarboxylic acid phenethyl-amide
(117) 4-{4-oxo-2-[2-oxo-2-(4-phenyl-piperazin-1-yl)-ethylsulfanyl]-4H-quinazolin-3-ylmethyl}-cyclohexanecarboxylic acid 2-chloro-benzylamide
(118) 2-Cyclopentyl-1-oxo-3-thiophen-2-yl-1,2,3,4-tetrahydro-isoquinoline-4-carboxylic acid [3-(cyclopentyl-furan-2-ylmethyl-amino)-propyl]-amide
(119) 4-[2-(2-Chloro-4-fluoro-benzylsulfanyl)-4-oxo-4H-thieno[3,2-d]pyrimidin-3-yl]-N-[2-(4-sulfamoyl-phenyl)-ethyl]-butyramide
(120) 7-[4-Hydroxy-4-(3-trifluoromethyl-phenyl)-piperidine-1-carbonyl]-3-phenethyl-1H-quinazoline-2,4-dione
(121) 4-[1-(4-Nitro-benzyl)-2,4-dioxo-1,4-dihydro-2H-quinazolin-3-ylmethyl]-cyclohexanecarboxylic acid phenethyl-amide
(122) 4-[4-(5-Chloro-2-methyl-phenyl)-piperazine-1-carbonyl]-3-(1H-indol-3-yl)-2-methyl-3,4-dihydro-2H-isoquinolin-1-one
(123) 2-Cyclopentyl-1-oxo-3-thiophen-2-yl-1,2,3,4-tetrahydro-isoquinoline-4-carboxylic acid [3-(3,4-dihydro-1H-1-isoquinolin-2-yl)-propyl]-amide
(124) 2-(2-Methoxy-ethyl)-3-(1-methyl-1H-indol-3-yl)-1-oxo-1,2,3,4-tetrahydro-isoquinoline-4-carboxylic acid (1-phenyl-cyclopentylmethyl)-amide
(125) 4-[1-(4-Chloro-benzyl)-2,4-dioxo-1,4-dihydro-2H-quinazolin-3-yl]-N-[2-(4-chloro-phenyl)-ethyl]-butyramide
(126) 4-{2-[1-(4-Methyl-benzylcarbamoyl)-propylsulfanyl]-4-oxo-4H-quinazolin-3-ylmethyl}-N-(tetrahydro-furan-2-ylmethyl)-benzamide
(127) 10,11-Dimethoxy-8-oxo-5,8,13,13a-tetrahydro-6H-isoquino[3,2-a]isoquinoline-13-carboxylic acid (9-ethyl-9H-carbazol-3-yl)-amide
(128) 1-[2-(4-Fluoro-benzyl)-3-(4-methoxy-phenyl)-1-oxo-1,2,3,4-tetrahydro-isoquinoline-4-carbonyl]-piperidine-3-carboxylic acid ethyl ester
(129) 4-[1-(4-tert-Butyl-benzyl)-2,4-dioxo-1,4-dihydro-2H-quinazolin-3-ylmethyl]-cyclohexanecarboxylic acid benzylamide
(130) 2-Cyclopentyl-1-oxo-3-thiophen-2-yl-1,2,3,4-tetrahydro-isoquinoline-4-carboxylic acid [3-(ethyl-phenyl-amino)-propyl]-amide
(131) 4-{2-[(2-Chloro-phenylcarbamoyl)-methylsulfanyl]-4-oxo-4H-quinazolin-3-ylmethyl}-cyclohexanecarboxylic acid 2-chloro-benzylamide
(132) 4-(4-Benzyl-piperazine-1-carbonyl)-2-(4-fluoro-benzyl)-3-(4-methoxy-phenyl)-3,4-dihydro-2H-isoquinolin-1-one
(133) 1-Allyl-6-(3,4-dihydro-1H-isoquinoline-2-sulfonyl)-4-oxo-1,4-dihydro-quinoline-3-carboxylic acid benzylmethyl-amide
(134) N-(2-Chloro-benzyl)-4-[1-(2-chloro-4-fluoro-benzyl)-2,4-dioxo-1,4-dihydro-2H-quinazolin-3-yl]-butyramide
(135) 2-(3,3-Dimethyl-2-oxo-butylsulfanyl)-4-oxo-3-phenyl-3,4-dihydro-quinazoline-7-carboxylic acid 2-chlorobenzylamide
(136) 2-Isobutyl-1-oxo-3-thiophen-2-yl-1,2,3,4-tetrahydro-isoquinoline-4-carboxylic acid [3-(benzyl-isopropylamino)-propyl]-amide
(137) 2,4-Dioxo-1-[2-oxo-2-(4-phenyl-piperazin-1-yl)-ethyl]-3-p-tolyl-1,2,3,4-tetrahydro-quinazoline-7-carboxylic acid 2-chloro-benzylamide
(138) N-(1-Benzyl-piperidin-4-yl)-4-{1-[2-(4-fluoro-phenyl)-2-oxo-ethyl]-2,4-dioxo-1,4-dihydro-2H-quinazolin-3-ylmethyl}-benzamide
(139) 4-[1-(2-Chloro-6-fluoro-benzyl)-2,4-dioxo-1,4-dihydro-2H-quinazolin-3-ylmethyl]-cyclohexanecarboxylic acid phenethyl-amide
(140) 8-Oxo-5,8,13,13a-tetrahydro-6H-isoquino[3,2-a]isoquinoline-13-carboxylic acid [1-(3-methyl-benzyl)-piperidin-4-ylmethyl]-amide
(141) 2-(4-Fluoro-benzyl)-3-(4-methoxy-phenyl)-1-oxo-1,2,3,4-tetrahydro-isoquinoline-4-carboxylic acid (3-dipropylamino-propyl)-amide
(142) N,N'-Dibenzyl-2-(4-oxo-3-phenyl-3,4-dihydro-quinazolin-2-ylsulfanyl)-malonamide
(143) 6-(4-Isopropyl-phenylsulfamoyl)-4-oxo-1,4-dihydro-quinoline-3-carboxylic acid [2-(ethyl-phenyl-amino)-ethyl]-amide
(144) 2,3-Diethoxy-8-oxo-5,8,13,13a-tetrahydro-6H-isoquino[3,2-a]isoquinoline-13-carboxylic acid [3-(4-benzyl-piperidin-1-yl)-propyl]-amide
(145) 5-[1-(2-Chloro-benzyl)-2,4-dioxo-1,4-dihydro-2H-quinazolin-3-yl]-pentanoic acid 2-chloro-benzylamide
(146) 5-[1-(2-Chloro-benzyl)-2,4-dioxo-1,4-dihydro-2H-quinazolin-3-yl]-pentanoic acid [2-(4-chloro-phenyl)-ethyl]-amide
(147) 2-(3-Benzyl-4-oxo-6-piperidin-1-yl-3,4-dihydro-quinazolin-2-ylsulfanyl)-N-[2-(4-sulfamoyl-phenyl)-ethyl]-acetamide
(148) 4-[2-(7-Chloro-4-oxo-4H-pyrido[1,2-a]pyrimidin-2-ylmethylsulfanyl)-4-oxo-4H-quinazolin-3-ylmethyl]-cyclohexanecarboxylic acid 2-chloro-benzylamide
(149) 3-Benzyl-2-[2-(1-benzyl-1H-indol-3-yl)-vinyl]-3H-quinazolin-4-one
(150) 1-{3-[4-(4-Acetyl-phenyl)-piperazin-1-yl]-3-oxo-propyl}-4-phenethyl-4H-[1,2,4]triazolo[4,3-a]quinazolin-5-one
(151) N-(4-Methyl-benzyl)-2-[3-(3-{2-[(4-methyl-benzylcarbamoyl)-methylsulfanyl]-4-oxo-4H-quinazolin-3-yl}-propyl)-4-oxo-3,4-dihydro-quinazolin-2-ylsulfanyl]-acetamide
(152) 4-[4-Oxo-2-(2-oxo-2-phenyl-ethylsulfanyl)-4H-quinazolin-3-ylmethyl]-cyclohexanecarboxylic acid phenethyl-amide
(153) 4-Oxo-2-(2-oxo-2-phenyl-ethylsulfanyl)-3-phenyl-3,4-dihydro-quinazoline-7-carboxylic acid 3-chloro-benzylamide
(154) 3-Benzyl-4-oxo-2-(2-oxo-2-phenyl-ethylsulfanyl)-3,4-dihydro-quinazoline-7-carboxylic acid 3-chloro-benzylamide
(155) 2-(3-Chloro-benzylsulfanyl)-4-oxo-3-pentyl-3,4-dihydro-quinazoline-7-carboxylic acid benzylamide
(156) N-[2-(4-Chloro-phenyl)-ethyl]-4-[2,4-dioxo-1-(2,4,6-trimethyl-benzyl)-1,4-dihydro-2H-quinazolin-3-yl]-butyramide
(157) 3-(4-Methoxy-phenyl)-2,4-dioxo-1-(2,4,6-trimethyl-benzyl)-1,2,3,4-tetrahydro-quinazoline-7-carboxylic acid 4-methyl-benzylamide
(158) N-[2-(4-Chloro-phenyl)-ethyl]-3-[4-(4-fluoro-benzyl)-5-oxo-4,5-dihydro-[1,2,4]triazolo[4,3-a]quinazolin-1-yl]-propionamide
(159) 4-Oxo-2-(2-oxo-2-phenyl-ethylsulfanyl)-3-pentyl-3,4-dihydro-quinazoline-7-carboxylic acid 3-chloro-benzylamide (160) 3-{4-[1,3-Dioxo-2-(2-trifluoromethyl-phenyl)-2,3-dihydro-1H-isoindol-5-yloxy]-phenyl}-4-oxo-3,4-dihydro-quinazoline-2-carboxylic acid ethyl ester
(161) 2-(3-Benzyl-4-oxo-3,4-dihydro-thieno[3,2-d]pyrimidin-2-ylsulfanyl)-N-[2-(4-sulfamoyl-phenyl)-ethyl]-acetamide
(162) 4-{2-[2-(4-Fluoro-phenyl)-2-oxo-ethylsulfanyl]-4-oxo-4H-quinazolin-3-ylmethyl}-cyclohexanecarboxylic acid 2-chloro-benzylamide
(163) 4-Oxo-2-(2-oxo-2-phenyl-ethylsulfanyl)-3-phenethyl-3,4-dihydro-quinazoline-7-carboxylic acid (3,5-dimethyl-phenyl)-amide
(164) 2-[3-(2-Chloro-benzyl)-4-oxo-3,4-dihydro-benzo[4,5]thieno[3,2-d]pyrimidin-2-ylsulfanyl]-N-(4-methyl-benzyl)-acetamide
(165) 2-[2-(3,4-Dihydro-2H-quinolin-1-yl)-2-oxo-ethylsulfanyl]-3-phenethyl-3H-benzo[4,5]thieno[3,2-d]pyrimidin-4-one
(166) 6-{2-[2-(4-Chloro-phenyl)-2-oxo-ethylsulfanyl]-4-oxo-4H-thieno[3,2-d]pyrimidin-3-yl}-hexanoic acid 4-methyl-benzylamide
(167) 1,3-Diethyl-2-{3-ethyl-5-[2-(3-ethyl-3H-benzothiazol-2-ylidene)-ethylidene]-4-oxo-thiazolidin-2-ylidenemethyl}-6-trifluoromethanesulfonyl-3H-benzoimidazol-1-ium
(168) 4-(3-chlorobenzyl)-2-(1-(4-(2-methoxyphenyl)piperazin-1-yl)-1-oxopropan-2-yl)-2H-benzo[b][1,4]thiazin-3(4H)-one
(169) 1-Benzyl-7-diethylamino-3-(2,4-dimethyl-benzenesulfonyl)-6-fluoro-1H-quinolin-4-one
(170) 1-Benzyl-3-(2,4-dimethyl-benzenesulfonyl)-6-fluoro-7-pyrrolidin-1-yl-1H-quinolin-4-one
(181) 1-{2-Oxo-2-[4-(1-phenyl-ethyl)-piperazin-1-yl]-ethyl}-4-(tetrahydro-furan-3-ylmethyl)-4H-[1,2,4]triazolo[4,3-a]quinazolin-5-one
(182) 3-(1,4-Dicyclopropyl-1H-pyrrol-3-yl)-2-methyl-4-(4-o-tolyl-piperazine-1-carbonyl)-3,4-dihydro-2H-isoquinolin-1-one
(183) 4-[2-(2-Cyano-benzoylamino)-4-oxo-4H-quinazolin-3-ylmethyl]-piperazine-1-carboxylic acid amide
(184) 4-[4-(4-Chloro-phenyl)-piperazine-1-carbonyl]-2-methyl-3-(2,3,4,5-tetrahydro-1'H-[1,2']bipyrrolyl-4'-yl)-3,4-dihydro-2H-isoquinolin-1-one
(185) 4-{2-[(Cyclohex-3-enylcarbamoylmethyl)-amino]-4-oxo-4H-quinazolin-3-ylmethyl}-piperazine-1-carboxylic acid benzylamide
(186) 4-Fluoro-benzoic acid 7-oxo-6-{2-[4-(4-sulfamoyl-phenyl)-butyrylamino]-ethyl}-6,7-dihydro-isothiazolo[4,5-d]pyrimidin-5-yl ester
(187) 5-[5-(2-Fluoro-benzylsulfanyl)-7-oxo-7H-oxazolo[4,5-d]pyrimidin-6-yl]-pentanoic acid (2-pyridin-4-yl-ethyl)-amide
(188) 6-Benzenesulfonylamino-1-cyclopropyl-4-oxo-1,4-dihydro-quinoline-3-carboxylic acid benzyl-methyl-amide
(189) 8-Oxo-5,8,13,13a-tetrahydro-6H-isoquino[3,2-a]isoquinoline-13-carboxylic acid (4-phenyl-piperazin-1-yl)-amide
(190) N-(2-{1-[2-(6-Chloro-pyridin-3-yl)-acetyl]-6-fluoro-2,4-dioxo-1,4-dihydro-2H-quinazolin-3-yl}-ethyl)-2-phenyl-propionamide
(191) N-(5-Oxo-4-pyrimidin-4-ylmethyl-4,5-dihydro-[1,2,4]triazolo[4,3-a]quinazolin-1-ylmethyl)-3-(4-trifluoromethyl-phenyl)-propionamide
(192) N-(6-Fluoro-7-morpholin-4-yl-4-oxo-1-pyridin-4-ylmethyl-1,4-dihydro-quinolin-3-yl)-2,4-dimethyl-benzenesulfonamide
(193) N-(4-Methyl-piperazin-1-ylmethyl)-C-(4-oxo-3-pyridin-4-ylmethyl-3,4-dihydro-benzo[4,5]furo[3,2-d]pyrimidin-2-ylamino)-methanesulfonamide
(194) N-[3-Oxazol-5-yl-1-oxo-2-(tetrahydro-pyran-4-yl)-1,2,3,4-tetrahydro-isoquinolin-4-ylmethyl]-3-(4-phenyl-piperazin-1-yl)-propionamide In one aspect, the present invention provides a method for treating a condition, disorder, or disease, or stimulating contraceptive effect, in a patient in need thereof comprising administering to the patient a therapeutically effective amount of the compound having a structural formula (II), (III) or (IV) as defined in the pharmaceutical composition, or a salt, solvate, ester, and/or prodrug thereof, wherein the condition, disorder, or disease is implicated in the activation or hyperactivity of low voltage-gated calcium channels.

Preferably, the condition, disorder, or disease is selected from the group consisting of epilepsy, peripheral neuropathy, Parkinson's disease, essential tremor, insomnia, psychosis, schizophrenia, hypertension, angina, arteriosclerosis, nervous system injury, anxiety disorder, seizure, convulsion, Huntington's chorea, Alzheimer's disease, multiple sclerosis, autoimmune disease, tremor, retinopathy, neoplasm, inflammation, cranial neuropathy, myocardial infarction, stroke, pain, acute pain, chronic pain, neuropathic pain, inflammatory pain, arthritis, migraine, cluster headaches, trigeminal neuralgia, herpetic neuralgia, general neuralgias, neurodegenerative disorders, anxiety, depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck-pain, severe or intractable pain, nociceptive pain, breakthrough pain, postsurgical pain, cancer pain, cancer, hypertension, stroke, type 1 or type 2 diabetes, hyperaldosteronemia, preterm labor, urinary incontinence, and brain aging.

In one aspect, the present invention provides a method of modulating calcium ion channels comprising contacting the compound having a structural formula (II), (III) or (IV) as defined in the pharmaceutical composition, or a salt, solvate, ester, and/or prodrug thereof, with the calcium ion channels. In one embodiment, the modulation comprises selectively antagonizing at least one subunit of T-type calcium ion channels in a patient in need thereof.

In one aspect, the present invention provides a method of treating a condition, disorder, or disease, or stimulating contraceptive effect, in a patient in need thereof, comprising administering to the patient a therapeutically effective amount of a compound having structural formula (XII), or a salt, solvate, ester, and/or prodrug thereof, wherein the condition, disorder, or disease is implicated in the activation or hyperactivity of low voltage-gated calcium channels,

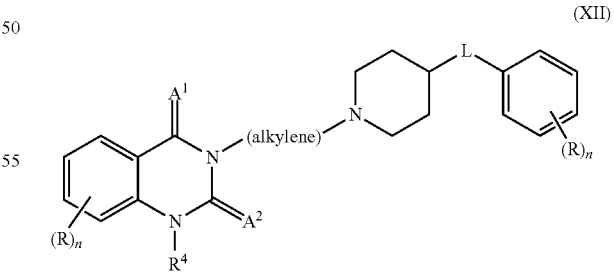

wherein
$A^1$ and $A^2$ are each independently O, S, N—R, or N—OR;
$R^4$ is hydrogen, alkyl, substituted alkyl, heteroalkyl, substituted heteroalkyl, hydroxyl, alkoxy, amino, or alkamino;
L is each independently —C(O)—, —C(=S)—, —C(=NR$^1$)—, —C(=N—OR$^1$)—, —S(O)—, —S(O)$_2$—, or —C(R$^2$R$^3$)—;

R is each independently halo, alkyl, substituted alkyl, heteroalkyl, substituted heteroalkyl, hydroxyl, alkoxy, amino, alkamino, cyano, or nitro;

n is an integer of 0, 1, 2, 3, or 4; and m is an integer of 0, 1, or 2.

Preferably, the condition, disorder, or disease is selected from the group consisting of epilepsy, peripheral neuropathy, Parkinson's disease, essential tremor, insomnia, psychosis, schizophrenia, hypertension, angina, arteriosclerosis, nervous system injury, anxiety disorder, seizure, convulsion, Huntington's chorea, Alzheimer's disease, multiple sclerosis, autoimmune disease, tremor, retinopathy, neoplasm, inflammation, cranial neuropathy, myocardial infarction, stroke, pain, acute pain, chronic pain, neuropathic pain, inflammatory pain, arthritis, migraine, cluster headaches, trigeminal neuralgia, herpetic neuralgia, general neuralgias, neurodegenerative disorders, anxiety, depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck-pain, severe or intractable pain, nociceptive pain, breakthrough pain, postsurgical pain, cancer pain, cancer, hypertension, stroke, type 1 or type 2 diabetes, hyperaldosteronemia, preterm labor, urinary incontinence, and brain aging.

In one embodiment, the compound having a structural formula (XII) is selected from the group consisting of

401

(Ketanserin)

402

403

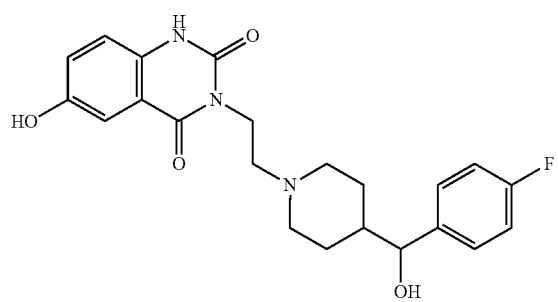

405

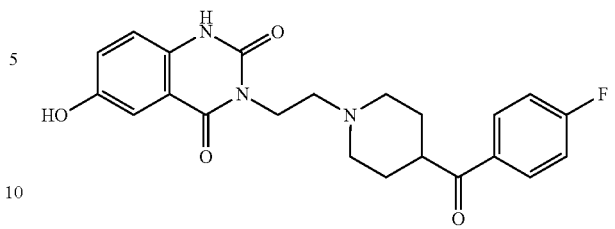

407

409

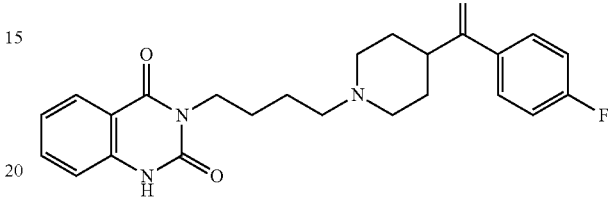

410

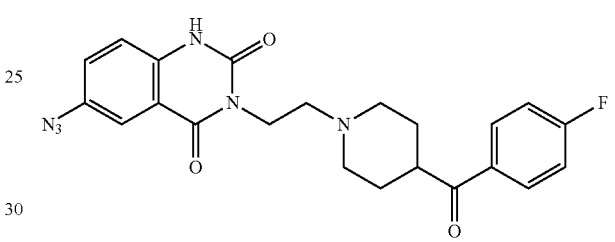

412

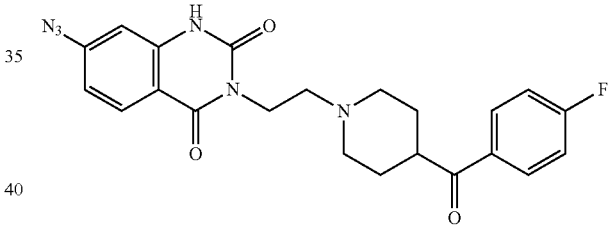

413

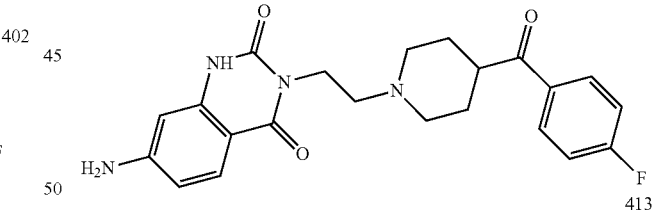

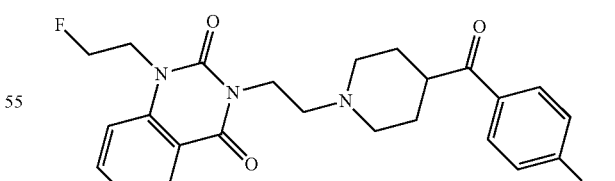

or the salt, solvate, ester, and/or prodrug thereof.

The above-listed compounds may also be represented by their chemical names as follows:

(401)  3-{2-[4-(4-Fluoro-benzoyl)-piperidin-1-yl]-ethyl}-1H-quinazoline-2,4-dione (Ketanserin)

(402)  3-(2-{4-[(4-fluorophenyl)(hydroxy)methyl]piperidin-1-yl}ethyl)quinazoline-2,4(1H,3H)-dione (403) 3-(2-{4-[(4-fluorophenyl)(hydroxy)methyl]piperidin-1-yl}ethyl)-6-hydroxyquinazoline-2,4(1H,3H)-dione (404) 3-(2-{4-[(4-fluorophenyl)carbonyl]piperidin-1-yl}ethyl)-6-hydroxyquinazoline-2,4(1H,3H)-dione (405) 3-(4-{4-[(4-fluorophenyl)carbonyl]piperidin-1-yl}butyl)quinazoline-2,4(1H,3H)-dione (406) 6-azido-3-(2-{4-[(4-fluorophenyl)carbonyl]piperidin-1-yl}ethyl)quinazoline-2,4(1H,3H)-dione (407) 7-azido-3-(2-{4-[(4-fluorophenyl)carbonyl]piperidin-1-yl}ethyl)quinazoline-2,4(1H,3H)-dione (408) 7-amino-3-(2-{4-[(4-fluorophenyl)carbonyl]piperidin-1-yl}ethyl)quinazoline-2,4(1H,3H)-dione (409) 1-(2-fluoroethyl)-3-(2-{4-[(4-fluorophenyl)carbonyl]piperidin-1-yl}ethyl)quinazoline-2,4(1H,3H)-dione In one aspect, the present invention provides a method of modulating calcium ion channels comprising contacting the compound having a structural formula (XII) as defined above, or a salt, solvent, ester, and/or prodrug thereof, with the calcium ion channels. In one embodiment, the modulation comprises selectively antagonizing at least one subunit of T-type calcium ion channels in a patient in need thereof.

In one aspect, the present invention provides a method of treating a condition, disorder, or disease, or stimulating contraceptive effect, in a patient in need thereof, comprising administering to the patient a therapeutically effective amount of a compound selected from the group consisting of cyclopentyl[3-(2-methoxy-4-{[(2-methylphenyl)sulfonyl]carbamoyl}benzyl)-1-methyl-1H-indol-5-yl]carbamate (Zafirlukast); (5'α)-2-bromo-12'-hydroxy-5'-(2-methylpropyl)-3',6',18-trioxo-2'-(propan-2-yl)ergotaman (Bromocriptine); and 4,4'-(propane-2,2-diyldisulfanediyl)bis(2,6-di-tert-butylphenol) (Probucol), or a salt, solvate, ester, and/or prodrug thereof, wherein the condition, disorder, or disease is implicated in the activation or hyperactivity of low voltage-gated calcium channels.

The chemical structures of cyclopentyl[3-(2-methoxy-4-{[(2-methylphenyl)sulfonyl]carbamoyl}benzyl)-1-methyl-1H-indol-5-yl]carbamate (Zafirlukast); (5'α)-2-bromo-12'-hydroxy-5'-(2-methylpropyl)-3',6',18-trioxo-2'-(propan-2-yl)ergotaman (Bromocriptine); and 4,4'-(propane-2,2-diyldisulfanediyl)bis(2,6-di-tert-butylphenol) (Probucol) are shown below:

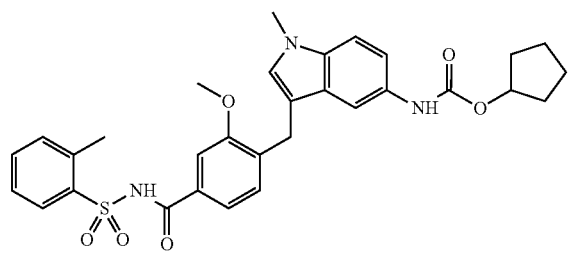
(Zafirlukast)

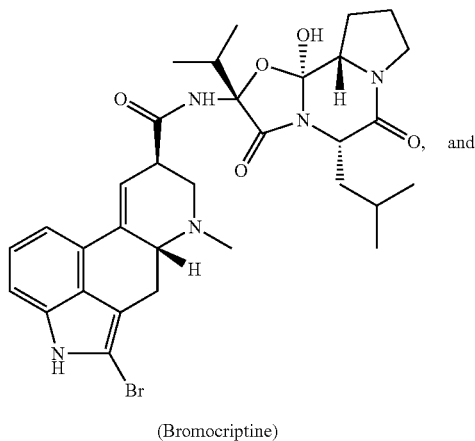
(Bromocriptine)

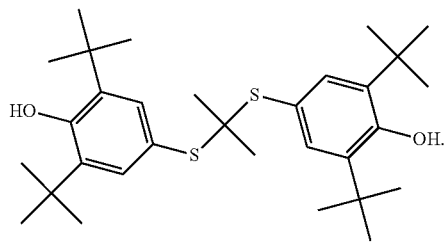
(Probucol)

Preferably, the condition, disorder, or disease is selected from the group consisting of epilepsy, peripheral neuropathy, Parkinson's disease, essential tremor, insomnia, psychosis, schizophrenia, hypertension, angina, arteriosclerosis, nervous system injury, anxiety disorder, seizure, convulsion, Huntington's chorea, Alzheimer's disease, multiple sclerosis, autoimmune disease, tremor, retinopathy, neoplasm, inflammation, cranial neuropathy, myocardial infarction, stroke, pain, acute pain, chronic pain, neuropathic pain, inflammatory pain, arthritis, migraine, cluster headaches, trigeminal neuralgia, herpetic neuralgia, general neuralgias, neurodegenerative disorders, anxiety, depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck-pain, severe or intractable pain, nociceptive pain, breakthrough pain, postsurgical pain, cancer pain, cancer, hypertension, stroke, type 1 or type 2 diabetes, hyperaldosteronemia, preterm labor, urinary incontinence, and brain aging.

In one aspect, the present invention provides a method of modulating calcium ion channels comprising contacting a compound selected from the group consisting of cyclopentyl[3-(2-methoxy-4-{[(2-methylphenyl)sulfonyl]carbamoyl}benzyl)-1-methyl-1H-indol-5-yl]carbamate (Zafirlukast); (5'α)-2-bromo-12'-hydroxy-5'-(2-methylpropyl)-3',6',18-trioxo-2'-(propan-2-yl)ergotaman (Bromocriptine); and 4,4'-(propane-2,2-diyldisulfanediyl)bis(2,6-di-tert-butylphenol) (Probucol), or a salt, solvent, ester, and/or prodrug thereof, with the calcium ion channels. In one embodiment, the modulation comprises selectively antagonizing at least one subunit of T-type calcium ion channels in a patient in need thereof.

Specific embodiments of the present invention include, but are not limited to a compound which is selected from the group consisting of the subject compounds of the above examples, including Table 1 or Table 2 herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Exemplifying the invention is the use of the compounds disclosed in the Examples and herein. Specific compounds within the present invention include a compound which selected from the group consisting of the compounds disclosed in the following examples, which include Table 1 or Table 2 and pharmaceutically acceptable salts, solvates, ester, and/or prodrugs thereof and individual diastereomers thereof.

The subject compounds are useful in a method of antagonizing calcium, particularly T-type calcium channel activity in a patient such as a mammal in need of such inhibition comprising the administration of an effective amount of the compound. The present invention is directed to the use of the compounds disclosed herein as antagonists of calcium, particularly T-type calcium channels activity. In addition to primates, especially humans, a variety of other mammals can be treated according to the method of the present invention.

The present invention is further directed to a method for the manufacture of a medicament for antagonizing calcium, particularly T-type calcium channels activity or treating the disorders and diseases noted herein in humans and animals comprising combining a compound of the present invention with a pharmaceutical carrier or diluent.

The subject treated in the present methods is generally a mammal, preferably a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein herein, but does not necessarily indicate a total elimination of all disorder symptoms, as well as the prophylactic therapy of the mentioned conditions, particularly in a patient who is predisposed to such disease or disorder. The terms "administration or" and or "administering" a compound should be understood to mean providing a compound of the invention or a prodrug or a softdrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as calcium, particularly T-type calcium channel antagonists may be readily determined without undue experimentation by methodology well known in the art, including in (I) freshly dissociated neurons from dorsal root ganglia (DRG) or thalamus of adult rats or mouse to study pharmacological properties of low-voltage-activated T-type $Ca^{2+}$ current after the inhibition of other ion channels in native DRG or thalamus cells by utilizing the cell patch-clamp method [described, for examples, by S. M. Todorovic and C. J. Lingle, The Journal of Neurophysiology, Vol. 79 No. 1 January 1998, pp. 240-252, and Joksovic, et al, *J Physiol* 574.2 pp 415-430 (2006)]; (II) the "FLIPR $Ca^{2+}$ Flux Assay" and (III) the "T-type Calcium ($Ca^{2+}$) Antagonists Voltage-Clamp Assay" [described by Xia, et al., Assay and Drug Development Tech., 1(5), 637-645 (2003)]. In a typical experiment ion channel function from HEK 293 cells expressing the calcium or T-type channel alpha-1G, H, or I (Cav3.1, Cav3.2, Cav3.3) is recorded to determine the activity of compounds in blocking the calcium current mediated by the calcium or T-type channel alpha-1G, H, or I (Cav3.1, Cav3.2, Cav3.3). In this T-type calcium (C2+) antagonist voltage-clamp assay calcium currents are elicited from the resting state of the human alpha-1G, H, or I (Cav3.1, Cav3.2, Cav3.3) calcium channel as follows. Sequence information for T-type (Low-voltage activated) calcium channels are fully disclosed in e.g., U.S. Pat. No. 5,618,720, U.S. Pat. No. 5,686,241, U.S. Pat. No. 5,710,250, U.S. Pat. No. 5,726,035, U.S. Pat. No. 5,792,846, U.S. Pat. No. 5,846,757, U.S. Pat.

No. 5,851,824, U.S. Pat. No. 5,874,236, U.S. Pat. No. 5,876,958, U.S. Pat. No. 6,013,474, U.S. Pat. No. 6,057,114, U.S. Pat. No. 6,096,514, WO99/28342, and J. Neuroscience, 19(6):1912-1921 (1999). Cells expressing the T-type channels were grown in growth media which comprised: DMEM, 10% Tetsystem approved FBS (Clontech Laboratories Inc.), 100 microgram/ml Penicillin/Streptomycin, 2 mM L-Glutamine, 150 microgram/ml Zeocin, 5 microgram/ml Blasticidin. T-channel expression was induced by exposing the cells to 2 mM Tetracycline for 24 hrs. Glass pipettes are pulled to a tip diameter of 1-2 micrometer on a pipette puller. The pipettes are filled with the intracellular solution and a chloridized silver wire is inserted along its length, which is then connected to the headstage of the voltage-clamp amplifier. Trypsinization buffer was 0.05% Trypsin, 0.53 mM EDTA. The extracellular recording solution consists of (mM): 130 mM NaCl, 4 mM KCl, 1 mM MgCl2, 2 mM CaCl2, 20 roM HEPES, 30 Glucose, pH 7.4. The internal solution consists of (mM): 125 CsCl, 10 TEA-Cl, 10 HEPES, 8 NaCl, 0.06 CaCl2, 0.6 EGTA, 4 ATP-Mg, 0.3 GTP; 135 roM CsMeSO3, 1 MgCl2, 10 CsCl, 5 EGTA, 10 HEPES, pH 7.4; or 135 mM CsCl, 2 MgCl2, 3 MgATP, 2 Na2ATP, 1 Na2GTP, 5 EGTA, 10 HEPES, pH 7.4. Upon insertion of the pipette tip into the bath, the series resistance is noted (acceptable range is between 1-4 megaohm). The junction potential between the pipette and bath solutions is zeroed on the amplifier. The cell is then patched, the patch broken, and, after compensation for series resistance (>=80%), the voltage protocol is applied while recording the whole cell Ca2+ current response. Voltage protocols: (1) –80 mV holding potential every 20 seconds pulse to –20 mV for 70 msec duration; the effectiveness of the drug in inhibiting the current mediated by the channel is measured directly from measuring the reduction in peak current amplitude initiated by the voltage shift from –80 mV to –20 mV; (2). –100 mV holding potential every 15 seconds pulse to –20 mV for 70 msec duration; the effectiveness of the drug in inhibiting the current mediated by the channel is measured directly from measuring the reduction in peak current amplitude initiated by the shift in potential from –100 mV to –20 mV. The difference in block at the two holding potentials was used to determine the effect of drug at differing levels of inactivation induced by the level of resting state potential of the cells. After obtaining control baseline calcium currents, extracellular solutions containing increasing concentrations of a test compound are washed on. Once steady state inhibition at a given compound concentration is reached, a higher concentration of compound is applied. % inhibition of the peak inward control $Ca^{2+}$ current during the depolarizing step to –20 mV is plotted as a function of compound concentration.

The intrinsic T-type calcium channel antagonist activity of a compound which may be used in the present invention may be determined by these assays. In particular, the compounds of the aforementioned examples, including Table 1 and Table 2 had activity in antagonizing the T-type calcium channel in the aforementioned assays, generally with an IC50 of less than about 25 µM. Preferred compounds within the present invention had activity in antagonizing the T-type calcium channel in the aforementioned assays with an IC50 of less than about 1 µM. Such a result is indicative of the intrinsic activity of the compounds in use as antagonists of T-type calcium channel activity.

T-type calcium channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with calcium channels, including one or more of the following conditions or diseases: movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, seizure disorders, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); heart disease, abnomal heart rhythms and arrythmias, myocardial infarction, congestive heart failure, coronary heart disease, sudden death, stroke, sexual and reproductive dysfunction, such as impaired fertility, infertility, diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing trained performance; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent waking during sleep; decreasing nocturnal arousals; decreasing the time spent awake following the initial onset of sleep; increasing the total amount of sleep; reducing, the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing the amount of Delta sleep early in the sleep cycle, increasing REM sleep late in the sleep cycle; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, obstructive sleep apnea, wakefulness, nocturnal myoclonus, REM sleep interruptions, jet-lag, shift workers' sleep disturbances, dyssonmias, night terror, insomnias associated with depression, emotional/mood disorders, Alzheimer's disease or cognitive impairment, as well as sleep walking and enmesis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which IS associated with respiratory disturbances during sleep; conditions which result from a diminished quality of sleep; mood disorders, such as depression or more particularly depressive disorders, for example, single episodic or recurrent major depressive disorders and dysthymic disorders, or bipolar disorders, for example, bipolar I disorder, bipolar n disorder and cyclothymic disorder, mood disorders due to a general medical condition, and substance-induced mood disorders; anxiety disorders including acute stress disorder, agomphobia, genemlized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); attention deficit/hyperactivity disorder (ADHD); conduct disorder; migraine (including migraine headache); urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in preferred embodiments the present invention provides methods for: treating, controlling, ameliorating or reducing the risk of epilepsy, including absence epilepsy; treating or controlling Parkinson's disease; treating essential tremor; treating or controlling pain, including neuropathic pain; enhancing the quality of sleep; augmenting sleep maintenance; increasing REM sleep; increasing slow wave sleep; decreasing fragmentation of sleep patterns; treating insomnia; enhancing cognition; increasing memory retention; treating or controlling depression; treating or controlling psychosis; or treating, controlling, ameliorating or reducing the risk of schizophrenia, in a mammalian patient in need thereof which comprises administering to the patient a therapeutically effective amount of the compound of the present invention.

The subject compounds are further useful in a method for the prevention, treatment, control, amelioration, or reduction of risk of the diseases, disorders and conditions noted herein.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 50 mg/kg of body weight daily are administered to the patient, e.g., humans and elderly humans, to obtain effective antagonism of calcium, particularly T-type calcium channel. The dosage range will generally be about 0.5 mg to 1.0 g per patient per day which may be administered in single or multiple doses. Preferably, the dosage range will be about 0.5 mg to 500 mg per patient per day; more preferably about 0.5 mg to 200 mg per patient per day; and even more preferably about 5 mg to 50 mg per patient per day. Pharmaceutical compositions of the present invention may be provided in a solid dosage formulation preferably comprising about 0.5 mg to 500 mg active ingredient, more preferably comprising about 1 mg to 250 mg active ingredient. The pharmaceutical composition is preferably provided in a solid dosage formulation comprising about 1 mg, 5 mg, 10 mg, 25 mg, 50 mg, 100 mg, 200 mg or 250 mg active ingredient. For oral administration, the compositions are preferably provided in the form of tablets containing 1.0 to 1000 milligrams of the active ingredient, particularly 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be employed in combination with an anti-seizure agent such as carbamazepine, clonazepam, divalproex, ethosuximide, felbamate, fosphenytoin, gabapentin, lamotrigine, levetiracetam, lorazepam, midazolam, oxcarbazepine, phenobarbital, phenytoin, primidone, tiagabine, topiramate, valproate, vigabatrin or zonisamide. In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene, trifluoperazine or valproic acid.

In another embodiment, the compounds of the present invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexol) hydrochloride, COMT inhibitors such as entacapone, MOA-B inhibitors, antioxidants, A2a adenosine receptor antagonists, cholinergic agonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the compounds of the present invention may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazinc, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the compounds of the present invention may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antimflammatory agent, or a cytokine-suppressing anti inflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, car beta pentane, or dextramethorphan; a diuretic; and a sedating or non-sedating antihistamine. In another embodiment, the subject compound may be employed in combination with an L-type calcium channel antagonist, such as amlodipine.

In another embodiment, the compounds of the present invention may be administered in combination with compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, other T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, buprion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazeparn, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the compounds of the present invention may be employed in combination with an antidepressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, a-adrenoreceptor antagonists, neurokinin-1 receptor antagonists, atypical anti-depressants, benzodiazepines, 5-HT-1A agonists or antagonists, especially 5-HT-1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and seriraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the compounds of the present invention may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H3 antagonists; AMP A agonists; PDE4 inhibitors; $GABA_A$ inverse agonists; or neuronal nicotinic agonists.

The compounds of the present invention may be administered by oral, parenteral (e.g., intramuscular, intraperitoneal, intravenous, ICY, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; BuLi: butyllithium; Piv: pivaloyl; Ac: acetyl; THF: tetrahydrofuran; DMSO: dimethylsulfoxide; EDC: N-(3-Dimethylaminopropyl)-N'-ethylcarbodiimide; Boc: tert-butyloxy carbonyl; Et3N: triethylamine; DCM: dichloromethane; DCE: dichloroethane; DME: dimethoxyethane; DBA: diethylamine; DAST: diethylaminosulfur trifluoride; EtMgBr: ethylamgnesium bromide; BSA: bovine serum albumin; TFA: trifluoracetic acid; DMF: N,N-dimethylformamide; $SOCl_2$: thionyl chloride; CDI: carbonyl diirnidazole; rt: room temperature; HPLC: high performance liquid chromatography. The compounds of the present invention can be prepared in a variety of fashions.

The compounds of the invention comprise Formula I and II, as described above can be obtained from commercial sources, such as Aldrich Chemical Co. (Milwaukee, Wis.), Sigma Chemical Co. (St. Louis, Mo.), Maybridge (Cornwall, England), Asinex (Winston-Salem, N.C.), ChemBridge (San Diego, Calif.), ChemDiv (San Diego, Calif.), SPECS (Delft, The Netherlands), Timtec (Newark, Del.) or the compounds can be synthesized. The compounds of the present invention, and other related compounds having different subtituents identified by any of the methods described above can be synthesized using techniques and materials known to those of skill in the art, such as described, for example, in March, ADVANCED ORGANIC CHEMISTRY 4.sup.th Ed., (Wiley 1992); Carey and Sundberg, ADVANCED ORGANIC CHEMISTY 3.sup.rd Ed., Vols. A and B (Plenum 1992), and Green and Wuts, PROTECTIVE GROUPS IN ORGANIC SYNTHESIS 2.sup.nd Ed. (Wiley 1991). Starting materials useful for preparing compounds of the invention and intermediates thereof are commercially available or can be prepared by well-known synthetic methods (see, e.g., Harrison et al., "Compendium of Synthetic Organic Methods", Vols. 1-8 (John Wiley and Sons, 1971-1996); "Beilstein Handbook of Organic Chemistry." Beilstein Institute of Organic Chemistry, Frankfurt, Germany; Feiser et al., "Reagents for Organic Synthesis," Volumes 1-21, Wiley Interscience; Trost et al., "Comprehensive Organic Synthesis," Pergamon Press, 1991; "Theilheimer's Synthetic Methods of Organic Chemistry," Volumes 1-45, Karger. 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995). Other methods for synthesis of the compounds described herein and/or starting materials are either described in the art or will be readily apparent to the skilled artisan. Alternatives to the reagents and/or protecting groups may be found in the references provided above and in other compendiums well known to the skilled artisan. Guidance for selecting suitable protecting groups can be found, for example, in Greene & Wuts, "Protective Groups in Organic Synthesis," Wiley Interscience, 1999. Accordingly, the synthetic methods and strategy presented herein are illustrative rather than comprehensive.

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1H$ and $^{13}C$ NMR), infrared and ultraviolet spectroscopy (IR and UV), X-ray crystallography, elemental analysis (EA), HPLC and mass spectroscopy (MS) can be used as well. Methods of protection and deprotection, purification and identification and quantification are well known in the chemical arts.

Compounds represented by Formula I, for example, can be generally synthesized according to Scheme 1, of the intramolecular version of the Diels-Alder reaction of substituted furans (modified from Kharitonov, et al, Russian Journal of Organic Chemistry. 200, 41(8):1145-1157; and Padwa, et al, J. Org. Chem., 2006, 71:3210-3220).

Scheme 1

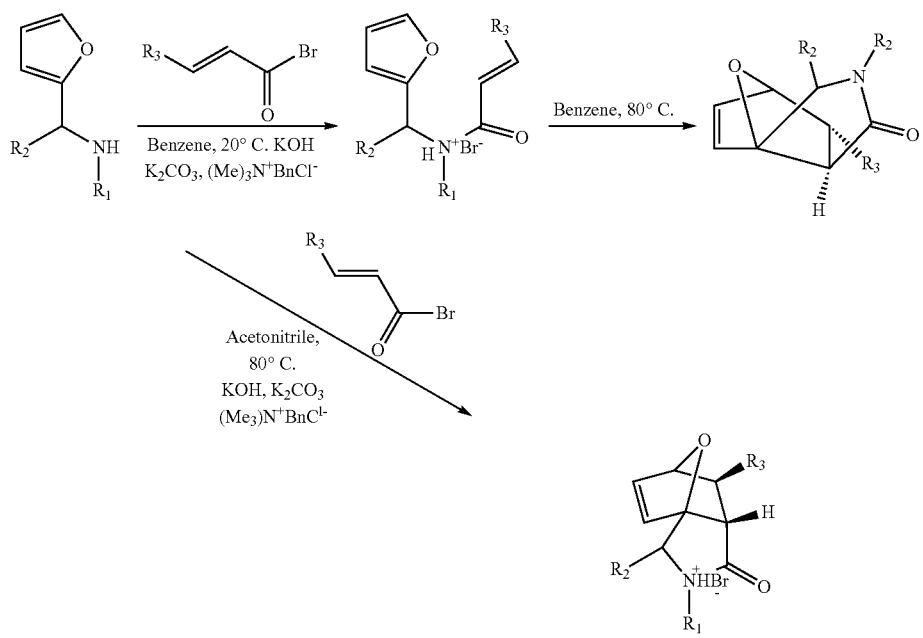

Compounds represented by Formula II, for example, can be generally synthesized according to Scheme 2.

Scheme 2

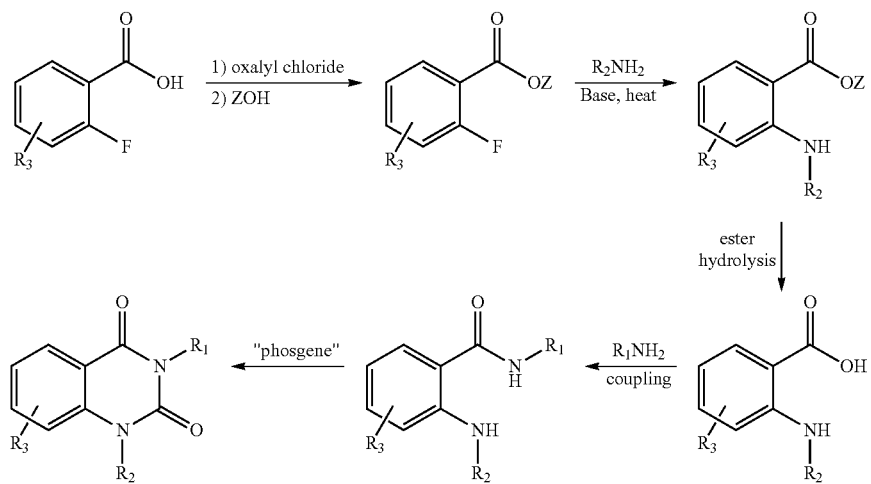

Figure 2:
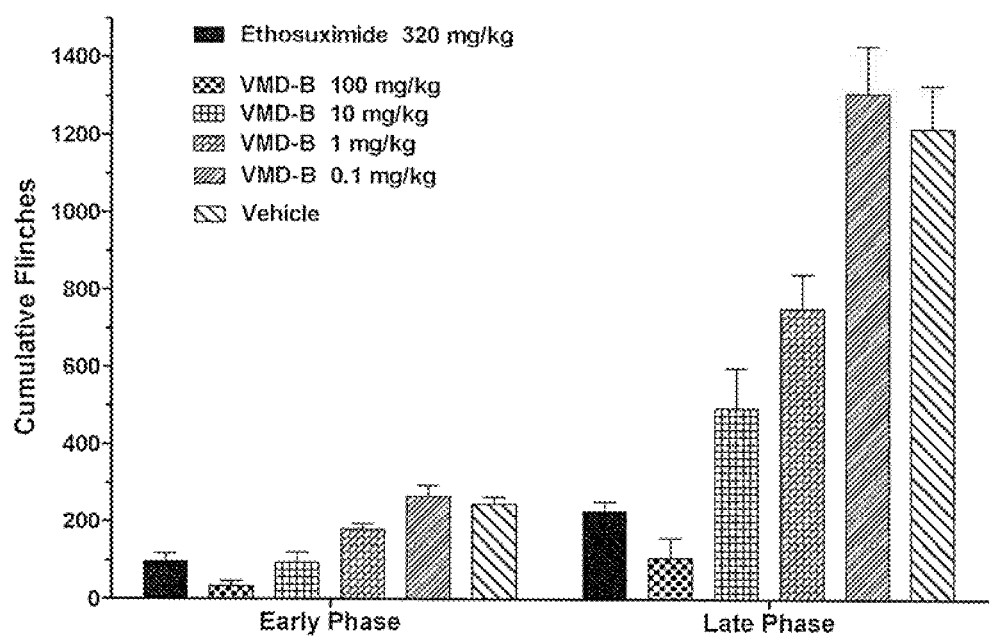
FIG. 2 is a graph showing reduction of Formalin induced pain in rat animal models of hyperalgesia by the compound (401): VMD-B.

Examples of reduction of Formalin induced pain in rat animal models of hyperalgesia by the following two compounds: compound (52), 3-(1-Methyl-3-phenyl-propyl)-4-oxo-10-oxa-3-aza-tricyclo[5.2.1.0$^{1,5}$]dec-8-ene-2,6-di carboxylic acid 2-[(3,5-dichloro-phenyl)-amide]6-[(2,3-dimethyl-cyclohexyl)-amide] (VMD-A), and compound (401), 3-{2-[4-(4-Fluoro-benzoyl)-piperidin-1-yl]-ethyl}-1H-quinazoline-2,4-dione (VMD-B) are given in FIGS. 1 and 2.

Rat Formalin Paw Test (in Vivo Assay): Compounds were assessed for their ability to inhibit the behavioral response evoked by an injection of formalin (50 μl of 5% formalin). A metal band was affixed to the left hind paw of male Holtzman rats (225-250 g, Harlan Industries, Indianapolis Ind.) and each rat was conditioned to the band for 60 min within a plastic cylinder (15 cm diameter). Rats were dosed with either vehicle, positive control compound or a test compound either before (local) or after (systemic) formalin challenge. For local administration, compounds were prepared in either a 10:7.5 vehicle of saline (in mL) and (D)- or (L)-Tartaric acid (in mg), or a 1:1:6 vehicle of DMA (N,N-Dimethylacetamide), Tween 80 and saline, and injected intraperitoneally into the dorsal surface of the right hind paw of the rat 60 min prior to formalin. The number of flinches was counted continuously for 60 min using an automated nociception analyzer (UCSD Anesthesiology Research, San Diego, Calif.). Statistical significance was determined by comparing the total flinches detected in the early (0-10 min, Phase I) and late (11-60 min) phase with an unpaired t-test. Here the drug Ethosiximide, a known weak T-type calcium ion channels antagonist, was used as a positive control compound (Gogas. K. R., et al. "Effects of the T-type calcium channel blocker, Elhosuximide in rodent models of acute and chronic pain", Abstract. IASP 10th World Congress on Pain. San Diego. Calif. 2002).

The content of the articles, publications, and patents cited hereinabove are all incorporated by reference in their entirety for all purposes to the same extent that each and every of them is herein incorporated by reference individually.

While the present invention has been particularly shown and described with respect to preferred embodiments thereof, it will be understood by those skilled in the art that the foregoing and other changes in forms and details may be made without departing from the spirit and scope of the invention. It is therefore intended that the present invention not be limited to the exact forms and details described and illustrated but fall within the scope of the appended claims.

We claim:
1. A compound having a structural Formula (I), or a salt, solvate, ester, and/or prodrug thereof:

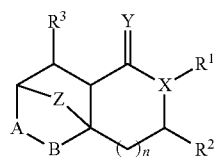

(I)

wherein:
A-B is —CHR$^4$CHR$^5$— or —CR$^4$=CR$^5$—;
X is —N—;
Y is O;
Z is —O—;
n is 0;
R$^1$ is substituted alkyl, arylalkyl, substituted arylalkyl, heteroalkyl or substituted heteroalkyl;
R$^2$ is —CONR$^{15}$R$^{16}$;
R$^3$ is —CONR$^{17}$R$^{18}$;
R$^4$ and R$^5$ are each independently hydrogen, alkyl, substituted alkyl, aryl, substituted aryl, arylalkyl or substituted arylalkyl;
R$^{15}$ is hydrogen, alkyl, or substituted alkyl;
R$^{16}$ is alkyl, substituted alkyl, aryl, substituted aryl, arylalkyl, substituted arylalkyl, heteroaryl, substituted heteroaryl, heteroarylalkyl, substituted heteroarylalkyl, heteroalkyl or substituted heteroalkyl;
R$^{17}$ is hydrogen, alkyl, or substituted alkyl;
R$^{18}$ is aryl, substituted aryl, arylalkyl, substituted arylalkyl, heteroaryl, substituted heteroaryl, heteroarylalkyl, substituted heteroarylalkyl, heteroalkyl, or substituted heteroalkyl; and
with the following proviso: Formula (I) does not include the compound selected from the group consisting of
(1) [6-(2-Methoxy-benzylcarbamoyl)-4-oxo-10-oxa-3-aza-tricyclo[5.2.1.0$^{1,5}$]dec-8-en-3-yl]-acetic acid ethyl ester
(2) 3-(4-Methyl-benzyl)-4-oxo-10-oxa-3-aza-tricyclo [5.2.1.0$^{1,5}$]dec-8-ene-6-carboxylic acid 2-chloro-benzylamide
(3) 3-[2-(3,4-Dimethoxy-phenyl)-ethyl]-4-oxo-10-oxa-3-aza-tricyclo[5.2.1.0$^{1,5}$]dec-8-ene-6-carboxylic acid cyclopentylamide
(4) 4-Oxo-3-thiophen-2-ylmethyl-10-oxa-3-aza-tricyclo [5.2.1.0$^{1,5}$]dec-8-ene-6-carboxylic acid 2,4,6-trifluorobenzylamide
(5) 3-(2-Chloro-benzyl)-4-oxo-10-oxa-3-aza-tricyclo [5.2.1.0$^{1,5}$]dec-8-ene-6-carboxylic acid 2-chloro-benzylamide
(6) 1-(2-{[3-(2-Chloro-benzyl)-4-oxo-10-oxa-3-aza-tricyclo[5.2.1.0$^{1,5}$]dec-8-ene-6-carbonyl]-amino}-ethyl)-2, 6-dimethyl-piperidinium
(7) Diisobutyl-{3-[(4-oxo-3-thiophen-2-ylmethyl-10-oxa-3-aza-tricyclo[5.2.1.0$^{1,5}$]dec-8-ene-6-carbonyl)-amino]-propyl}-ammonium
(8) 3-[2-(3,4-Dimethoxy-phenyl)-ethyl]-4-oxo-10-oxa-3-aza-tricyclo[5.2.1.0$^{1,5}$]dec-8-ene-6-carboxylic acid phenethyl-amide
(9) 3-(2-Chloro-benzyl)-4-oxo-10-oxa-3-aza-tricyclo [5.2.1.0$^{1,5}$]dec-8-ene-6-carboxylic acid [2-(ethyl-phenyl-amino)-ethyl]-amide
(10) 3-Allyl-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]
(11) 3-[2-(3,4-Dimethoxy-phenyl)-ethyl]-4-oxo-10-oxa-3-aza-tricyclo[5.2.1.0$^{1,5}$]dec-8-ene-6-carboxylic acid 2-chloro-benzylamide
(12) 3-[2-(3,4-Dimethoxy-phenyl)-ethyl]-4-oxo-10-oxa-3-aza-tricyclo[5.2.1.0$^{1,5}$]dec-8-ene-6-carboxylic acid [2-(4-chloro-phenyl)-ethyl]-amide
(13) 3-tert-Butyl-4-oxo-10-oxa-3-aza-tricyclo[5.2.1.0$^{1,5}$] dec-8-ene-2,6-dicarboxylic acid 2-cyclohexyamide 6-[(3-methylsulfanyl-phenyl)-amide]
(14) 4-Oxo-3-propyl-10-oxa-3-aza-tricyclo[5.2.1.0$^{1,5}$] dec-8-ene-2,6-dicarboxylic acid 6-cyclohexylamide 2-[(3,5-dichloro-phenyl)-amide]
(15) 3-Benzyl-4-oxo-10-oxa-3-aza-tricyclo[5.2.1.0$^{1,5}$] dec-8-ene-2,6-dicarboxylic acid 6-cyclohexylamide 2-[(3,5-dimethyl-phenyl)-amide]
(16) 4-Oxo-3-(tetrahydro-furan-2-ylmethyl)-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]
(17) 3-(4-Methyl-benzyl)-4-oxo-10-oxa-3-aza-tricyclo [5.2.1.0$^{1,5}$]dec-8-ene-2,6-dicarboxylic acid 6-cyclohexylamide 2-[(3,5-dimethyl-phenyl)-amide]
(18) 3-Benzyl-4-oxo-10-oxa-3-aza-tricyclo[5.2.1.0$^{1,5}$] dec-8-ene-2,6-dicarboxylic acid 6-[(3-methoxy-phenyl)-amide]2-[(2-methyl-cyclohexyl)-amide]
(19) 4-Oxo-3-pyridin-3-ylmethyl-10-oxa-3-aza-tricyclo [5.2.1.0$^{1,5}$]dec-8-ene-2,6-dicarboxylic acid 6-[(3-methoxy-phenyl)-amide]2-[(2-methyl-cyclohexyl)-amide]
(20) 3-(4-Fluoro-benzyl)-4-oxo-10-oxa-3-aza-tricyclo [5.2.1.0$^{1,5}$]dec-8-ene-2,6-dicarboxylic acid 6-cyclohexylamide 2-[(3,5-dimethyl-phenyl)-amide]
(21) 3-(2-Fluoro-benzyl)-4-oxo-10-oxa-3-aza-tricyclo [5.2.1.0$^{1,5}$]dec-8-ene-2,6-dicarboxylic acid 6-cyclohexylamide 2-[(3,5-dimethyl-phenyl)-amide]
(22) 3-(2,3-Dimethyl-cyclohexyl)-4-oxo-10-oxa-3-aza-tricyclo[5.2.1.0$^{1,5}$]dec-8-ene-2,6-dicarboxylic acid 2-[(2-methyl-cyclohexyl)-amide]6-m-tolylamide
(23) 4-Oxo-3-thiophen-2-ylmethyl-10-oxa-3-aza-tricyclo [5.2.1.0$^{1,5}$]dec-8-ene-2,6-dicarboxylic acid 6-[(3-methoxy-phenyl)-amide]2-[(2-methyl-cyclohexyl)-amide]
(24) 4-Oxo-3-(tetrahydro-furan-2-ylmethyl)-10-oxa-3-aza-tricyclo[5.2.1.0$^{1,5}$]dec-8-ene-2,6-dicarboxylic acid 6-[(2,3-dimethyl-cyclohexyl)-amide]2-[(3,5-dimethyl-phenyl)-amide]

(25) 2-[2-Cyclohexylcarbamoyl-6-(3-methoxy-phenylcarbamoyl)-4-oxo-10-oxa-3-aza-tricyclo[5.2.1.0$^{1,5}$]dec-8-en-3-ylmethyl]-1-ethyl-pyrrolidinium

(26) 4-Oxo-3-pyridin-3-ylmethyl-10-oxa-3-aza-tricyclo[5.2.1.0$^{1,5}$]dec-8-ene-2,6-dicarboxylic acid 6-[(2,3-dimethyl-cyclohexyl)-amide]2-[(3,5-dimethyl-phenyl)-amide]

(27) 3-(4-Methyl-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(28) 3-(4-Fluoro-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(29) 3-(2-Fluoro-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(30) 3-(4-Chloro-benzyl)-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]

(31) 4-Oxo-3-(tetrahydro-furan-2-ylmethyl)-10-oxa-3-aza-tricyclo[5.2.1.0$^{1,5}$]dec-8-ene-2,6-dicarboxylic acid 6-cyclohexylamide 2-[(3,5-dichloro-phenyl)-amide]

(32) 3-(2-Chloro-benzyl)-4-oxo-10-oxa-3-aza-tricyclo[5.2.1.0$^{1,5}$]dec-8-ene-2,6-dicarboxylic acid 2-cyclohexylamide 6-[(3-methoxy-phenyl)-amide]

(33) 3-Benzo[1,3]dioxol-5-ylmethyl-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]

(34) 3-(4-Methoxy-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(35) 3-(3-Methoxy-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(36) 3-(2-Fluoro-benzyl)-4-oxo-10-oxa-3-aza-tricyclo[5.2.1.0$^{1,5}$]dec-8-ene-2,6-dicarboxylic acid 6-[(2,3-dimethyl-cyclohexyl)-amide]2-[(3,5-dimethyl-phenyl)-amide]

(37) 3-(2-Chloro-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(38) 3-(4-Chloro-benzyl)-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(39) 3-(2,3-Dimethyl-cyclohexyl)-4-oxo-10-oxa-3-aza-tricyclo[5.2.1.0$^{1,5}$]dec-8-ene-2,6-dicarboxylic acid 6-[(4-chloro-phenyl)-amide]2-[(2,3-dimethyl-cyclohexyl)-amide]

(40) 3-(3-Methoxy-benzyl)-4-oxo-10-oxa-3-aza-tricyclo[5.2.1.0$^{1,5}$]dec-8-ene-2,6-dicarboxylic acid 6-[(2,3-dimethyl-cyclohexyl)-amide]2-[(3,5-dimethyl-phenyl)-amide]

(41) 3-Benzo[1,3]dioxol-5-ylmethyl-4-oxo-10-oxa-3-aza-tricyclo[5.2.1.0$^{1,5}$]dec-8-ene-2,6-dicarboxylic acid 6-[(3-methoxy-phenyl)-amide]2-[(2-methyl-cyclohexyl)-amide]

(42) 4-Oxo-3-(1-phenyl-ethyl)-10-oxa-3-aza-tricyclo[5.2.1.0$^{1,5}$]dec-8-ene-2,6-dicarboxylic acid 2-[(2,3-dimethyl-cyclohexyl)-amide]6-[(3-methylsulfanyl-phenyl)-amide]

(43) 3-(2,3-Dimethyl-cyclohexyl)-4-oxo-10-oxa-3-aza-tricyclo[5.2.1.0$^{1,5}$]dec-8-ene-2,6-dicarboxylic acid 2-[(2,3-dimethyl-cyclohexyl)-amide]6-[(3-methylsulfanyl-phenyl)-amide]

(44) 3-(3-Methoxy-benzyl)-4-oxo-10-oxa-3-aza-tricyclo[5.2.1.0$^{1,5}$]dec-8-ene-2,6-dicarboxylic acid 6-cyclohexylamide 2-[(3,5-dichloro-phenyl)-amide]

(45) 3-(4-Methyl-cyclohexyl)-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(46) 3-(2-Chloro-benzyl)-4-oxo-10-oxa-3-aza-tricyclo[5.2.1.0$^{1,5}$]dec-8-ene-2,6-dicarboxylic acid 6-cyclohexylamide 2-[(3,5-dichloro-phenyl)-amide]

(47) 3-(4-Fluoro-benzyl)-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(48) 3-(2,3-Dihydro-benzo[1,4]dioxin-2-ylmethyl)-4-oxo-10-oxa-3-aza-tricyclo[5.2.1.0$^{1,5}$]dec-8-ene-2,6-dicarboxylic acid 6-cyclohexylamide 2-[(3,5-dichloro-phenyl)-amide]

(49) 3-(3-Methoxy-benzyl)-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(50) 3-(4-Chloro-benzyl)-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(51) 3-[2-(4-Chloro-phenyl)-ethyl]-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(52) 3-(1-Methyl-3-phenyl-propyl)-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(53) 3-[2-(Benzyl-methyl-amino)-ethyl]-4-oxo-10-oxa-3-aza-tricyclo[5.2.1.0$^{1,5}$]dec-8-ene-2,6-dicarboxylic acid 2-[(3,5-dichloro-phenyl)-amide]6-[(2,3-dimethyl-cyclohexyl)-amide]

(54) 3-[3-(Benzyl-methyl-amino)-propyl]-4-oxo-10-oxa-3-aza-tricyclo[5.2.1.0$^{1,5}$]dec-8-ene-2,6-dicarboxylic acid 6-[(3-chloro-4-fluoro-phenyl)-amide]2-[(2,3-dimethyl-cyclohexyl)-amide]

(55) 3-[2-(Benzyl-methyl-amino)-ethyl]-4-oxo-10-oxa-3-aza-tricyclo[5.2.1.0$^{1,5}$]dec-8-ene-2,6-dicarboxylic acid 2-cyclohexylamide 6-[(4-phenoxy-phenyl)-amide].

2. The compound of claim 1, wherein $R^{15}$ is hydrogen; $R^{16}$ is aryl, substituted aryl, heteroalkyl, substituted heteroalkyl, cycloalkyl or substituted cycloalkyl.

3. The compound of claim 2, wherein $R^{15}$ is hydrogen; and $R^{16}$ is cycloalkyl or substituted cycloalkyl.

4. The compound of claim 1, wherein $R^{17}$ is hydrogen.

5. The compound of claim 1, wherein $R^4$ and $R^5$ are hydrogen.

6. The compound of claim 1, wherein the compound having a structural formula (I) is selected from the group consisting of

(56) 3-(1-Methyl-3-morpholin-4-yl-propyl)-4-oxo-10-oxa-3-aza-tricyclo[5.2.1.0$^{1,5}$]dec-8-ene-2,6-dicarboxylic acid 6-[(2,6-dichloro-tetrahydro-pyran-4-yl)-amide]2-[(2,3-dimethyl-phenyl)-amide]

(57) 3-(1-Methyl-3-pyridin-4-yl-propyl)-4-oxo-10-oxa-3-aza-tricyclo[5.2.1.0$^{1,5}$]decane-2,6-dicarboxylic acid 6-[(2,6-dichloro-pyridin-4-yl)-amide]2-[(2,3-dimethyl-cyclohexyl)-amide]

(58) 3-(4-Chloro-benzyl)-4-oxo-10-oxa-3-aza-tricyclo[5.2.1.0$^{1,5}$]dec-8-ene-2,6-dicarboxylic acid 6-cyclohexylamide 2-[(3,5-dimethyl-phenyl)-amide]

(59) 3-(4-Chloro-benzyl)-4-oxo-10-oxa-3-aza-tricyclo [5.2.1.0$^{1,5}$]decane-2,6-dicarboxylic acid 6-[(3,5-dichloro-phenyl)-amide]2-[(2,3-dimethyl-cyclohexyl)-amide]

(60) 3-(4-Fluoro-piperazin-1-ylmethyl)-4-oxo-10-oxa-3-aza-tricyclo[5.2.1.0$^{1,5}$]dec-8-ene-2,6-dicarboxylic acid 6-[(6-chloro-4-fluoro-pyridin-2-yl)-amide]2-[(2,3-dimethyl-piperazin-1-yl)-amide]

(61) 345-Fluoro-pyridin-2-ylmethyl)-4-oxo-10-oxa-2,3, 6-triaza-tricyclo[5.2.1.0$^{1,5}$]dec-8-ene-2,6-dicarboxylic acid 6-[(3-chloro-5-fluoro-phenyl)-amide]2-[(2,3-dimethyl-cyclohexyl)-amide]

(62) 4-(1-Methyl-2-phenylamino-ethyl)-5-oxo-11-oxa-4-aza-tricyclo[6.2.1.0$^{1,6}$]undecane-3,7-dicarboxylic acid 7-[(4-chloro-5-fluoro-pyridin-2-yl)-amide]3-[(2,3-dimethyl-piperazin-1-yl)-amide]

(63) 4-(4-Fluoro-piperazin-1-ylmethyl)-5-oxo-11-oxa-4-aza-tricyclo[6.2.1.0$^{1,6}$]undec-9-ene-3,7-dicarboxylic acid 7-[(6-chloro-4-fluoro-pyridin-2-yl)-amide]3-[(2,3-dimethyl-piperazin-1-yl)-amide]

(64) 4-(Cyclopropylaminomethyl-methyl-amino)-5-oxo-11-oxa-4-aza-tricyclo[6.2.1.0$^{1,6}$]undec-9-ene-3,7-dicarboxylic acid 7-[(4,5-difluoro-pyridin-2-yl)-amide]3-[(2,3-dimethyl-morpholin-4-yl)-amide]

(65) 4-[2-(4-Chloro-piperazin-1-yl)-1-methyl-ethyl]-5-oxo-11-oxa-4-aza-tricyclo[6.2.1.0$^{1,6}$]undecane-3,7-dicarboxylic acid 7-[(4,5-difluoro-pyridin-2-yl)-amide]3-[(2,3-dimethyl-piperazin-1-yl)-amide]

(66) 5-Oxo-4-{1-[(pyridin-4-ylmethyl)-amino]-ethyl}-11-oxa-4-aza-tricyclo[6.2.1.0$^{1,6}$]undecane-3,7-dicarboxylic acid 7-[(3,5-dichloro-phenyl)-amide]3-[(2,3-dimethyl-piperidin-1-yl)-amide]

or a salt, solvate, ester, and/or prodrug thereof.

7. A pharmaceutical composition comprising a compound having a structural Formula (I) as defined in claim 1, or a salt, solvate, ester, and/or prodrug thereof; and
a pharmaceutically acceptable vehicle.

8. The pharmaceutical composition of claim 7, wherein $R^{15}$ is hydrogen; $R^{16}$ is aryl, substituted aryl, heteroalkyl, substituted heteroalkyl, cycloalkyl or substituted cycloalkyl.

9. The pharmaceutical composition of claim 7, wherein $R^{17}$ is hydrogen.

10. The pharmaceutical composition of claim 7, wherein $R^{15}$ is hydrogen and $R^{16}$ is cycloalkyl or substituted cycloalkyl.

11. The pharmaceutical composition of claim 7, wherein the compound having a structural Formula (I) is selected from the group consisting of

(56) 3-(1-Methyl-3-morpholin-4-yl-propyl)-4-oxo-10-oxa-3-aza-tricyclo[5.2.1.01,5]dec-8-ene-2,6-dicarboxylic acid 6-[(2,6-dichloro-tetrahydro-pyran-4-yl)-amide]2-[(2,3-dimethyl-phenyl)-amide]

(57) 3-(1-Methyl-3-pyridin-4-yl-propyl)-4-oxo-10-oxa-3-aza-tricyclo[5.2.1.01,5]decane-2,6-dicarboxylic acid 6-[(2,6-dichloro-pyridin-4-yl)-amide]2-[(2,3-dimethyl-cyclohexyl)-amide]

(58) 3-(4-Chloro-benzyl)-4-oxo-10-oxa-3-aza-tricyclo [5.2.1.01,5]dec-8-ene-2,6-dicarboxylic acid 6-cyclohexylamide 2-[(3,5-dimethyl-phenyl)-amide]

(59) 3-(4-Chloro-benzyl)-4-oxo-10-oxa-3-aza-tricyclo [5.2.1.01,5]decane-2,6-dicarboxylic acid 6-[(3,5-dichloro-phenyl)-amide]2-[(2,3-dimethyl-cyclohexyl)-amide]

(60) 3-(4-Fluoro-piperazin-1-ylmethyl)-4-oxo-10-oxa-3-aza-tricyclo[5.2.1.01,5]dec-8-ene-2,6-dicarboxylic acid 6-[(6-chloro-4-fluoro-pyridin-2-yl)-amide]2-[(2,3-dimethyl-piperazin-1-yl)-amide]

(61) 3-(5-Fluoro-pyridin-2-ylmethyl)-4-oxo-10-oxa-2,3, 6-triaza-tricyclo[5.2.1.01,5]dec-8-ene-2,6-dicarboxylic acid 6-[(3-chloro-5-fluoro-phenyl)-amide]2-[(2,3-dimethyl-cyclohexyl)-amide]

(62) 4-(1-Methyl-2-phenylamino-ethyl)-5-oxo-11-oxa-4-aza-tricyclo[6.2.1.01,6]undecane-3,7-dicarboxylic acid 7-[(4-chloro-5-fluoro-pyridin-2-yl)-amide]3-[(2,3-dimethyl-piperazin-1-yl)-amide]

(63) 4-(4-Fluoro-piperazin-1-ylmethyl)-5-oxo-11-oxa-4-aza-tricyclo[6.2.1.01,6]undec-9-ene-3,7-dicarboxylic acid 7-[(6-chloro-4-fluoro-pyridin-2-yl)-amide]3-[(2,3-dimethyl-piperazin-1-yl)-amide]

(64) 4-(Cyclopropylaminomethyl-methyl-amino)-5-oxo-11-oxa-4-aza-tricyclo[6.2.1.01,6]undec-9-ene-3,7-dicarboxylic acid 7-[(4,5-difluoro-pyridin-2-yl)-amide]3-[(2,3-dimethyl-morpholin-4-yl)-amide]

(65) 4-[2-(4-Chloro-piperazin-1-yl)-1-methyl-ethyl]-5-oxo-11-oxa-4-aza-tricyclo[6.2.1.01,6]undecane-3,7-dicarboxylic acid 7-[(4,5-difluoro-pyridin-2-yl)-amide]3-[(2,3-dimethyl-piperazin-1-yl)-amide]

(66) 5-Oxo-4-{1-[(pyridin-4-ylmethyl)-amino]-ethyl}-11-oxa-4-aza-tricyclo[6.2.1.01,6]undecane-3,7-dicarboxylic acid 7-[(3,5-dichloro-phenyl)-amide]3-[(2,3-dimethyl-piperidin-1-yl)-amide]

or a salt, solvate, ester, and/or prodrug thereof.

12. A method for treating a condition, disorder, or disease, in a patient in need thereof comprising administering to the patient a therapeutically effective amount of the compound of formula (I) as defined in claim 1, or a salt, solvent, ester, and/or prodrug thereof, wherein the condition, disorder, or disease is pain.

13. The pharmaceutical composition of claim 7, further comprises an additional active agent.

\* \* \* \* \*